US008853260B2

(12) United States Patent
Desai et al.

(10) Patent No.: US 8,853,260 B2
(45) Date of Patent: Oct. 7, 2014

(54) FORMULATIONS OF PHARMACOLOGICAL AGENTS, METHODS FOR THE PREPARATION THEREOF AND METHODS FOR THE USE THEREOF

(75) Inventors: Neil P. Desai, Santa Monica, CA (US); Patrick Soon-Shiong, Los Angeles, CA (US)

(73) Assignee: Abraxis BioScience, LLC, Los Angeles, CA (US)

( * ) Notice: Subject to any disclaimer, the term of this patent is extended or adjusted under 35 U.S.C. 154(b) by 1070 days.

(21) Appl. No.: 11/520,479

(22) Filed: Sep. 12, 2006

(65) Prior Publication Data

US 2007/0093547 A1    Apr. 26, 2007

Related U.S. Application Data

(63) Continuation of application No. 09/446,783, filed as application No. PCT/US98/13272 on Jun. 26, 1998, and a continuation-in-part of application No. 08/926,155, filed on Sep. 9, 1997, now Pat. No. 6,096,331.

(60) Provisional application No. 60/051,021, filed on Jun. 27, 1997.

(51) Int. Cl.
| *A01N 43/02* | (2006.01) |
| *A01N 25/00* | (2006.01) |
| *A61K 31/335* | (2006.01) |
| *A61K 47/00* | (2006.01) |

(52) U.S. Cl.
USPC .......................................... 514/449; 514/776

(58) Field of Classification Search
None
See application file for complete search history.

(56) References Cited

U.S. PATENT DOCUMENTS

| 4,452,817 A | 6/1984 | Glen et al. |
| 4,534,899 A | 8/1985 | Sears |

(Continued)

FOREIGN PATENT DOCUMENTS

| CN | 1148957 A | 5/1997 |
| EP | 0 326 618 A1 | 8/1989 |

(Continued)

OTHER PUBLICATIONS

Vippagunta et al (Vippagunta et al. Crystalline solids. Advanced Drug Delivery Reviews. 2001;48:3-26.*

(Continued)

*Primary Examiner* — Trevor Love
(74) *Attorney, Agent, or Firm* — Morrison & Foerster LLP

(57) ABSTRACT

In accordance with the present invention, there are provided compositions and methods useful for the in vivo delivery of substantially water insoluble pharmacologically active agents (such as the anticancer drug paclitaxel) in which the pharmacologically active agent is delivered in the form of suspended particles coated with protein (which acts as a stabilizing agent). In particular, protein and pharmacologically active agent in a biocompatible dispersing medium are subjected to high shear, in the absence of any conventional surfactants, and also in the absence of any polymeric core material for the particles. The procedure yields particles with a diameter of less than about 1 micron. The use of specific composition and preparation conditions (e.g., addition of a polar solvent to the organic phase), and careful selection of the proper organic phase and phase fraction, enables the reproducible production of unusually small nanoparticles of less than 200 nm diameter, which can be sterile-filtered. The particulate system produced according to the invention can be converted into a redispersible dry powder comprising nanoparticles of water-insoluble drug coated with a protein, and free protein to which molecules of the pharmacological agent are bound. This results in a unique delivery system, in which part of the pharmacologically active agent is readily bioavailable (in the form of molecules bound to the protein), and part of the agent is present within particles without any polymeric matrix therein.

27 Claims, 4 Drawing Sheets

(56) References Cited

U.S. PATENT DOCUMENTS

| | | | |
|---|---|---|---|
| 4,693,367 A | 9/1987 | Mathieu | |
| 4,798,846 A | 1/1989 | Glen et al. | |
| 4,963,367 A | 10/1990 | Ecanow | |
| 5,059,699 A | 10/1991 | Kingston et al. | |
| 5,069,936 A | 12/1991 | Yen | |
| 5,362,478 A | 11/1994 | Desai et al. | |
| 5,362,831 A | 11/1994 | Mongelli | |
| 5,399,363 A | 3/1995 | Liversidge et al. | |
| 5,407,683 A * | 4/1995 | Shively | 424/439 |
| 5,415,869 A | 5/1995 | Straubinger et al. | |
| 5,424,073 A | 6/1995 | Rahman et al. | |
| 5,439,686 A | 8/1995 | Desai et al. | |
| 5,498,421 A | 3/1996 | Grinstaff et al. | |
| 5,505,932 A | 4/1996 | Grinstaff et al. | |
| 5,508,021 A | 4/1996 | Grinstaff et al. | |
| 5,512,268 A | 4/1996 | Grinstaff et al. | |
| 5,560,933 A | 10/1996 | Soon-Shiong et al. | |
| 5,565,478 A | 10/1996 | Kohn et al. | |
| 5,567,434 A | 10/1996 | Szoka, Jr. | |
| 5,616,330 A * | 4/1997 | Kaufman et al. | 424/400 |
| 5,616,608 A | 4/1997 | Kinsella et al. | |
| 5,626,862 A | 5/1997 | Brem et al. | |
| 5,626,867 A | 5/1997 | Eibl et al. | |
| 5,635,207 A | 6/1997 | Grinstaff et al. | |
| 5,639,473 A | 6/1997 | Grinstaff et al. | |
| 5,648,090 A | 7/1997 | Rahman et al. | |
| 5,650,156 A | 7/1997 | Grinstaff et al. | |
| 5,651,986 A | 7/1997 | Brem et al. | |
| 5,665,382 A | 9/1997 | Grinstaff et al. | |
| 5,665,383 A | 9/1997 | Grinstaff et al. | |
| 5,670,536 A | 9/1997 | Durr et al. | |
| 5,681,846 A * | 10/1997 | Trissel | 514/449 |
| 5,683,715 A | 11/1997 | Boni et al. | |
| 5,703,117 A | 12/1997 | Mayhew et al. | |
| 5,716,981 A | 2/1998 | Hunter et al. | |
| 5,725,804 A * | 3/1998 | Yen | 516/77 |
| 5,731,334 A | 3/1998 | Wrasidlo | |
| 5,733,925 A | 3/1998 | Kunz et al. | |
| 5,756,537 A | 5/1998 | Gill | |
| 5,766,635 A | 6/1998 | Spenleuhauer et al. | |
| 5,795,909 A | 8/1998 | Shashoua et al. | |
| 5,811,447 A | 9/1998 | Kunz et al. | |
| 5,886,026 A | 3/1999 | Hunter et al. | |
| 5,916,596 A * | 6/1999 | Desai et al. | 424/489 |
| 5,928,669 A | 7/1999 | Davis et al. | |
| 5,945,033 A | 8/1999 | Yen | |
| 5,977,163 A * | 11/1999 | Li et al. | 514/449 |
| 5,981,568 A | 11/1999 | Kunz et al. | |
| 5,994,341 A | 11/1999 | Hunter et al. | |
| 5,997,904 A | 12/1999 | Magdassi et al. | |
| 6,051,600 A | 4/2000 | Mayhew et al. | |
| 6,066,668 A | 5/2000 | Hausheer et al. | |
| 6,074,659 A | 6/2000 | Kunz et al. | |
| 6,096,331 A | 8/2000 | Desai et al. | |
| 6,107,332 A | 8/2000 | Ali et al. | |
| 6,120,805 A | 9/2000 | Spenlehauer et al. | |
| 6,143,276 A | 11/2000 | Unger | |
| 6,146,659 A | 11/2000 | Rahman | |
| 6,146,663 A | 11/2000 | Bissery et al. | |
| 6,179,817 B1 | 1/2001 | Zhong | |
| 6,197,051 B1 | 3/2001 | Zhong | |
| 6,197,349 B1 | 3/2001 | Westesen et al. | |
| 6,268,390 B1 | 7/2001 | Kunz | |
| 6,306,421 B1 | 10/2001 | Kunz et al. | |
| 6,322,805 B1 | 11/2001 | Kim et al. | |
| 6,432,928 B1 | 8/2002 | Szente et al. | |
| 6,441,025 B2 | 8/2002 | Li et al. | |
| 6,458,373 B1 | 10/2002 | Lambert et al. | |
| 6,500,461 B2 | 12/2002 | Perkins et al. | |
| 6,506,405 B1 | 1/2003 | Desai et al. | |
| 6,528,067 B1 | 3/2003 | Magdassi et al. | |
| 6,537,579 B1 | 3/2003 | Desai et al. | |
| 6,565,842 B1 | 5/2003 | Sojomihardio et al. | |
| 6,610,735 B2 | 8/2003 | Broder et al. | |
| 6,652,884 B2 | 11/2003 | Falciani | |
| 6,743,826 B1 | 6/2004 | Hegedus et al. | |
| 6,749,868 B1 | 6/2004 | Desai et al. | |
| 6,753,006 B1 | 6/2004 | Desai et al. | |
| 6,759,431 B2 | 7/2004 | Hunter et al. | |
| 7,238,369 B2 | 7/2007 | McDonald et al. | |
| 7,332,568 B2 | 2/2008 | Trieu et al. | |
| 8,138,229 B2 | 3/2012 | Desai et al. | |
| 8,257,733 B2 | 9/2012 | Desai et al. | |
| 8,268,348 B2 | 9/2012 | Desai et al. | |
| 8,314,156 B2 | 11/2012 | Desai et al. | |
| 2003/0054042 A1 | 3/2003 | Liversidge et al. | |
| 2003/0087985 A1 | 5/2003 | Hubbell et al. | |
| 2003/0199425 A1 | 10/2003 | Desai et al. | |
| 2005/0004002 A1 | 1/2005 | Desai et al. | |
| 2006/0083782 A1 | 4/2006 | Desai et al. | |
| 2006/0121119 A1 | 6/2006 | Zenoni et al. | |
| 2006/0210638 A1 | 9/2006 | Liversidge et al. | |
| 2006/0257326 A1 | 11/2006 | Desai et al. | |
| 2006/0263434 A1 | 11/2006 | Desai et al. | |
| 2007/0020337 A1 | 1/2007 | Zenoni et al. | |
| 2007/0082838 A1 | 4/2007 | De et al. | |
| 2007/0087022 A1 | 4/2007 | Desai et al. | |
| 2007/0092563 A1 | 4/2007 | Desai et al. | |
| 2007/0116774 A1 | 5/2007 | Desai et al. | |
| 2007/0117133 A1 | 5/2007 | Trieu et al. | |
| 2007/0117744 A1 | 5/2007 | Desai et al. | |
| 2007/0117862 A1 | 5/2007 | Desai et al. | |
| 2007/0117863 A1 | 5/2007 | Desai et al. | |
| 2007/0128290 A1 | 6/2007 | Desai et al. | |
| 2007/0129448 A1 | 6/2007 | Desai et al. | |
| 2007/0166388 A1 | 7/2007 | Desai et al. | |
| 2007/0196361 A1 | 8/2007 | Soon-Shiong et al. | |
| 2008/0063724 A1 | 3/2008 | Desai et al. | |
| 2008/0153738 A1 | 6/2008 | Desai et al. | |
| 2008/0153739 A1 | 6/2008 | Desai et al. | |
| 2008/0160095 A1 | 7/2008 | Desai et al. | |
| 2008/0161382 A1 | 7/2008 | Desai et al. | |
| 2008/0166389 A1 | 7/2008 | Desai et al. | |
| 2008/0280987 A1 | 11/2008 | Desai et al. | |
| 2009/0098210 A1 | 4/2009 | Desai et al. | |
| 2009/0175951 A1 | 7/2009 | Liversidge | |
| 2009/0196933 A1 | 8/2009 | Desai et al. | |
| 2009/0263483 A1 | 10/2009 | Desai et al. | |
| 2009/0304805 A1 | 12/2009 | Desai et al. | |
| 2010/0035800 A1 | 2/2010 | Desai et al. | |
| 2010/0048499 A1 | 2/2010 | Desai et al. | |
| 2010/0112077 A1 | 5/2010 | Desai et al. | |
| 2010/0166869 A1 | 7/2010 | Desai et al. | |
| 2010/0183728 A1 | 7/2010 | Desai et al. | |
| 2010/0196490 A1 | 8/2010 | Desai et al. | |
| 2010/0215751 A1 | 8/2010 | Desai et al. | |
| 2010/0226996 A1 | 9/2010 | Desai et al. | |
| 2010/0297243 A1 | 11/2010 | Desai et al. | |
| 2011/0052708 A1 | 3/2011 | Soon-Shiong et al. | |
| 2011/0064812 A1 | 3/2011 | Bahl et al. | |
| 2011/0118342 A1 | 5/2011 | De et al. | |
| 2011/0151012 A1 | 6/2011 | Desai et al. | |
| 2011/0165256 A1 | 7/2011 | Desai et al. | |
| 2011/0196026 A1 | 8/2011 | De et al. | |
| 2011/0301248 A1 | 12/2011 | Desai et al. | |
| 2012/0004177 A1 | 1/2012 | Desai et al. | |
| 2012/0070502 A1 | 3/2012 | Desai et al. | |
| 2012/0076862 A1 | 3/2012 | Desai et al. | |
| 2012/0128732 A1 | 5/2012 | Trieu et al. | |
| 2012/0189701 A1 | 7/2012 | Desai et al. | |
| 2012/0231082 A1 | 9/2012 | Desai et al. | |
| 2012/0283205 A1 | 11/2012 | Desai et al. | |
| 2012/0308612 A1 | 12/2012 | De et al. | |
| 2013/0045240 A1 | 2/2013 | Tao et al. | |
| 2013/0071438 A1 | 3/2013 | Desai et al. | |
| 2013/0115296 A1 | 5/2013 | Yeo et al. | |
| 2013/0195922 A1 | 8/2013 | Desai et al. | |
| 2013/0195983 A1 | 8/2013 | Desai et al. | |
| 2013/0195984 A1 | 8/2013 | Desai et al. | |
| 2013/0202709 A1 | 8/2013 | Desai et al. | |
| 2013/0209518 A1 | 8/2013 | Desai et al. | |
| 2013/0244952 A1 | 9/2013 | Desai et al. | |

(56) References Cited

U.S. PATENT DOCUMENTS

| | | |
|---|---|---|
| 2013/0266659 A1 | 10/2013 | Desai et al. |
| 2013/0280336 A1 | 10/2013 | Desai et al. |
| 2013/0280337 A1 | 10/2013 | Desai et al. |

FOREIGN PATENT DOCUMENTS

| | | |
|---|---|---|
| JP | 63-502117 A | 8/1988 |
| WO | WO-87/04592 A1 | 8/1987 |
| WO | WO-93/24476 A1 | 12/1993 |
| WO | WO-94/18954 A1 | 9/1994 |
| WO | WO-95/03036 A1 | 2/1995 |
| WO | WO-96/02247 A1 | 2/1996 |
| WO | WO-96/29064 A1 | 9/1996 |
| WO | WO-96/40091 A1 | 12/1996 |
| WO | WO-96/40829 A1 | 12/1996 |
| WO | WO-96/41236 A1 | 12/1996 |
| WO | WO-97/10849 A1 | 3/1997 |
| WO | WO-97/45105 A1 | 12/1997 |
| WO | WO-98/14174 A1 | 4/1998 |
| WO | WO-98/14174 C1 | 4/1998 |
| WO | WO 98/14175 A1 | 4/1998 |
| WO | WO-98/43618 A2 | 10/1998 |
| WO | WO-98/43618 A3 | 10/1998 |
| WO | WO-98/43618 A9 | 10/1998 |
| WO | WO 99/00113 A1 | 1/1999 |
| WO | WO-99/13914 A1 | 3/1999 |
| WO | WO 00/71079 A2 | 11/2000 |
| WO | WO 00/71079 A3 | 11/2000 |
| WO | WO 01/89522 A1 | 11/2001 |
| WO | WO 02/87545 A1 | 11/2002 |
| WO | WO-03/96944 A1 | 11/2003 |
| WO | WO 2004/052401 A2 | 6/2004 |
| WO | WO 2004/052401 A3 | 6/2004 |
| WO | WO 2006/089290 A1 | 8/2006 |
| WO | WO 2007/027819 A2 | 3/2007 |
| WO | WO 2007/027819 A3 | 3/2007 |
| WO | WO 2007/027941 A2 | 3/2007 |
| WO | WO 2007/027941 A3 | 3/2007 |
| WO | WO 2008/027055 A1 | 3/2008 |
| WO | WO 2008/057562 A1 | 5/2008 |
| WO | WO 2008/076373 A1 | 6/2008 |
| WO | WO 2008/109163 A1 | 9/2008 |
| WO | WO 2008/137148 A2 | 11/2008 |
| WO | WO 2008/137148 A3 | 11/2008 |
| WO | WO 2008/150532 A1 | 12/2008 |
| WO | WO 2009/126175 A1 | 10/2009 |
| WO | WO 2009/126401 A1 | 10/2009 |
| WO | WO 2009/126938 A1 | 10/2009 |
| WO | WO 2010/068925 A1 | 6/2010 |
| WO | WO 2010/105172 A1 | 9/2010 |
| WO | WO 2010/118365 A1 | 10/2010 |
| WO | WO 2010/121000 A1 | 10/2010 |
| WO | WO-2011/025838 A1 | 3/2011 |
| WO | WO-2011/119988 A1 | 9/2011 |
| WO | WO-2011/123393 A1 | 10/2011 |
| WO | WO-2011/123395 A1 | 10/2011 |
| WO | WO-2011/153009 A1 | 12/2011 |
| WO | WO-2011/153010 A1 | 12/2011 |
| WO | WO-2011/156119 A1 | 12/2011 |
| WO | WO-2012/149451 A1 | 11/2012 |
| WO | WO-2013/090634 A1 | 6/2013 |

OTHER PUBLICATIONS

Bartoli, M.H. et al. (Apr.-Jun. 1990). "In Vitro and In Vivo Antitumoral Activity of Free, and Encapsulated Taxol," *Journal of Microencapsulation* 7(2):191-197.

Desai, N.P. et al. (Apr. 1994). "Controlled and Targeted Drug Delivery With Biocompatible Protein Shell Microspheres," *The 20th Annual Meeting of the Society for Biomaterials*, Boston, MA, Apr. 5-9, 1994, one page.

Desai, N.P. et al. (Oct.-Nov. 1994). "Intravenous Targeted Delivery of Chemo-therapeutic Agents in Protein Microspheres," *XIV International Cancer Progress*, New Delhi, India, Oct. 30-Nov. 5, 1994, one page.

Desai, N.P. et al. (Mar. 1995). "In Vivo Drug Delivery With Biocompatible Protein Shell Microspheres," *The 21st Annual Meeting of the Society for Biomaterials*, San Francisco, CA, Mar. 18-22, 1995, one page.

Desai, N.P. et al. (Aug. 1995). "Protein Microcapsules as Drug Delivery Vehicles," *26th Annual Meeting of the Fine Particle Society*, Chicago, IL, Aug. 22-25, 1995, one page.

Desai, N.P. et al. (Apr.-May 1997). "Protein-Stabilized Nanoparticles as Drug Delivery Vehicles," *Transactions: 23rd Annual Meeting of the Society for Biomaterials*, New Orleans, LA, Apr. 30-May 4, 1997, 20:172.

Desai, N.P. et al. (Apr. 1998). "Protein Based Nanoparticle Delivery Systems," *28th Annual Meeting of the Fine Particle Society*, Dallas, TX, Apr. 1-3, 1998, one page.

Dosio, F. et al. (1997). "Preparation, Characterization and Properties In Vitro and In Vivo of a Paclitaxel-Albumin Conjugate," *J. Cont. Rel.* 47:293-204.

Grinstaff, M.W. et al. (Mar. 1994). "Intravenous Targeted Delivery of Taxol in Protein Microspheres," *Abstracts of Papers 207th National Meeting of the American Chemical Society*, 1994, San Diego, CA, Mar. 13-17, 1994, 207(1-2), Abstract No. 91, one page.

Leyland-Jones, B. (Feb. 1993). "Targeted Drug Delivery," *Seminars in Oncology* 20(1):12-17.

Mathew, A.E. et al. (1992). "Synthesis and Evaluation of Some Water-Soluble Prodrugs and Derivatives of Taxol with Antitumor Activity," *J. Med. Chem.* 35(1):145-151.

Merisko-Liversidge, E. (1996). "Formulation and Antitumor Activity Evaluation of Nanocrystalline Suspensions of Poorly Soluble Anticancer Drugs," *Pharmaceutical Research* 13(2):272-278.

Riondel, J. et al. (Jan.-Feb. 1992). "Effects of Free and Liposome-Encapsulated Taxol on Two Brain Tumors Xenografted into Nude Mice," *In Vivo* 6(1):23-27.

Non-Final Office Action mailed on Jun. 22, 2007, for U.S. Appl. No. 11/544,737, filed on Oct. 5, 2006, 9 pages.

Non-Final Office Action mailed on Jun. 22, 2007, for U.S. Appl. No. 11/544,794, filed on Oct. 5, 2006, 9 pages.

Non-Final Office Action mailed on Jun. 14, 2007, for U.S. Appl. No. 11/544,523, filed on Oct. 5, 2006, 8 pages.

Non-Final Office Action mailed on Jun. 22, 2007, for U.S. Appl. No. 11/544,781, filed on Oct. 5, 2006, 9 pages.

Non-Final Office Action mailed on Jun. 22, 2007, for U.S. Appl. No. 11/635,253, filed on Dec. 5, 2006, 9 pages.

Non-Final Office Action mailed on Jun. 22, 2007, for U.S. Appl. No. 11/635,252, filed on Dec. 5, 2006, 9 pages.

U.S. Appl. No. 09/446,783, filed on May 16, 2000, for Desai et al.
U.S. Appl. No. 09/937,840, filed on Jan. 28, 2002, for Desai et al.
U.S. Appl. No. 11/553,339, filed on Oct. 26, 2006, for Desai et al.
U.S. Appl. No. 11/833,179, filed on Aug. 2, 2007, for Desai et al.
U.S. Appl. No. 11/833,188, filed on Aug. 2, 2007, for Desai et al.
U.S. Appl. No. 11/880,218, filed on Jul. 19, 2007, for Desai et al.
U.S. Appl. No. 11/880,314, filed on Jul. 20, 2007, for Desai et al.
U.S. Appl. No. 11/890,006, filed on Aug. 3, 2007, for Desai et al.
U.S. Appl. No. 11/890,041, filed on Aug. 3, 2007, for Desai et al.
U.S. Appl. No. 11/890,197, filed on Aug. 3, 2007, for Desai et al.
U.S. Appl. No. 11/890,599, filed on Aug. 6, 2007, for Desai et al.
U.S. Appl. No. 11/890,603, filed on Aug. 6, 2007, for Desai et al.
U.S. Appl. No. 11/890,639, filed on Aug. 6, 2007, for Desai et al.
U.S. Appl. No. 11/890,648, filed on Aug. 6, 2007, for Desai et al.
U.S. Appl. No. 11/890,819, filed on Aug. 7, 2007, for Desai et al.
U.S. Appl. No. 11/897,724, filed on Aug. 31, 2007, for Desai et al.
U.S. Appl. No. 12/051,782, filed on Mar. 19, 2008, for Desai et al.

*American BioScience, Inc. v. Baker Norton Pharmaceuticals, Inc. et al.*, Case No. CV 00-09589 (MRP), before United States District Court for the Central District of California, 2002 U.S. Dist. Lexis 512, Jan. 10, 2002, four pages.

Pazdur, R. et al. (Oct. 1993). "The Taxoids: Paclitaxel (Taxol) and Docetaxel (Taxotere)," *Cancer Treat. Rev.* 19(4):351-386. (Abstract only, 1 page).

U.S. Appl. No. 12/331,924, filed on Dec. 10, 2008, for Desai et al.
U.S. Appl. No. 12/474,218, filed on May 28, 2009, for Desai et al.
U.S. Appl. No. 12/513,843, filed on May 6, 2009, for Desai et al.

(56) References Cited

OTHER PUBLICATIONS

Groves, M. J. at al. (May 31, 1995). "Introduction," in *Aseptic Pharmaceutical Manufacturing II*, Applications for the 1990s; Chapter 1, edited by M. J. Groves and R. Murty, Interpharm Press, Inc., pp. 1-9.

Muller, B. G. et al. (Jan. 1996). "Albumin Nanospheres as Carriers for Passive Drug Targeting: An Optimized Manufacturing Technique," *Pharmaceutical Research* 13(1):32-37.

Verrechia, T. et al. (Sep. 1995). "Non-Stealth (Poly (Lactic Acid/Albumin)) and Stealth (Poly (Lactic Acid-Polyethylene Glycol)) Nanoparticles as Injectable Drug Carriers," *J. Controlled Release* 36:49-61.

Non-Final Office Action mailed on Apr. 16, 2009, for U.S. Appl. No. 11/890,197, filed on Aug. 3, 2007, 9 pages.

Non Final Office Action issued May 12, 2009, for U.S. Appl. No. 11/880,218, filed on Aug. 3, 2007, 11 pages.

Non-Final Office Action mailed on Jan. 5, 2010 for U.S. Appl. No. 11/890,197, filed on Aug. 3, 2007, 9 pages.

Non-Final Office Action mailed on Jan. 27, 2010, for U.S. Appl. No. 11/880,218, filed on Jul. 19, 2007, 10 pages.

Ron, N. et al. (Apr. 2008). "Comparison of Physicochemical Characteristics and Stability of Three Novel Formulations of Paclitaxel: Abraxane, Nanoxel, and Genexol PM," Abstract No. 5622, *presented at $99^{th}$ AACR Annual Meeting*, San Diego, CA, Apr. 12-16, 2008, located at <http://www.aacrmeetingabstracts.org/cgi/content/meeting_abstract/2008/1_Annual_Meeting/5622?maxtoshow=&hits=10&RESULTFORMAT=1&author1=ron&andorexacttitle=and&andorexacttitleabs=and&searchid=1&FIRSTINDEX=0&sortspec=relevance&fdate=1/1/2004&tdate=12/31/2009&resource-type=HWCIT>, last visited on Sep. 30, 2010, 2 pages.

Yao, J. H. et al. (Jun. 1, 1993). "Theory and Simulation of Ostwald Ripening," *Phys. Review* 47(21): 14110-14125.

U.S. Appl. No. 13/038,287, filed Mar. 1, 2011, for Desai et al.
U.S. Appl. No. 13/073,824, filed Mar. 28, 2011, for Desai et al.
U.S. Appl. No. 13/073,861, filed Mar. 28, 2011, for Desai et al.
U.S. Appl. No. 13/133,367, internationally filed Dec. 11, 2009, for Trieu et al.
U.S. Appl. No. 13/228,323, filed on Sep. 8, 2011, for Desai et al.
U.S. Appl. No. 13/255,893, internationally filed on Mar. 12, 2010, for Desai et al.
U.S. Appl. No. 13/263,723, internationally filed on Apr. 9, 2010, for Desai et al.

Burns, J.L. et al. (1997). "A Light Scattering Study of the Fractal Aggregation Behavior of a Model Colloidal System," *Langmuir* 13(24):6413-6420.

Kallay, N. et al. (2002). "Stability of Nanodispersions: A Model for Kinetics of Aggregation of Nanoparticles," *Journal of Colloid and Interface Science* 253:70-76.

Schwarz, C. et al. (1997). "Freeze-Drying of Drug-Free and Drug-Loaded Solid Lipid Nanoparticles (SLN)," *International Journal of Pharmaceutics* 157:171-179.

U.S. Appl. No. 13/777,980, filed on Feb. 26, 2013, for Desai et al.
U.S. Appl. No. 13/777,988, filed on Feb. 26, 2013, for Desai et al.
U.S. Appl. No. 13/776,481, filed on Feb. 25, 2013, for Desai et al.
U.S. Appl. No. 13/776,484, filed on Feb. 25, 2013, for Desai et al.
U.S. Appl. No. 13/779,625, filed on Feb. 27, 2013, for Desai et al.
U.S. Appl. No. 13/781,482, filed on Feb. 28, 2013, for Desai et al.
U.S. Appl. No. 13/781,479, filed on Feb. 28, 2013, for Desai et al.
U.S. Appl. No. 13/781,489, filed on Feb. 28, 2013, for Trieu et al.
U.S. Appl. No. 13/781,487, filed on Feb. 28, 2013, for Tao et al.
U.S. Appl. No. 13/781,480, filed on Feb. 28, 2013, for Yeo et al.
U.S. Appl. No. 13/782,990, filed on Mar. 1, 2013, for Desai et al.
U.S. Appl. No. 13/782,988, filed on Mar. 1, 2013, for Desai et al.
U.S. Appl. No. 13/782,984, filed on Mar. 1, 2013, for Desai et al.
U.S. Appl. No. 13/783,122, filed on Mar. 1, 2013, for Desai et al.
U.S. Appl. No. 13/701,001, filed on May 20, 2011, for Desai et al.
U.S. Appl. No. 13/782,992, filed on Mar. 1, 2013, for Desai et al.
U.S. Appl. No. 13/794,705, filed on Mar. 12, 2013, for Desai et al.
U.S. Appl. No. 13/791,841, filed on Mar. 12, 2013, for Desai et al.
U.S. Appl. No. 13/794,480, filed on Mar. 12, 2013, for Desai et al.
U.S. Appl. No. 13/794,486, filed on Mar. 12, 2013, for Heise et al.
U.S. Appl. No. 13/794,712, filed on Mar. 11, 2013, for Pierce et al.
U.S. Appl. No. 12/240,893, filed on Sep. 29, 2008, for Desai et al.
U.S. Appl. No. 12/271,748, filed on Nov. 14, 2008, for Desai et al.

Stearns, M.E. et al. (Jul. 1, 1992). "Taxol Blocks Processes Essential for Prostate Tumor Cell (PC-3 ML) Invasion and Metastases," *Cancer Search* 52(13): 3776-3781.

Walter, K.A. et al. (Apr. 15, 1994). "Interstitial Taxol Delivered From a Biodegradable Polymer Implant Against Experimental Malignant Glioma," *Cancer Research* 54:2207-2212.

Extended European Search Report and European Search Opinion mailed on Jan. 27, 2014, for European Patent Application No. 10011099.8, filed on Jun. 26, 1998, nineteen pages.

* cited by examiner

Treatment initiated after s.c. tumors reach 200 mm$^3$ or 200 mg
Treatment days 13-17; n = 5 mice in each group

* Treatment days

FORMULATIONS OF PHARMACOLOGICAL AGENTS, METHODS FOR THE PREPARATION THEREOF AND METHODS FOR THE USE THEREOF

FIELD OF THE INVENTION

The present invention relates to methods for the production of particulate vehicles for the intravenous administration of pharmacologically active agents, as well as novel compositions produced thereby. In a particular aspect, the invention relates to methods for the in vivo delivery of substantially water insoluble pharmacologically active agents (e.g., the anticancer drug Taxol®). In another aspect, dispersible colloidal systems containing water insoluble pharmacologically active agents are provided. The suspended particles may be formed of 100% active agent, or may be encased in a polymeric shell formulated from a biocompatible polymer, and have a diameter of less than about 1 micron. Invention colloidal systems may be prepared without the use of conventional surfactant or any polymeric core matrix. In a presently preferred aspect of the invention, there is provided a method for preparation of extremely small particles which can be sterile-filtered. The polymeric shell contains particles of pharmacologically active agent, and optionally a biocompatible dispersing agent in which pharmacologically active agent can be either dissolved or suspended. Thus, the invention provides a drug delivery system in either liquid form or in the form of a redispersible powder. Either form provides both immediately bioavailable drug molecules (i.e., drug molecules which are molecularly bound to a protein), and pure drug particles coated with a protein.

FIELD OF THE INVENTION

The invention also relates to the method of use and preparation of compositions (formulations) of drugs such as the anticancer agent paclitaxel. In one aspect, the formulation of paclitaxel, known as Capxol, is significantly less toxic and more efficacious than Taxol®, a commercially available formulation of paclitaxel. In another aspect, the novel formulation Capxol, localizes in certain tissues after parenteral administration thereby increasing the efficacy of treatment of cancers associated with such tissues.

BACKGROUND OF THE INVENTION

Intravenous drug delivery permits rapid and direct equilibration with the blood stream which carries the medication to the rest of the body. To avoid the peak serum levels which are achieved within a short time after intravascular injection, administration of drugs carried within stable carriers would allow gradual release of the drugs inside the intravascular compartment following a bolus intravenous injection of the therapeutic nanoparticles.

Injectable controlled-release nanoparticles can provide a pre-programmed duration of action, ranging from days to weeks to months from a single injection. They also can offer several profound advantages over conventionally administered medicaments, including automatic assured patient compliance with the dose regimen, as well as drug targeting to specific tissues or organs (Tice and Gilley, *Journal of Controlled Release* 2:343-352 (1985)).

Microparticles and foreign bodies present in the blood are generally cleared from the circulation by the "blood filtering organs", namely the spleen, lungs and liver. The particulate matter contained in normal whole blood comprises red blood cells (typically 8 microns in diameter), white blood cells (typically 6-8 microns in diameter), and platelets (typically 1-3 microns in diameter). The microcirculation in most organs and tissues allows the free passage of these blood cells. When microthrombii (blood clots) of size greater than 10-15 microns are present in circulation, a risk of infarction or blockage of the capillaries results, leading to ischemia or oxygen deprivation and possible tissue death. Injection into the circulation of particles greater than 10-15 microns in diameter, therefore, must be avoided. A suspension of particles less than 7-8 microns, is however, relatively safe and has been used for the delivery of pharmacologically active agents in the form of liposomes and emulsions, nutritional agents, and contrast media for imaging applications.

The size of particles and their mode of delivery determines their biological behavior. Strand et al. (in *Microspheres-Biomedical Applications*, ed. A. Rembaum, pp 193-227, CRC Press (1988)) have described the fate of particles to be dependent on their size. Particles in the size range of a few nanometers (nm) to 100 nm enter the lymphatic capillaries following interstitial injection, and phagocytosis may occur within the lymph nodes. After intravenous/intraarterial injection, particles less than about 2 microns will be rapidly cleared from the blood stream by the reticuloendothelial system (RES), also known as the mononuclear phagocyte system (MPS). Particles larger than about 7 microns will, after intravenous injection, be trapped in the lung capillaries. After intraarterial injection, particles are trapped in the first capillary bed reached. Inhaled particles are trapped by the alveolar macrophages.

Pharmaceuticals that are water-insoluble or poorly water-soluble and sensitive to acid environments in the stomach cannot be conventionally administered (e.g., by intravenous injection or oral administration). The parenteral administration of such pharmaceuticals has been achieved by emulsification of the oil solubilized drug with an aqueous liquid (such as normal saline) in the presence of surfactants or emulsion stabilizers to produce stable microemulsions. These emulsions may be injected intravenously, provided the components of the emulsion are pharmacologically inert. U.S. Pat. No. 4,073,943 describes the administration of water-insoluble pharmacologically active agents dissolved in oils and emulsified with water in the presence of surfactants such as egg phosphatides, pluronics (copolymers of polypropylene glycol and polyethylene glycol), polyglycerol oleate, etc. PCT International Publication No. WO85/00011 describes pharmaceutical microdroplets of an anaesthetic coated with a phospholipid such as dimyristoyl phosphatidylcholine having suitable dimensions for intradermal or intravenous injection.

An example of a water-insoluble drug is Taxol®, a natural product first isolated from the Pacific Yew tree, *Taxus brevifolia*, by Wani et al. (*J. Am. Chem. Soc.* 93:2325 (1971)). Among the antimitotic agents, Taxol, which contains a diterpene carbon skeleton, exhibits a unique mode of action on microtubule proteins responsible for the formation of the mitotic spindle. In contrast with other antimitotic agents such as vinblastine or colchicine, which prevent the assembly of tubulin, Taxol is the only plant product known to inhibit the depolymerization process of tubulin, thus preventing the cell replication process.

Taxol, a naturally occurring diterpenoid, has been shown to have significant antineoplastic and anticancer effects in drug-refractory ovarian cancer. Taxol has shown excellent antitumor activity in a wide variety of tumor models such as the B16 melanoma, L1210 leukemias, MX-1 mammary tumors, and CS-1 colon tumor xenografts. Several recent press releases have termed Taxol as the new anticancer wonder-drug. Indeed, Taxol has recently been approved by the Federal Drug Administration for treatment of ovarian cancer. The poor aqueous solubility of Taxol, however, presents a problem for human administration. Indeed, the delivery of drugs that are inherently insoluble or poorly soluble in an aqueous medium can be seriously impaired if oral delivery is not effective. Accordingly, currently used Taxol formulations require a cremaphor to solubilize the drug. The human clinical dose range is 200-500 mg. This dose is dissolved in a 1:1 solution of ethanol:cremaphor and diluted with saline of about 300-1000 ml of fluid given intravenously. The cremaphor currently used is polyethoxylated castor oil. The presence of cremaphor in this formulation has been linked to severe hypersensitivity reactions in animals (Lorenz et al., Agents Actions 1987, 7, 63-67) and humans (Weiss et al., J. Clin. Oncol. 1990, 8, 1263-68) and consequently requires premedication of patients with corticosteroids (dexamethasone) and antihistamines. The large dilution results in large volumes of infusion (typical dose 175 mg/m$^2$) up to 1 liter and infusion times ranging from 3 hours to 24 hours. Thus, there is a need for an alternative less toxic formulation for paclitaxel.

In phase I clinical trials, Taxol® itself did not show excessive toxic effects, but severe allergic reactions were caused by the emulsifiers employed to solubilize the drug. The current regimen of administration involves treatment of the patient with antihistamines and steroids prior to injection of the drug to reduce the allergic side effects of the cremaphor.

In an effort to improve the water solubility of Taxol, several investigators have modified its chemical structure with functional groups that impart enhanced water-solubility. Among them are the sulfonated derivatives (Kingston et al., U.S. Pat. No. 5,059,699 (1991)), and amino acid esters (Mathew et al., J. Med. Chem. 35:145-151 (1992)) which show significant biological activity. Modifications to produce a water-soluble derivative facilitate the intravenous delivery of Taxol dissolved in an innocuous carrier such as normal saline. Such modifications, however, add to the cost of drug preparation, may induce undesired side-reactions and/or allergic reactions, and/or may decrease the efficiency of the drug.

Protein microspheres have been reported in the literature as carriers of pharmacological or diagnostic agents. Microspheres of albumin have been prepared by either heat denaturation or chemical crosslinking. Heat denatured microspheres are produced from an emulsified mixture (e.g., albumin, the agent to be incorporated, and a suitable oil) at temperatures between 100° C. and 150° C. The microspheres are then washed with a suitable solvent and stored. Leucuta et al. (*International Journal of Pharmaceutics* 41:213-217 (1988)) describe the method of preparation of heat denatured microspheres.

The procedure for preparing chemically crosslinked microspheres involves treating the emulsion with glutaraldehyde to crosslink the protein, followed by washing and storage. Lee et al. (*Science* 213:233-235 (1981)) and U.S. Pat. No. 4,671,954 teach this method of preparation.

The above techniques for the preparation of protein microspheres as carriers of pharmacologically active agents, although suitable for the delivery of water-soluble agents, are incapable of entrapping water-insoluble ones. This limitation is inherent in the technique of preparation which relies on crosslinking or heat denaturation of the protein component in the aqueous phase of a water-in-oil emulsion. Any aqueous-soluble agent dissolved in the protein-containing aqueous phase may be entrapped within the resultant crosslinked or heat-denatured protein matrix, but a poorly aqueous-soluble or oil-soluble agent cannot be incorporated into a protein matrix formed by these techniques.

One conventional method for manufacturing drug-containing nanoparticles comprises dissolving polylactic acid (or other biocompatible, water insoluble polymers) in a water-immiscible solvent (such as methylene chloride or other chlorinated, aliphatic, or aromatic solvent), dissolving the pharmaceutically active agent in the polymer solution, adding a surfactant to the oil phase or the aqueous phase, forming an oil-in-water emulsion by suitable means, and evaporating the emulsion slowly under vacuum. If the oil droplets are sufficiently small and stable during evaporation, a suspension of the polymer in water is obtained. Since the drug is initially present in the polymer solution, it is possible to obtain by this method, a composition in which the drug molecules are entrapped within particles composed of a polymeric matrix. The formation of microspheres and nanoparticles by using the solvent evaporation method has been reported by several researchers (see, for example, Tice and Gilley, in *Journal of Controlled Release* 2:343-352 (1985); Bodmeier and McGinity, in *Int. J. Pharmaceutics* 43:179 (1988); Cavalier et al., in *J. Pharm. Pharmacol.* 38:249 (1985); and D'Souza et al., WO 94/10980) while using various drugs.

Bazile et. al., in *Biomaterials* 13:1093 (1992), and Spenlehauer et al., in Fr Patent 2 660 556, have reported the formation of nanoparticles by using two biocompatible polymers, one (e.g., polylactide) is dissolved in the organic phase, together with an active component such as a drug, and the other polymer, such as albumin, is used as the surface active agent. After emulsification and removal of the solvent; nanoparticles are formed, in which the drug is present inside the polymeric matrix of the polylactide particles.

The properties of the polymer solution from which the polymeric matrix is formed are very important to obtain the proper emulsion in the first stage. For example, polylactide (the polymer commonly used in the preparation of injectable nanoparticles), has a surface activity which causes the rapid adsorption thereof at the dichloromethane-water interface, causing reduced interfacial tension (see, for example, Boury et al., in *Langmuir* 11:1636 (1995)), which in turn improves the emulsification process. In addition, the same researchers found that Bovine Serum Albumin (BSA) interacts with the polylactide, and penetrates into the polylactide monolayer present at the oil-water interface. Therefore, it is expected, based on the above reference, that emulsification during the conventional solvent evaporation method is greatly favored by the presence of the surface active polymer (polylactide) in the nonaqueous organic phase. In fact, the presence of polylactide is not only a sufficient condition, but it is actually necessary for the formation of nanoparticles of suitable size.

Another process which is based on the solvent evaporation method comprises dissolving the drug in a hydrophobic solvent (e.g., toluene or cyclohexane), without any polymer dissolved in the organic solvent, adding a conventional surfactant to the mixture as an emulsifier, forming an oil-in-water emulsion by use of sonication on high-shear equipment, and then evaporating the solvent to obtain dry particles of the drug (see, for example, Sjostrom et al., in *J. Dispersion Science and Technology* 15:89-117 (1994)). Upon removal of the nonpolar solvent, precipitation of the drug inside the solvent droplets occurs, and submicron particles are obtained.

It has been found that the size of the particles is mainly controlled by the initial size of the emulsion droplets. In addition, it is interesting to note that the final particle size is reported to decrease with a decrease in the drug concentration in the organic phase. This finding is contrary to the results reported herein, wherein no conventional surfactant is used for the preparation of nanoparticles (in same embodiments of the invention). In addition, it is noted by the authors of the Sjostrom paper that the drug used, cholesteryl acetate, is surface active in toluene, and hence may be oriented at the oil-water interface; therefore the concentration of drug at the interface is higher, thus increasing the potential for precipitation.

Formation of submicron particles has also been achieved by a precipitation process, as described by Calvo et al. in *J. Pharm. Sci.* 85:530 (1996). The process is based on dissolving the drug (e.g., indomethacin) and the polymer (polycaprolactone) in methylene chloride and acetone, and then pouring the solution into an aqueous phase containing a surfactant (Poloxamer 188), to yield submicron size particles (216 nm). However, the process is performed at solvent concentrations at which no emulsion is formed.

BACKGROUND OF THE INVENTION

Taxol is a naturally occurring compound which has shown great promise as an anti-cancer drug. For example, Taxol has been found to be an active agent against drug-refractory ovarian cancer by McGuire et al. See "Taxol: A Unique Anti-Neoplastic Agent With Significant Activity Against Advanced Ovarian Epithelial Neoplasms." Ann. Int. Med., 111, 273-279 (1989). All patents, scientific articles, and other documents mentioned herein are incorporated by reference as if reproduced in full below.

Unfortunately, Taxol has extremely low solubility in water, which makes it difficult to provide a suitable dosage form. In fact, in Phase I clinical trials, severe allergic reactions were caused by the emulsifiers administered in conjunction with Taxol to compensate for Taxol's low water solubility; at least one patient's death was caused by an allergic reaction induced by the emulsifiers. Dose limiting toxicities include neutropenia, peripheral neuropathy, and hypersensitivity reactions.

Brown et al., in "A Phase I Trial of Taxol Given by A 6-Hour Intravenous Infusion" J of Clin Oncol, Vol. 9 No. 7, pp. 1261-1267 (July 1991) report on a Phase I Trial in which Taxol was provided as a 6-hour IV infusion every 21 days without premedication. 31 patients received 64 assessable courses of Taxol. One patient had a severe (or acute) hypersensitivity reaction, which required discontinuation of the infusion and immediate treatment to save the patient's life. Another patient experienced a hypersensitivity reaction, but it was not so severe as to require discontinuing the infusion. Myelosuppression was dose-limiting, with 2 fatalities due to sepsis. Non-hematologic toxicity was of Grade 1 and 2, except for one patient with Grade 3 mucositis and 2 patients with Grade 3 neuropathy. The neuropathy consisted of reversible painful paresthesias, requiring discontinuation of Taxol in two patients. Four partial responses were seen (3 in patients with non-small-cell lung cancer, and one in a patient with adenocarcinoma of unknown primary). The maximum tolerated dose reported was 275 mg/m2, and the recommended Phase II starting dose was 225 mg/m2. The incidence of hypersensitivity reaction was reported to be schedule-dependent, with 6 to 24-hour infusions of drug having a 0% to 8% incidence of hypersensitivity reactions. It was also reported that hypersensitivity reactions persist with or without premedication despite prolongation of infusion times. Since these Phase I studies were conducted on terminally ill patients suffering from a variety of cancers, the efficacy of the Taxol treatments could not be determined.

In a study by Kris et al., Taxol formulated with Cremaphor EL in dehydrated alcohol was given as a 3-hour IV infusion every 21 days, with the administered dosage ranging from 15 to 230 mg/m2 in nine escalation steps. Kris et al. concluded that "with the severity and unpredictability of the hypersensitivity reactions, further usage of Taxol is not indicated with this drug formulation on this administration schedule." See Cancer Treat. Rep., Vol. 70, No. 5, May 1986.

Since early trials using a bolus injection or short (1-3 hour) infusions induced anaphylactic reactions or other hypersensitivity responses, further studies were carried out in which Taxol was administered only after premedication with steroids (such as dexamethasone), antihistamines (such as diphenhydramine), and H2-antagonists (such as cimetidine or ranitidine), and the infusion time was extended to 24 hours in an attempt to eliminate the most serious allergic reactions. Various Phase I and Phase II study results have been published utilizing 24-hour infusions of Taxol with maximum total dosages of 250 mg/m2, generally with the course being repeated every 3 weeks. Patients were pre-treated with dexamethasone, diphenhydramine, and cimetidine to offset allergic reactions. See Einzig, et al., "Phase II Trial of Taxol in Patients with Metastatic Renal Cell Carcinoma," Cancer-Investigation, 9(2) 133-136 (1991), and A. B. Miller et al., "Reporting Results of Cancer Treatment," Cancer, Vol 47, 207-214 (1981).

Koeller et al., in "A Phase I Pharmacokinetic Study of Taxol Given By a Prolonged Infusion Without Premedication," Proceedings of ASCO, Vol. 8 (March, 1989), recommends routine premedication in order to avoid the significant number of allergic reactions believed to be caused by the cremophor (polyethoxylated castor oil) vehicle used for Taxol infusions. Patients received dosages ranging from 175 mg/m2 to 275 mg/m2.

Wiernik et al. in "Phase I Clinical and Pharmacokinetic Study of Taxol," Cancer Research, 47, 2486-2493 (May 1, 1987), also report the administration of Taxol in a cremophor vehicle by IV infusion over a 6-hour period in a Phase I study. Grade 3-4 hypersensitivity reactions incurred in 4 of 13 courses. The starting dose for the study was 15 mg/m2 (one-third of the lowest toxic dose in dogs). Doses were escalated, and a minimum of 3 patients were treated at each dose level until toxicity was identified, and then 4-6 patients were treated at each subsequent level. The study concluded that neurotoxicity and leukopenia were dose-limiting, and the recommended Phase II trial dose was 250 mg/m2 with premedication.

Other exemplary studies on Taxol include: Legha et al., "Phase II Trial of Taxol in Metastatic Melanoma," Vol. 65 (June 1990) pp. 2478-2481; Rowinsky et al., "Phase I and Pharmacodynamic Study of Taxol in Refractory Acute Leukemias," Cancer Research, 49, 4640-4647 (Aug. 15, 1989); Grem et al., "Phase I Study of Taxol Administered as a Short IV Infusion Daily For 5 Days," Cancer Treatment Reports, Vol. 71 No. 12, (December, 1987); Donehower et al., "Phase I Trial of Taxol in Patients With Advanced Cancer," Cancer Treatment Reports, Vol. 71, No. 12, (December, 1987); Holmes et al., "Phase II Study of Taxol in Patients (PT) with Metastatic-Breast Cancer (MBC)," Proceedings of the American Society of Clinical Oncology, Vol. 10, (March, 1991), pp. 60. See also Suffness. "Development of Antitumor Natural Products at the National Cancer Institute," Gann Monograph or Cancer Research, 31 (1989) pp. 21-44 (which recommends that Taxol only be given as a 24-hour infusion).

Weiss et al., in "Hypersensitivity Reactions from Taxol," Journal of Clinical Oncology, Vol. 8, No. 7 (July 1990) pp. 1263-1268, reported that it was difficult to determine a reliable overall incidence of hypersensitivity reactions, HSRs, because of the wide variations in Taxol doses and schedules used, and the unknown degree of influence that changing the infusion schedule and using premedication has on HSR incidents. For example, of five patients who received Taxol in a 3-hour infusion at greater than 190 mg/m2 with no premedication, three had reactions, while only one out of 30 patients administered even higher doses over a 6-hour infusion with no premedication had a reaction. Therefore, this suggests that prolonging the infusion to beyond 6 hours is sufficient to reduce HSR incidents. Nevertheless, Weiss et al. found that patients receiving 250 mg/m2 of Taxol administered via a 24-hour infusion still had definite HSRs. Thus, while prolonging drug infusion to 6 or 24-hours may reduce the risk for an acute reaction, this conclusion can not be confirmed, since 78% of the HSR reactions occurred within ten minutes of initiating the Taxol infusion, which indicates that the length of time planned for the total infusion would have no bearing. Further, concentration of Taxol in the infusion may also not make a difference since substantial numbers of patients had reactions to various small Taxol dosages. Finally, not only is the mechanism of Taxol HSR unknown, it is also not clear whether Taxol itself is inducing HSRS, or if the HSRs are due to the excipient (Cremaphor EL; Badische Anilin und Soda Fabrik AG [BASF], Ludwigshafen, Federal Republic of Germany). Despite the uncertainty as to whether or not premedication had any influence on reducing the severity or number of HSRs, prophylactic therapy was recommended, since there is no known danger from its use.

The conflicting recommendations in the prior art concerning whether premedication should be used to avoid hypersensitivity reactions when using prolonged infusion durations, and the lack of efficacy data for infusions done over a six-hour period has led to the use of a 24-hour infusion of high doses (above 170 mg/m2) of Taxol in a Cremaphor EL emulsion as an accepted cancer treatment protocol.

Although it appears possible to minimize the side effects of administering Taxol in an emulsion by use of a long infusion duration, the long infusion duration is inconvenient for patients, and is expensive due to the need to monitor the patients for the entire 6 to 24-hour infusion duration. Further, the long infusion duration requires that patients spend at least one night in a hospital or treatment clinic.

Higher doses of paclitaxel have also been described in the literature. To determine the maximal-tolerated dose (MTD) of paclitaxel in combination with high-dose cyclophosphamide and cisplatin followed by autologous hematopoietic progenitor-cell support (AHPCS), Stemmer et al (Stemmer S M, Cagnoni P J, Shpall E J, et al: High-dose paclitaxel, cyclophosphamide, and cisplatin with autologous hematopoietic progenitor-cell support: A phase I trial. J Clin Oncol 14:1463-1472, 1996) have conducted a phase I trial in forty-nine patients with poor-prognosis breast cancer, non-Hodgkin's lymphoma (NHL) or ovarian cancer with escalating doses of paclitaxel infused over 24 hours, followed by cyclophosphamide (5,625 mg/m$^2$) and cisplatin (165 mg/m$^2$) and AHPCS. Dose-limiting toxicity was encountered in two patients at 825 mg/m$^2$ of paclitaxel; one patient died of multi-organ failure and the other developed grade 3 respiratory, CNS, and renal toxicity, which resolved. Grade 3 polyneuropathy and grade 4 CNS toxicity were also observed. The MTD of this combination was determined to be paclitaxel (775 mg/m$^2$), cyclophosphamide (5,625 mg/m$^2$), and cisplatin (165 mg/m$^2$) followed by AHPCS. Sensory polyneuropathy and mucositis were prominent toxicities, but both were reversible and tolerable. Eighteen of 33 patients (54%) with breast cancer achieved a partial response. Responses were also observed in patients with NHL (four of five patients) and ovarian cancer (two of two patients).

U.S. Pat. No. 5,641,803 reports the use of Taxol at doses 175 and 135 mg/m2 administered in a 3 hour infusion. The infusion protocols require the use premedication and reports the incidences of hypersensitivity reactions in 35% of the patients. Neurotoxicity was reported in 51% of patients with 66% of patients experiencing neurotoxicity in the high dose group and 37% in the low dose group. Furthermore, it was noted that 48% of patients experienced neurotoxicity for longer infusion times of 24 hours while 54% of patients experienced neurotoxicity for the shorter 3 hour infusion.

There is evidence in the literature that higher doses of paclitaxel result in a higher response rate. The optimal doses and schedules for paclitaxel are still under investigation. To assess the possibility that paclitaxel dose intensity may be important in the induction of disease response, Reed et al of NCI (Reed E, Bitton R, Sarosy G, Kohn E: Paclitaxel dose intensity. Journal of Infusional Chemotherapy 6:59-63, 1996) analyzed the available phase II trial data in the treatment of ovarian cancer and breast cancer. Their results suggest that the relationship between objective disease response and paclitaxel dose intensity in recurrent ovarian cancer is highly statistically significant with two-side p value of 0.022. The relationship in breast cancer is even stronger, with a two-sided p value of 0.004. At 135 mg/m$^2$/21 days, the objective response rate was 13.2%; and at 250 mg/m$^2$/21 days, the objective response rate was 35.9%. The response rate seen at the intermediate dose of 175 mg/m$^2$ was linear with the 135 mg/m$^2$ and 250 mg/m$^2$ results and the linear regression analysis shows a correlation coefficient for these data of 0.946 (Reed et al, 1996).

In a study by Holmes (Holmes F A, Walters R S, Theriault R L, et al: Phase II trial of Taxol, an active drug in the treatment of metastatic breast cancer. J Natl Cancer Inst 83:1797-1805, 1991), and at MSKCC (Reichman B S, Seidman A D, Crown J P A, et al: Paclitaxel and recombinant human granulocyte colony-stimulating factor as initial chemotherapy for metastatic breast cancer. J Clin Oncol 11:1943-1951, 1993), it was shown that higher doses of TAXOL up to 250 mg/m$^2$ produced greater responses (60%) than the 175 mg/m$^2$ dose (26%) currently approved for TAXOL. These results however, have not been reproduced due to higher toxicity at these higher doses. These studies, however, bear proof to the potential increase in response rate at increased doses of paclitaxel.

Since premedication is required for Taxol, that often necessitates overnight stays of the patient at the hospital, it is highly desirable to develop a formulation of paclitaxel that obviates the need for premedication.

Since premedication is required for Taxol, due to HSR's associated with administration of the drug, it is highly desirable to develop a formulation of paclitaxel that does not cause hypersensitivity reactions. It is also desirable to develop a formulation of paclitaxel that does not cause neurotoxicity.

Since Taxol infusions are generally preceded by remedication, and require post-infusion monitoring and record keeping, that often necessitates overnight stays of the patient at the hospital, it is highly desirable to develop a formulation of paclitaxel which would allow for recipients to be treated on an out-patient basis.

Since it has been demonstrated that higher doses of Taxol achieve improved clinical responses albeit with higher toxicity, it is desirable to develop a formulation of paclitaxel which can achieve these doses without this toxicity.

Since it has been demonstrated that the dose limiting toxicity of Taxol is cerebral and neurotoxicity, it is desirable to develop a formulation of paclitaxel that decreases such toxicity.

It is also desirable to eliminate premedication since this increases patient discomfort and increases the expense and duration of treatment.

It is also desirable to shorten the duration of infusion of Taxol, currently administered in 3 hours-24 hours to minimize patient stay at the hospital or clinic.

Since Taxol is currently approved for administration at concentrations between 0.6-1.2 mg/ml and a typical dose in humans is about 250-350 mg, this results in infusion volumes typically greater than 300 ml. It is desirable to reduce these infusion volumes, by developing formulations of paclitaxel that are stable at higher concentrations so as to reduce the time of administration.

Since infusion of Taxol is limited to the use of special I.V. tubing and bags or bottles due to the leaching of plasticizers by the cremaphor in the Taxol formulaton, it is desirable to develop a formulation of paclitaxel that does not have cremaphor and does not leach potentially toxic materials from the conventionally used plastic tubings or bags used for intravenous infusion.

BRIEF DESCRIPTION OF THE INVENTION

Thus it is an object of this invention to deliver pharmacologically active agents (e.g., Taxol, taxane, Taxotere, and the like) in unmodified form in a composition that does not cause allergic reactions due to:the presence of added emulsifiers and solubilizing agents, as are currently employed in drug delivery.

It is a further object of the present invention to deliver pharmacologically active agents in a composition of microparticles or nanoparticles, optionally suspended in a suitable biocompatible liquid.

It is yet another object of the present invention to provide methods for the formation of submicron particles (nanoparticles) of pharmacologically active agents by a solvent evaporation technique from an oil-in-water emulsion. Some methods use proteins as stabilizing agents. Some methods are performed in the absence of any conventional surfactants, and in the absence of any polymeric core material.

These and other objects of the invention will become apparent upon review of the specification and claims.

In accordance with the present invention, we have discovered that substantially water insoluble pharmacologically active agents can be delivered in the form of microparticles or nanoparticles that are suitable for parenteral administration in aqueous suspension. This mode of delivery obviates the necessity for administration of substantially water insoluble harmacologically active agents (e.g., Taxol) in an emulsion containing, for example, ethanol and polyethoxylated castor oil, diluted in normal saline (see, for example, Norton et al., in *Abstracts of the 2nd National Cancer Institute Workshop on Taxol & Taxus*, Sep. 23-24, 1992). A disadvantage of such known compositions is their propensity to produce allergic side effects.

Thus, in accordance with the present invention, there are provided methods for the formation of nanoparticles of pharmacologically active agents by a solvent evaporation technique from an oil-in-water emulsion prepared under a variety of conditions. For example, high shear forces (e.g., sonication, high pressure homogenization, or the like) may be used in the absence of any conventional surfactants, and without the use of any polymeric core material to form the matrix of the nanoparticle. Instead, proteins (e.g., human serum albumin) are employed as a stabilizing agent. In an alternative method, nanoparticles may be formed without the need for any high shear forces, simply by selecting materials that spontaneously form microemulsions.

The invention further provides a method for the reproducible formation of unusually small nanoparticles (less than 200 nm diameter), which can be sterile-filtered through a 0.22 micron filter. This is achieved by addition of a water soluble solvent (e.g. ethanol) to the organic phase and by carefully selecting the type of organic phase, the phase fraction and the drug concentration in the organic phase. The ability to form nanoparticles of a size that is filterable by 0.22 micron filters is of great importance and significance, since formulations which contain a significant amount of any protein (e.g., albumin), cannot be sterilized by conventional methods such as autoclaving, due to the heat coagulation of the protein.

In accordance with another embodiment of the present invention, we have developed compositions useful for in vivo delivery of substantially water insoluble pharmacologically active agents. Invention compositions comprise substantially water insoluble pharmacologically active agents (as a solid or liquid) contained within a polymeric shell. The polymeric shell is a crosslinked biocompatible polymer. The polymeric shell, containing substantially water insoluble pharmacologically active agents therein, can then be suspended in a biocompatible aqueous liquid for administration.

The invention further provides a drug delivery system in which part of the molecules of pharmacologically active agent are bound to the protein. (e.g., human serum albumin), and are therefore immediately bioavailable upon administration to a mammal. The other portion of the pharmacologically active agent is contained within nanoparticles coated by protein. The nanoparticles containing the pharmacologically active agent are present as a pure active component, without dilution by any polymeric matrix.

A large number of conventional pharmacologically active agents circulate in the blood stream bound to carrier proteins (through hydrophobic or ionic interactions) of which the most common example is serum albumin. Invention methods and compositions produced thereby provide for a pharmacologically active agent that is "pre-bound" to a protein (through hydrophobic or ionic interactions) prior to administration.

The present disclosure demonstrates both of the above-described modes of bioavailability for Taxol (Paclitaxel), an anticancer drug capable of binding to human serum albumin (see, for example, Kumar et al., in *Research Communications in Chemical Pathology and Pharmacology* 80:337 (1993)). The high concentration of albumin in invention particles, compared to Taxol, provides a significant amount of the drug in the form of molecules bound to albumin, which is also the natural carrier of the drug in the blood stream.

In addition, advantage is taken of the capability of human serum albumin to bind Taxol, as well as other drugs, which enhances the capability of Taxol to absorb on the surface of the particles. Since albumin is present on the colloidal drug particles (formed upon removal of the organic solvent), formation of a colloidal dispersion which is stable for prolonged periods is facilitated, due to a combination of electrical repulsion and steric stabilization.

In accordance with the present invention, there are also provided submicron particles in powder form, which can easily be reconstituted in water or saline. The powder is obtained after removal of water by lyophilization. Human serum albumin serves as the structural component of some invention nanoparticles, and also as a cryoprotectant and reconstitution aid. The preparation of particles filterable through a 0.22 micron filter according to the invention method as described herein, followed by drying or lyophilization, produces a sterile solid formulation useful for intravenous injection.

The invention provides, in a particular aspect, a composition of anti-cancer drugs, e.g., Taxol, in the form of nanoparticles in a liquid dispersion or as a solid which can be easily reconstituted for administration. Due to specific properties of certain drugs, e.g., Taxol, such compositions can not be obtained by conventional solvent evaporation methods that rely on the use of surfactants. In the presence of various surfactants, very large drug crystals (e.g., size of about 5 microns to several hundred microns) are formed within a few minutes of storage, after the preparation process. The size of such crystals is typically much greater than the allowed size for intravenous injection.

While it is recognized that particles produced according to the invention can be either crystalline, amorphous, or a mixture thereof, it is generally preferred that the drug be present in the formulation in an amorphous form. This would lead to greater ease of dissolution and absorption, resulting in better bioavailability.

BRIEF DESCRIPTION OF THE INVENTION

The anticancer agent paclitaxel (TAXOL, Bristol Myers Squibb, BMS,) has remarkable clinical activity in a number of human cancers including cancers of the ovary, breast, lung, esophagus, head and neck region, bladder and lymphomas. It is currently approved for the treatment of ovarian carcinoma where it is used in combination with cisplatin and for metastatic breast cancer that has failed prior treatment with one combination chemotherapy regimen. The major limitation of Taxol is its poor solubility and consequently the BMS formulation contains 50% Cremaphor EL and 50% ethanol as the solubilizing vehicle. Each vial of this formulation contains 30 mg of paclitaxel dissolved at a concentration of 6 mg/ml. Prior to intravenous administration, this formulation must be diluted 1:10 in saline for a final dosing solution containing 0.6 mg/ml of paclitaxel. This formulation has been linked to severe hypersensitivity reactions in animals (Lorenz et al., Agents Actions 1987, 7, 63-67) and humans (Weiss et al., J. Clin. Oncol. 1990, 8, 1263-68) and consequently requires premedication of patients with corticosteroids (dexamethasone) and antihistamines. The large dilution results in large volumes of infusion (typical dose 175 mg/m$^2$) upto 1 liter and infusion times ranging from 3 hours to 24 hours. Thus, there is a need for an alternative less toxic formulation for paclitaxel.

Capxol™ is a novel, cremophor-free formulation of the anticancer drug paclitaxel. The inventors, based on animal studies, believe that a cremophor-free formulation will be significantly less toxic and will not require premedication of patients. Premedication is necessary to reduce the hypersensitivity and anaphylaxis that occurs as a result of cremophor in the currently approved and marketed BMS (Bristol Myers Squibb) formulation of paclitaxel. Capxol™ is a lyophilized powder for reconstitution and intravenous administration. When reconstituted with a suitable aqueous medium such as 0.9% sodium chloride injection or 5% dextrose injection, Capxol™ forms a stable colloidal solution of paclitaxel. The size of the colloidal suspension may range from 20 nm to 8 microns with a preferred range of about 20-400 nm. The two major components of Capxol™ are unmodified paclitaxel and human serum albumin (HSA). Since HSA is freely soluble in water, Capxol™ can be reconstituted to any desired concentration of paclitaxel limited only by the solubility limits for HSA. Thus Capxol™ can be reconstituted in a wide range of concentrations ranging from dilute (0.1 mg/ml aclitaxel) to concentrated (20 mg/ml paclitaxel). This can result in fairly small volumes of administration.

In accordance with the present invention, there are provided compositions and methods useful for in vivo delivery of biologics, in the form of nanoparticles that are suitable for parenteral administration in aqueous suspension. Invention compositions comprise stabilized by a polymer. The polymer is a biocompatible material, such as the protein albumin. Use of invention compositions for the delivery of biologics obviates the necessity for administration of biologics in toxic diluents of vehicles, for example, ethanol and polyethoxylated castor oil, diluted in normal saline (see, for example, Norton et al., in Abstracts of the 2nd National Cancer Institute Workshop on Taxol & Taxus, September 23-24, 1992). A disadvantage of such known compositions is their propensity to produce severe allergic and other side effects.

It is known that the delivery of biologics in the form of a particulate suspension allows targeting to organs such as the liver, lungs, spleen, lymphatic circulation, and the like, due to the uptake in these organs, of the particles by the reticuloendothelial (RES) system of cells. Targeting to the RES containing organs may be controlled through the use of particles of varying size, and through administration by different routes. But when administered to rats, Capxol was unexpectedly and surprisingly found to accumulate in tissues other than those containing the RES such as the prostate, pancreas, testes, seminiferous tubules, bone, etc. to a significantly greater level than Taxol at similar doses.

Thus, it is very surprising that the invention formulation of paclitaxel, Capxol, a nanoparticle formulation, concentrates in tissues such as the prostate, pancreas, testes, seminiferous tubules, bone, etc., i.e., in organs not containing the RES, at a significantly higher level than a non-particulate formulation of paclitaxel such as Taxol. Thus, Capxol may be utilized to treat cancers of these tissues with a higher efficacy than Taxol. However, the distribution to many other tissues is similar for Capxol and Taxol, therefore Capxol is expected to maintain anticancer activity at least equal to that of TAXOL in other tissues.

The basis for the localization within the prostate could be a result of the particle size of the formulation (2.0-400 nm), or the presence the protein albumin in the formulation which may cause localization into the prostatic tissue through specific membrane receptors (gp 60, gp 18, gp 13 and the like). It is also likely that other biocompatible, biodegradable polymers other than albumin may show specificity to certain tissues such as the prostate resulting in high local concentration of paclitaxel in these tissues as a result of the properties described above. Such biocompatible materials are contemplated within the scope of this invention. A preferred embodiment of a composition to achieve high local concentrations of paclitaxel in the prostate is a formulation containing paclitaxel and albumin with a particle size in the range of 20-400 nm, and free of cremophor. This embodiment has also been demonstrated to result in higher level concentrations of paclitaxel in the, pancreas, kidney, lung, heart, bone, and spleen when compared to Taxol at equivalent doses. These properties provide novel applications of this formulation of paclitaxel including methods of lowering testosterone levels, achieving medical orchiectomy, providing high local concentrations to coronary vasculature for the treatment of restenosis.

It is also very surprising that paclitaxel is metabolized into its metabolites at a much slower rate than Taxol when administered as Capxol. This represents increased anticancer activity for longer periods with similar doses of paclitaxel.

It is also very surprising that when Capxol and Taxol are administered to rats at equivalent doses of paclitaxel, a much higher degree of myelosuppression results for the Taxol group compared to the Capxol group. This can result in lower incidences of infections and fever episodes (e.g., febrile neutropenia). It can also reduce the cycle time in between treatments which is currently 21 days. Thus the use of Capxol may provide substantial advantage over Taxol.

It was surprisingly found that the Taxol vehicle, Cremophor/Ethanol diluted in saline, alone caused strong myelosuppression and caused severe hypersensitivity reactions and death in several dose groups of mice. No such reactions were observed for the Capxol groups at equivalent and higher doses. Thus Capxol, a formulation of paclitaxel that is free of the Taxol vehicle is of substantial advantage.

It is also very surprising that when Capxol and Taxol are administered to rats at equivalent doses of paclitaxel, a much lower toxicity is seen for the Capxol compared to Taxol as evidenced by significantly higher LD50 values. This may allow for higher more therapeutically effective doses of paclitaxel to be administered to patients. There is evidence in the literature showing increases response rates to higher doses of paclitaxel. The Capxol formulation may allow the administration of these higher doses due to lower toxicity and thereby exploit the full potential of this drug.

It is also surprising that Capxol, a formulation of the substantially water-insoluble drug, paclitaxel, is stable when reconstituted in an aqueous medium at several different concentrations ranging from, but not limited to 0.1-20 mg/ml. This offers substantial advantage over Taxol during administration of the drug as it results in smaller infusion olumes, overcomes instability issues known for Taxol, such as recipitation, and avoids the use of an in-line filter in the infusion line. Thus Capxol greatly simplifies and improves the administration of paclitaxel to patients.

It is also surprising that Capxol when administered to rats at equivalent doses of paclitaxel as Taxol, shows no sign of neurotoxicity while Taxol even at low doses shows neurotoxic effects.

The invention formulation further allows the administration of paclitaxel, and other substantially water insoluble pharmacologically active agents, employing a much smaller volume of liquid and requiring greatly reduced administration time relative to administration volumes and times required by prior art delivery systems.

In combination with a biocompatible polymer matrix, the invention formulation (Capxol) allows for local sustained delivery of paclitaxel with lower toxicity and prolonged activity.

The above surprising findings for Capxol offer the potential to substantially improve the quality of life of patients receiving paclitaxel.

Potential Advantages of the Capxol™ Formulation for Paclitaxel:

Capxol™ is a lyophilized powder containing only paclitaxel and human serum albumin. Due to the nature of the colloidal solution formed upon reconstitution of the lyophilized powder toxic emulsifiers such as cremophor (in the BMS formulation of paclitaxel) or polysorbate 80 (as in the Rhone Poulenc formulation of docetaxel) and solvents such as ethanol to solubilize the drug are not required. Removing toxic emulsifers will reduce the incidences of severe hypersensitivity and anaphylactic reactions that are known to occur in products TAXOL.
In addition, no premedication with steroids and antihistamines are anticipated prior to administration of the drug.

Due to reduced toxicities, as evidenced by the $LD_{10}/LD_{50}$ studies, higher doses may be employed for greater efficacy.

The reduction in myelosuppression (as compared with the BMS formulation) is expected to reduce the period of the treatment cycle (currently 3 weeks) and improve the therapeutic outcomes.

Capxol™ can be administered at much higher concentrations (upto 20 mg/ml) compared with the BMS formulation (0.6 mg/ml), allowing much lower volume infusions, and administration as an intravenous bolus.

TAXOL may be infused only with nitroglycerin polyolefin infusion sets due to leaching of plasticizers from standard infusion tubing into the formulation. Capxol shows no leaching and may be utilized with any standard infusion tubing. In addition, only glass or polyolefin containers are to be used for storing all cremophor containing solutions. The Capxol formulation has no such limitations.

A recognized problem with TAXOL formulation is the precipitation of paclitaxel in indwelling catheters. This results in erratic and poorly controlled dosing. Due to the inherent stability of the colloidal solution of the new formulation, Capxol™, the problem of precipitation is alleviated.

The administration of Taxol requires the use of in line filters to remove precipitates and other particulate matter. Capxol has no such requirement due to inherent stability.

The literature suggests that particles in the low hundred nanometer size range preferentially partition into tumors through leaky blood vessels at the tumor site. The colloidal particles of paclitaxel in the Capxol™ formulation may therefore show a preferential targeting effect, greatly reducing the side effects of paclitaxel administered in the BMS formulation.

Therefore, it is a primary object of the present invention to provide a new formulation of paclitaxel that provides the above desirable characteristics.

It is another object of the present invention to provide a new formulation of paclitaxel that localizes paclitaxel in certain tissues, thereby providing higher anticancer activity at these sites.

It is another object of the invention to administer paclitaxel at concentrations greater than about 2 mg/ml in order to reduce infusion volumes.

It is also an object of the invention to provide a formulation of paclitaxel that is free of the Taxol vehicle.

It is yet another object of the invention to provide a formulation of paclitaxel that improves the quality of life of patients receiving Taxol for the treatment of cancer.

DETAILED DESCRIPTION OF THE INVENTION

Figure 1:
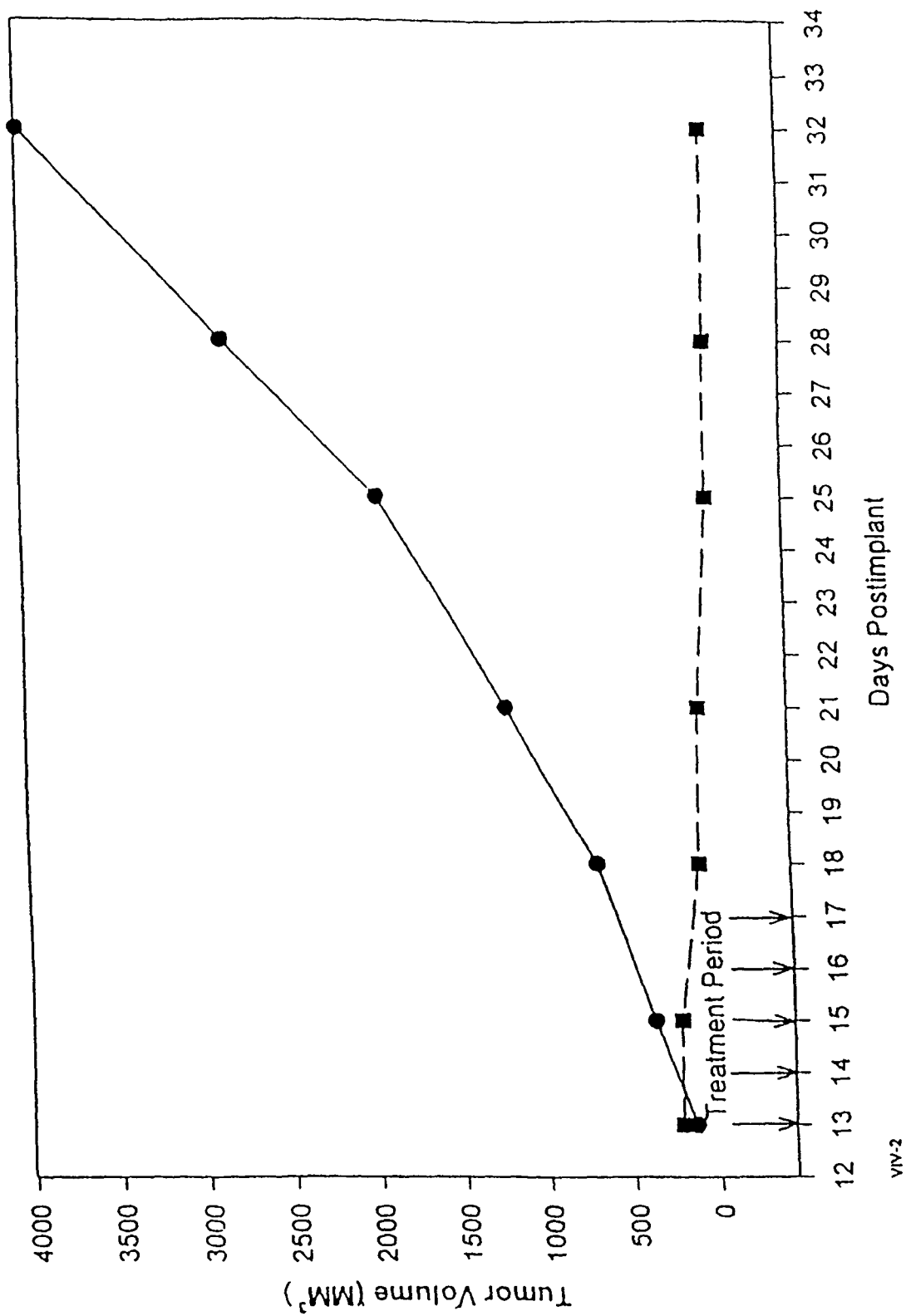
FIG. 1 presents the results of intravenous administration of paclitaxel nanoparticles to tumor bearing mice (n=5 in each group), showing a complete regression of tumor in the treatment group (■) compared with a control group receiving saline (●). Virtually uncontrolled tumor growth is seen in the control group. Dose for the treatment group is 20 mg/kg of paclitaxel administered as an intravenous bolus for five consecutive days.

In accordance with the present invention, there are provided methods for reducing the hematologic toxicity of paclitaxel in a subject undergoing treatment with paclitaxel, said method comprising systemically administering said paclitaxel to said subject in a pharmaceutically acceptable formulation at a does of at least 175 mg/m² over an administration period of no greater than two hours.

[[also parrot other independent claims]]

In accordance with the present invention, there are also provided methods for the preparation of substantially water insoluble pharmacologically active agents for in vivo delivery, said method comprising:
 a) combining
  i) an organic solvent having said active agent dissolved therein;
  ii) water or an aqueous solution;
  iii) a surfactant; and
  iv) a cosurfactant that spontaneously form a microemulsion; and
 b) removing said organic solvent to yield a suspension of nanoparticles of said active agent in said water.

In accordance with a still further embodiment of the present invention, there is provided a drug delivery system comprising particles of a solid or liquid, substantially water insoluble pharmacologically active agent, coated with a protein,
 wherein said protein coating has free protein associated therewith,
 wherein a portion of said pharmacologically active agent is contained within said protein coating and a portion of said pharmacologically active agent is associated with said free protein, and
 wherein the average diameter of said particles is no greater than about 1 micron.

Compositions produced by the above-described methods are particularly advantageous as they have been observed to provide a very low toxicity form of a variety of pharmacologically active agents. Also described herein are other methods of making low toxicity forms of pharmacologically active agents, e.g., paclitaxel.

In a preferred embodiment, the average diameter of the above-described particles is no greater than about 200 nm. Such particles are particularly advantageous as they can be subjected to sterile filtration, thereby obviating the need for more vigorous treatment to achieve sterilization of solutions containing the desired pharmacologically active agent.

As used herein, unless specified to the contrary, the term "paclitaxel" encompasses all forms, modifications and derivatives of paclitaxel, e.g., taxotere, and the like.

Capxol™ is the trademark for the paclitaxel formulation to be marketed by Applicants' assignees. As used herein, Capxol™ is merely a shorthand means of reference to protein-coated paclitaxel nanoparticles produced by the method of Example 1. Capxol™ is a proprietary new, cremaphor-free formulation of the anticancer drug paclitaxel. Inventors, based on animal studies, believe that a cremaphor-free formulation will be significantly less toxic and will not require premedication of patients. Premedication is necessary to reduce the hypersensitivity and anaphylaxis that occurs as a result of cremaphor in the currently approved and marketed BMS (Bristol Myers Squibb) formulation of paclitaxel. Capxol™ is a lyophilized powder for reconstitution and intravenous administration. Each vial of Capxol™ contains 30 mg of paclitaxel and approximately 400 mg of human serum albumin. When reconstituted with a suitable aqueous medium such as 0.9% sodium chloride injection or 5% dextrose injection, Capxol™ forms a stable colloidal solution of paclitaxel. The size of the colloidal nanoparticles is typically less than 400 nm. The nanoparticles are prepared by high pressure homogenization of a solution of USP human serum albumin and a solution of paclitaxel in an organic solvent. The solvent is then removed to generate the colloidal suspension or solution of paclitaxel in human albumin. This suspension is sterile filtered and lyophilized to obtain Capxol™. The formulation contains no other added excipients or stabilizers. The sterility of the product is assured by an aseptic manufacturing process and/or by sterile filtration. The two major components of Capxol™ are unmodified paclitaxel and human serum albumin (HSA). Since HSA is freely soluble in water, Capxol™ can be reconstituted to any desired concentration of paclitaxel limited only by the solubility limits for HSA. Thus Capxol™ can be reconstituted in a wide range of concentrations ranging from dilute (0.1 mg/ml paclitaxel) to concentrated (20 mg/ml paclitaxel). This can result in fairly small volumes of administration.

As used herein, the term "in vivo delivery" refers to delivery of a pharmacologically active agent by such routes of administration as oral, intravenous, subcutaneous, intraperitoneal, intrathecal, intramuscular, inhalational, topical, transdermal, suppository (rectal), pessary (vaginal), intra urethral, intraportal, intrahepatic, intra-arterial, intraumoral, and the like.

As used herein, the term "micron" refers to a unit of measure of one one-thousandth of a millimeter.

As used herein, the term "biocompatible" describes a substance that does not appreciably alter or affect in any adverse way, the biological system into which it is introduced.

Substantially water insoluble pharmacologically active agents contemplated for use in the practice of the present invention include pharmaceutically active agents, diagnostic agents, agents of nutritional value, and the like. Examples of pharmaceutically active agents include:
 analgesics/antipyretics (e.g., aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, oxycodone hydrochloride, codeine phosphate, dihydrocodeine bitartrate, pentazocine hydrochloride, hydrocodone bitartrate, levorphanol tartrate, diflunisal, trolamine salicylate, nalbuphine hydrochloride, mefenamic acid, butorphanol tartrate, choline salicylate, butalbital, phenyltoloxamine citrate, diphenhydramine citrate, methotrimeprazine, cinnamedrine hydrochloride, meprobamate, and the like);

anesthetics (e.g., cyclopropane, enflurane, halothane, isoflurane, methoxyflurane, nitrous oxide, propofol, and the like);

antiasthmatics (e.g., Azelastine, Ketotifen, Traxanox, Amlexanox, Cromolyn, Ibudilast, Montelukast, Nedocromil, Oxatomide, Pranlukast, Seratrodast, Suplatast Tosylate, Tiaramide, Zafirlukast, Zileuton, Beclomethasone, Budesonide, Dexamethasone, Flunisolide, Trimcinolone Acetonide, and the like);

antibiotics (e.g., neomycin, streptomycin, chloramphenicol, cephalosporin, ampicillin, penicillin, tetracycline, and the like);

antidepressants (e.g., nefopam, oxypertine, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, and the like);

antidiabetics (e.g., biguanides, hormones, sulfonylurea derivatives, and the like);

antifungal agents (e.g., griseofulvin, keloconazole, amphotericin B, Nystatin, candicidin, and the like);

antihypertensive agents (e.g., propanolol, propafenone, oxyprenolol, Nifedipine, reserpine, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, and the like);

anti-inflammatories (e.g., (non-steroidal) indomethacin, naproxen, ibuprofen, ramifenazone, piroxicam, (steroidal) cortisone, dexamethasone, fluazacort, hydrocortisone, prednisolone, prednisone, and the like);

antineoplastics (e.g., adriamycin, cyclophosphamide, actinomycin, bleomycin, duanorubicin, doxorubicin, epirubicin, mitomycin, methotrexate, fluorouracil, carboplatin, carmustine (BCNU), methyl-CCNU, cisplatin, etoposide, interferons, camptothecin and derivatives thereof, phenesterine, Taxol and derivatives thereof, taxotere and derivatives thereof, vinblastine, vincristine, tamoxifen, etoposide, piposulfan, and the like);

antianxiety agents (e.g., lorazepam, buspirone hydrochloride, prazepam, chlordiazepoxide hydrochloride, oxazepam, clorazepate dipotassium, diazepam, hydroxyzine pamoate, hydroxyzine hydrochloride, alprazolam, droperidol, halazepam, chlormezanone, dantrolene, and the like);

immunosuppressive agents (e.g., cyclosporine, azathioprine, mizoribine, FK506 (tacrolimus), and the like);

antimigraine agents (e.g., ergotamine tartrate, propanolol hydrochloride, isometheptene mucate, dichloralphenazone, and the like);

sedatives/hypnotics (e.g., barbiturates (e.g., pentobarbital, pentobarbital sodium, secobarbital sodium), benzodiazepines (e.g., flurazepam hydrochloride, triazolam, tomazeparm, midazolam hydrochloride, and the like);

antianginal agents (e.g., beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate, and the like));

antipsychotic agents (e.g., haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, and the like);

antimanic agents (e.g., lithium carbonate);

antiarrhythmics (e.g., bretylium tosylate, esmolol hydrochloride, verapamil hydrochloride, amiodarone, encainide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, and the like);

antiarthritic agents (e.g., phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, and the like);

antigout agents (e.g., colchicine, allopurinol, and the like);

anticoagulants (e.g., heparin, heparin sodium, warfarin sodium, and the like);

thrombolytic agents (e.g., urokinase, streptokinase, altoplase, and the like);

antifibrinolytic agents (e.g., aminocaproic acid);

hemorheologic agents (e.g., pentoxifylline);

antiplatelet agents (e.g., aspirin, empirin, ascriptin, and the like);

anticonvulsants (e.g., valproic acid, divalproate sodium, phenytoin, phenytoin sodium, clonazepam, primidone, phenobarbitol, phenobarbitol sodium, carbamazepine, amobarbital sodium, methsuximide, metharbital, mephobarbital, mephenytoin, phensuximide, paramethadione, ethotoin, phenacemide, secobarbitol sodium, clorazepate dipotassium, trimethadione, and the like);

antiparkinson agents (e.g., ethosuximide, and the like);

antihistamines/antipruritics (e.g., hydroxyzine hydrochloride, diphenhydramine hydrochloride, chlorpheniramine maleate, brompheniramine maleate, cyproheptadine hydrochloride, terfenadine, clemastine fumarate, triprolidine hydrochloride, carbinoxamine maleate, diphenylpyraline hydrochloride, phenindamine tartrate, azatadine maleate, tripelennamine hydrochloride, dexchlorpheniramine maleate, methdilazine hydrochloride, trimprazine tartrate and the like);

agents useful for calcium regulation (e.g., calcitonin, parathyroid hormone, and the like);

antibacterial agents (e.g., amikacin sulfate, aztreonam, chloramphenicol, chloramphenicol palmitate, chloramphenicol sodium succinate, ciprofloxacin hydrochloride, clindamycin hydrochloride, clindamycin palmitate, clindamycin phosphate, metronidazole, metronidazole hydrochloride, gentamicin sulfate, lincomycin hydrochloride, tobramycin sulfate, vancomycin hydrochloride, polymyxin B sulfate, colistimethate sodium, colistin sulfate, and the like);

antiviral agents (e.g., interferon gamma, zidovudine, amantadine hydrochloride, ribavirin, acyclovir, and the like);

antimicrobials (e.g., cephalosporins (e.g., cefazolin sodium, cephradine, cefaclor, cephapirin sodium, ceftizoxime sodium, cefoperazone sodium, cefotetan disodium, cefutoxime azotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, and the like), and the like);

anti-infectives (e.g., GM-CSF);

bronchodialators (e.g., sympathomimetics (e.g., epinephrine hydrochloride, metaproterenol sulfate, terbutaline sulfate, isoetharine, isoetharine mesylate, isoetharine hydrochloride, albuterol sulfate, albuterol, bitolterol, mesylate isoproterenol hydrochloride, terbutaline sulfate, epinephrine bitartrate, metaproterenol sulfate, epinephrine, epinephrine bitartrate), anticholinergic agents (e.g., ipratropium bromide), xanthines (e.g., aminophylline, dyphylline, metaproterenol sulfate, aminophylline), mast cell stabilizers (e.g., cromolyn sodium), inhalant corticosteroids (e.g., flurisolidebeclomethasone dipropionate, beclomethasone dipropionate monohydrate), salbutamol, beclomethasone dipropionate (BDP), ipratropium bromide, budesonide, ketotifen, salmeterol, xinafoate, terbutaline sulfate, triamcinolone, theophylline, nedocromil sodium, metaproterenol sulfate, albuterol, flunisolide, and the like);

hormones (e.g., androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), corticosteroids (e.g., triamcinolone, betamethasone, betamethasone sodium phosphate, dexamethasone, dexamethasone sodium phosphate, dexamethasone acetate, prednisone, methylprednisolone acetate suspension, triamcinolone acetonide, methylprednisolone, prednisolone sodium phosphate methylprednisolone sodium succinate, hydrocortisone sodium succinate, methylprednisolone sodium succinate, triamcinolone hexacatonide, hydrocortisone, hydrocortisone cypionate, prednisolone, fluorocortisone acetate, paramethasone acetate, prednisolone tebulate, prednisolone acetate, prednisolone sodium phosphate, hydrocortisone sodium succinate, and the like), thyroid hormones (e.g., levothyroxine sodium) and the like), and the like;

hypoglycemic agents (e.g., human insulin, purified beef insulin, purified pork insulin, glyburide, chlorpropamide, glipizide, tolbutamide, tolazamide, and the like);

hypolipidemic agents (e.g., clofibrate, dextrothyroxine sodium, probucol, lovastatin, niacin, and the like);

proteins (e.g., DNase, alginase, superoxide dismutase, lipase, and the like);

nucleic acids (e.g., sense or anti-sense nucleic acids encoding any therapeutically useful protein, including any of the proteins described herein, and the like);

agents useful for erythropoiesis stimulation (e.g., erythropoietin);

antiulcer/antireflux agents (e.g., famotidine, cimetidine, ranitidine hydrochloride, and the like);

antinauseants/antiemetics (e.g., meclizine hydrochloride, nabilone, prochlorperazine, dimenhydrinate, promethazine hydrochloride, thiethylperazine, scopolamine, and the like);

oil-soluble vitamins (e.g., vitamins A, D, E, K, and the like); and as well as other drugs such as mitotane, visadine, halonitrosoureas, anthrocyclines, ellipticine, and the like.

Examples of diagnostic agents contemplated for use in the practice of the present invention include ultrasound contrast agents, radiocontrast agents (e.g., iodo-octanes, halocarbons, renografin, and the like), magnetic contrast agents (e.g., fluorocarbons, lipid soluble paramagnetic compounds, and the like), as well as other diagnostic agents which cannot readily be delivered without some physical and/or chemical modification to accommodate the substantially water insoluble nature thereof.

Examples of agents of nutritional value contemplated for use in the practice of the present invention include amino acids, sugars, proteins, carbohydrates, fat-soluble vitamins (e.g., vitamins A, D, E, K, and the like) or fat, or combinations of any two or more thereof.

A. Formation of Nanoparticles Using High Shear Homogenization

Key differences between the pharmacologically active agents contained in a polymeric shell according to the invention and protein microspheres of the prior art are in the nature of formation and the final state of the protein after formation of the particle, and its ability to carry poorly aqueous-soluble or substantially aqueous-insoluble agents. In accordance with the present invention, the polymer. (e.g., a protein) may be crosslinked as a result of exposure to high shear conditions in a high pressure homogenizer. High shear is used to disperse a dispersing agent containing dissolved or suspended pharmacologically active agent into an aqueous solution of a biocompatible polymer, optionally bearing sulfhydryl or disulfide groups (e.g., albumin) whereby a shell of crosslinked polymer is formed around fine droplets of non-aqueous medium. The high shear conditions produce cavitation in the liquid that causes tremendous local heating and results in the formation of superoxide ions that are capable of crosslinking the polymer, for example, by oxidizing the sulfhydryl residues (and/or disrupting existing disulfide bonds) to form new, crosslinking disulfide bonds.

In contrast to the invention process, the prior art method of glutaraldehyde crosslinking is nonspecific and essentially reactive with any nucleophilic group present in the protein structure (e.g., amines and hydroxyls). Heat denaturation as taught by the prior art significantly and irreversibly alters protein structure. In contrast, disulfide formation contemplated by the present invention does not substantially denature the protein. In addition, particles of substantially water insoluble pharmacologically active agents contained within a shell differ from crosslinked or heat denatured protein microspheres of the prior art because the polymeric shell produced by the invention process is relatively thin compared to the diameter of the coated particle. It has been determined (by transmission electron microscopy) that the "shell thickness" of the polymeric coat is approximately 25 nanometers for a coated particle having a diameter of 1 micron (1000 nanometers). In contrast, microspheres of the prior art do not have protein shells, but rather, have protein dispersed throughout the volume of the microsphere.

Thus, in accordance with the present invention, a pharmacologically active agent is dissolved in a suitable solvent (e.g., chloroform, methylene chloride, ethyl acetate, ethanol, tetrahydrofuran, dioxane, butanol, butyl acetate, acetonitrile, acetone, dimethyl sulfoxide, dimethyl formamide, methyl pyrrolidinone, or the like, as well as mixtures of any two or more thereof). Additional solvents contemplated for use in the practice of the present invention include soybean oil, coconut oil, olive oil, safflower oil, cotton seed oil, sesame oil, orange oil, limonene oil, C1-C20 alcohols, C2-C20 esters, C3-C20 ketones, polyethylene glycols, aliphatic hydrocarbons, aromatic hydrocarbons, halogenated hydrocarbons and combinations thereof.

Unlike conventional methods for nanoparticle formation, a polymer (e.g. polylactic acid) is not dissolved in the solvent. The oil phase employed in the preparation of invention compositions typically contains only the pharmacologically active agent dissolved in solvent.

Next, a protein (e.g., human serum albumin) is added (into the aqueous phase) to act as a stabilizing agent for the formation of stable nanodroplets. Protein is added at a concentration in the range of about 0.05 to 25% (w/v), more preferably in the range of about 0.5%-5% (w/v). Unlike conventional methods for nanoparticle formation, no surfactant (e.g. sodium lauryl sulfate, lecithin, tween 80, pluronic F-68 and the like) is added to the mixture.

Next, an emulsion is formed by homogenization under high pressure and high shear forces. Such homogenization is conveniently carried out in a high pressure homogenizer, typically operated at pressures in the range of about 3,000 up to 60,000 psi. Preferably, such processes are carried out at pressures in the range of about 6,000 up to 40,000 psi. The resulting emulsion comprises very small nanodroplets of the nonaqueous solvent (containing the dissolved pharmacologically active agent) and very small nanodroplets of the protein stabilizing agent. Acceptable methods of homogenization include processes imparting high shear and cavitation such as high pressure homogenization, high shear mixers, sonication, high shear impellers, and the like.

Finally, the solvent is evaporated under reduced pressure to yield a colloidal system composed of protein coated nanoparticles of pharmacologically active agent and protein. Acceptable methods of evaporation include the use of rotary evaporators, falling film evaporators, spray driers, freeze driers, and the like. Ultrafiltration may also be used for solvent removal.

Following evaporation of solvent, the liquid suspension may be dried to obtain a powder containing the pharmacologically active agent and protein. The resulting powder can be redispersed at any convenient time into a suitable aqueous medium such as saline, buffered saline, water, buffered aqueous-media, solutions of amino acids, solutions of vitamins, solutions of carbohydrates, or the like, as well as combinations of any two or more thereof, to obtain a suspension that can be administered to mammals. Methods contemplated for obtaining this powder include freeze-drying, spray drying, and the like.

In accordance with another embodiment of the present invention, there is provided an alternative method for the formation of unusually small submicron particles (nanoparticles), i.e., particles which are less than 200 nanometers in diameter. Such particles are capable of being sterile-filtered before use in the form of a liquid suspension. The ability to sterile-filter the end product of the invention formulation process (i.e., the drug particles) is of great importance since it is impossible to sterilize dispersions which contain high concentrations of protein (e.g., serum albumin) by conventional means such as autoclaving.

In order to obtain sterile-filterable particles (i.e., particles <200 nm), the pharmacologically active agent is initially dissolved in a substantially water immiscible organic solvent (e.g., a solvent having less than about 5% solubility in water, such as, for example, chloroform) at high concentration, thereby forming an oil phase containing the pharmacologically active agent. Suitable solvents are set forth above. Unlike conventional methods for nanoparticle formation, a polymer (e.g. polylactic acid) is not dissolved in the solvent. The oil phase employed in the process of the present invention contains only the pharmacologically active agent dissolved in solvent.

Next, a water miscible organic solvent (e.g., a solvent having greater than about 10% solubility in water, such as, for example, ethanol) is added to the oil phase at a final concentration in the range of about 1%-99% v/v, more preferably in the range of about 5%-25% v/v of the total organic phase. The water miscible organic solvent can be selected from such solvents as ethyl acetate, ethanol, tetrahydrofuran, dioxane, acetonitrile, gutanol, acetone, propylene glycol, glycerol, dimethyl sulfoxide, dimethyl formamide, methyl pyrrolidinone, and the like. Alternatively, the mixture of water immiscible solvent with the water miscible solvent is prepared first, followed by dissolution of the pharmaceutically active agent in the mixture.

Next, human serum albumin or any other suitable stabilizing agent as described above is dissolved in aqueous media. This component acts as a stabilizing agent for the formation of stable nanodroplets. Optionally, a sufficient amount of the first organic solvent (e.g. chloroform) is dissolved in the aqueous phase to bring it close to the saturation concentration. A separate, measured amount of the organic phase (which now contains the pharmacologically active agent, the first organic solvent and the second organic solvent) is added to the saturated aqueous phase, so that the phase fraction of the organic phase is between about 0.5%-15% v/v, and more preferably between 1% and 8% v/v.

Next, a mixture composed of micro and nanodroplets is formed by homogenization at low shear forces. This can be accomplished in a variety of ways, as can readily be identified by those of skill in the art, employing, for example, a conventional laboratory homogenizer operated in the range of about 2,000 up to about 15,000 rpm. This is followed by homogenization under high pressure (i.e., in the range of about 3,000 up to 60,000 psi). The resulting mixture comprises an aqueous protein solution (e.g., human serum albumin), the water insoluble pharmacologically active agent, the first solvent and the second solvent. Finally, solvent is rapidly evaporated under vacuum to yield a colloidal dispersion system (pharmacologically active agent and protein) in the form of extremely small nanoparticles (i.e., particles in the range of about 10 nm-200 nm diameter) that can be sterile-filtered. The preferred size range of the particles is between about 50 nm-170 nm, depending on the formulation and operational parameters.

Colloidal systems prepared in accordance with the present invention may be further converted into powder form by removal of the water therefrom, e.g., by lyophilization or spray drying at a suitable temperature-time profile. The protein (e.g., human serum albumin) itself acts as a cryoprotectant or lyoprotectant, and the powder is easily reconstituted by addition of water, saline or buffer, without the need to use such conventional cryoprotectants as mannitol, sucrose, glycine, and the like. While not required, it is of course understood that conventional cryoprotectants may be added to invention formulations if so desired.

The colloidal system of pharmacologically active agent allows for the delivery of high doses of the pharmacologically active agent in relatively small volumes. This minimizes patient discomfort at receiving large volumes of fluid and minimizes hospital stay. In addition, the walls of the polymeric shell or coating are generally completely degradable in vivo by proteolytic enzymes (e.g., when the polymer is a protein), resulting in substantially no side effects from the delivery system, which is in sharp contrast to the significant side effects caused by current formulations.

A number of biocompatible polymers may be employed in the practice of the present invention for the formation of the polymeric shell which surrounds the substantially water insoluble pharmacologically active agents. Essentially any polymer, natural or synthetic, optionally bearing sulfhydryl groups or disulfide bonds within its structure may be utilized for the preparation of a disulfide crosslinked shell about particles of substantially water insoluble pharmacologically active agents. The sulfhydryl groups or disulfide linkages may be preexisting within the polymer structure or they may be introduced by a suitable chemical modification. For example, natural polymers such as proteins, peptides, polynucleic acids, polysaccharides (e.g., starch, cellulose, dextrans, alginates, chitosan, pectin, hyaluronic acid, and the like), proteoglycans, lipoproteins, and so on, are candidates for such modification.

Proteins contemplated for use as stabilizing agents in accordance with the present invention include albumins (which contain 35 cysteine residues), immunoglobulins, caseins, insulins (which contain 6 cysteines), hemoglobins (which contain 6 cysteine residues per $a_2\beta_2$ unit), lysozymes (which contain 8 cysteine residues), immunoglobulins, alpah-2-macroglobulin, fibronectins, vitronectins, fibrinogens, lipases, and the like. Proteins, peptides, enzymes, antibodies and combinations thereof, are general classes of stabilizers contemplated for use in the present invention.

A presently preferred protein for use as a stabilizing agent is albumin. Optionally, proteins such as alpha-2-macroglobulin, a known opsonin, could be used to enhance uptake of the shell encased particles of substantially water insoluble pharmacologically active agents by macrophage-like cells, or to enhance the uptake of the shell encased particles into the liver and spleen. Specific antibodies may also be utilized to target the nanoparticles to specific locations.

Other functional proteins, such as antibodies or enzymes, which could facilitate targeting of biologic to a desired site, can also be used as components of the stabilizing protein.

Similarly, synthetic polymers are also good candidates for formation of particles having a polymeric shell. In addition, polyalkylene glycols (e.g., linear or branched chain), polyvinyl alcohol, polyacrylates, polyhydroxyethyl methacrylate, polyacrylic acid, polyethyloxazoline, polyacrylamides, polyisopropyl acrylamides, polyvinyl pyrrolidinone, polylactide/glycolide and the like, and combinations thereof, are good candidates for the biocompatible polymer in the invention formulation.

Similarly, synthetic polypeptides are also good candidates for stabilizing agents for the substantially water insoluble pharmacologically active agents. In addition, contemplated for use in the practice of the present invention are such materials as synthetic polyamino acids containing cysteine residues and/or disulfide groups; polyvinyl alcohol modified to contain free sulfhydryl groups and/or disulfide groups; polyhydroxyethyl methacrylate modified to contain free sulfhydryl groups and/or disulfide groups; polyacrylic acid modified to contain free sulfhydryl groups and/or disulfide groups; polyethyloxazoline modified to contain free sulfhydryl groups and/or disulfide groups; polyacrylamide modified to contain free sulfhydryl groups and/or disulfide groups; polyvinyl pyrrolidinone modified to contain free sulfhydryl groups and/or disulfide groups; polyalkylene glycols modified to contain free sulfhydryl groups and/or disulfide groups; polylactides, polyglycolides, polycaprolactones, or copolymers thereof, modified to contain free sulfhydryl groups and/or disulfide groups; as well as mixtures of any two or more thereof.

In the preparation of invention compositions, a wide variety of organic media can be employed to suspend or dissolve the substantially water insoluble pharmacologically active agent. Organic media contemplated for use in the practice of the present invention include any nonaqueous liquid that is capable of suspending or dissolving the pharmacologically active agent, but does not chemically react with either the olymer employed to produce the shell, or the pharmacologically active agent itself. Examples include vegetable oils (e.g., soybean oil, olive oil, and the like), coconut oil, safflower oil, cotton seed oil, sesame oil, orange oil, limonene oil, aliphatic, cycloaliphatic, or aromatic hydrocarbons having 4-30 carbon atoms (e.g., n-dodecane, n-decane, n-hexane, cyclohexane, toluene, benzene, and the like), aliphatic or aromatic alcohols having 2-30 carbon atoms (e.g., octanol, and the like), aliphatic or aromatic esters having 2-30 carbon atoms (e.g., ethyl caprylate (octanoate), and the like), alkyl, aryl, or cyclic ethers having 2-30 carbon atoms (e.g., diethyl ether, tetrahydrofuran, and the like), alkyl or aryl halides having 1-30 carbon atoms (and optionally more than one halogen substituent, e.g., $CH_3Cl$, $CH_2Cl_2$, $CH_2Cl$—$CH_2Cl$, and the like), ketones having 3-30 carbon atoms (e.g., acetone, methyl ethyl ketone, and the like), polyalkylene glycols (e.g., polyethylene glycol, and the like), or combinations of any two or more thereof.

Especially preferred combinations of organic media contemplated for use in the practice of the present invention typically have a boiling point of no greater than about 200° C., and include volatile liquids such as dichloromethane, chloroform, ethyl acetate, benzene, ethanol, butanol, butyl acetate, and the like (i.e., solvents that have a high degree of solubility for the pharmacologically active agent, and are soluble in the other organic medium employed), along with a higher molecular weight (less volatile) organic medium. When added to the other organic medium, these volatile additives help to drive the solubility of the pharmacologically active agent into the organic medium. This is desirable since this step is usually time consuming. Following dissolution, the volatile component may be removed by evaporation (optionally under vacuum).

Particles of pharmacologically active agent associated with a polymeric shell, prepared as described above, are delivered as a suspension in a biocompatible aqueous liquid. This liquid may be selected from water, saline, a solution containing appropriate buffers, a solution containing nutritional agents such as amino acids, sugars, proteins, carbohydrates, vitamins or fat, and the like.

These biocompatible materials may also be employed in several physical forms such as gels, crosslinked or uncrosslinked to provide matrices from which the pharmacologically active ingredient, for example paclitaxel, may be released by diffusion and/or degradation of the matrix. Temperature sensitive materials may also be utilized as the dispersing matrix for the invention formulation. Thus for example, the Capxol may be injected in a liquid formulation of the temperature sensitive material (e.g., copolymers of polyacrylamides or copolymers of polyalkylene glycols and polylactide/glycolides) which gel at the tumor site and provide slow release of Capxol. The Capxol formulation may be dispersed into a matrix of the above mentioned biocompatible polymers to provide a controlled release formulation of paclitaxel, which through the properties of the Capxol formulation (albumin associated with paclitaxel) results in lower toxicity to brain tissue as well as lower systemic toxicity as discussed below. This combination of Capxol or other chemotherapeutic agents formulated similar to Capxol together with a biocompatible polymer matrix may be useful for the controlled local delivery of chemotherapeutic agents for treating solid tumors in the brain and peritoneum (ovarian cancer) and in local applications to other solid tumors. These combination formulations are not limited to the use of paclitaxel and may be utilized with a wide variety of pharmacologically active ingredients including antiinfectives, immunosuppressives and other chemotherapeutics and the like.

Particles colloidal substantially completely contained within a polymeric stabilizing layerl, or associated therewith, prepared as described herein, are delivered neat, or optionally as a suspension in a biocompatible medium. This medium may be selected from water, buffered aqueous media, saline, buffered saline, optionally buffered solutions of amino acids, optionally buffered solutions of proteins, optionally buffered solutions of sugars, optionally buffered solutions of carbohydrates, optionally buffered solutions of vitamins, optionally buffered solutions of synthetic polymers, lipid-containing emulsions, and the like.

In addition, the colloidal particles can optionally be modified by a suitable agent, wherein the agent is associated with the polymeric layer through an optional covalent bond. Covalent bonds contemplated for such linkages include ester, ether, urethane, diester, amide, secondary or tertiary amine, phosphate ester, sulfate ester, and the like bonds. Suitable agents contemplated for this optional modification of the polymeric shell include synthetic polymers (polyalkylene glycols (e.g., linear or branched chain polyethylene glycol), polyvinyl alcohol, polyhydroxyethyl methacrylate, polyacrylic acid, polyethyloxazoline, polyacrylamide, polyvinyl pyrrolidinone, and the like), phospholipids (such as phosphatidyl choline (PC), phosphatidyl ethanolamine (PE), phosphatidyl inositol (PI), sphingomyelin, and the like), proteins (such as enzymes, antibodies, and the like), polysaccharides (such as starch, cellulose, dextrans, alginates, chitosan, pectin, hyaluronic acid, and the like), chemical modifying agents (such as pyridoxal 5'-phosphate, derivatives of pyridoxal, dialdehydes, diaspirin esters, and the like), or combinations of any two or more thereof.

Variations on the general theme of stabilized colloidal particles are possible. A suspension of fine particles of pharmacological agent in a biocompatible dispersing agent could be used (in place of a biocompatible dispersing agent containing dissolved biologic) to produce a polymeric shell containing dispersing agent-suspended particles of biologic. In other words, the polymeric shell could contain a saturated solution of biologic in dispersing agent. Another variation is a polymeric shell containing a solid core of biologic produced by initially dissolving the biologic in a volatile organic solvent (e.g. benzene), forming the polymeric shell and evaporating the volatile solvent under vacuum, e.g., in an evaporator, spray drier or freeze-drying the entire suspension. This results in a structure having a solid core of biologic surrounded by a polymer coat. This latter method is particularly advantageous for delivering high doses of biologic in a relatively small volume. In some cases, the biocompatible material forming the shell about the core could itself be a therapeutic or diagnostic agent, e.g., in the case of insulin, which may be delivered as part of a polymeric shell formed in the process described above. In other cases, the polymer forming the shell could participate in the delivery of a biologic, e.g., in the case of antibodies used for targeting, or in the case of hemoglobin, which may be delivered as part of a polymeric shell formed in the ultrasonic irradiation process described above, thereby providing a blood substitute having a high binding capacity for oxygen.

Those skilled in the art will recognize that several variations are possible within the scope and spirit of this aspect of the invention. The organic medium within the polymeric shell may be varied, a large variety of pharmacologically active agents may be utilized, and a wide range of proteins as well as other natural and synthetic polymers may be used in the formation of the walls of the polymeric shell. Applications are also fairly wide ranging. Other than biomedical applications such as the delivery of drugs, diagnostic agents (in imaging applications), artificial blood and parenteral nutritional agents, the polymeric shell structures of the invention may be incorporated into cosmetic applications such as skin creams or hair care products, in perfumery applications, in pressure sensitive inks, and the like.

This aspect of the invention will now be described in greater detail by reference to the following non-limiting examples.

EXAMPLE 1

Preparation of Nanoparticles by High Pressure Homogenization 30 mg paclitaxel is dissolved in 3.0 ml methylene chloride. The solution was added to 27.0 ml of human serum abumin solution (1% w/v). The mixture was homogenized for 5 minutes at low RPM (Vitris homogenizer, model: Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotary evaporator, and methylene chloride was rapidly removed at 40° C., at reduced pressure (30 mm Hg), for 20-30 minutes. The resulting dispersion was translucent, and the typical diameter of the resulting paclitaxel particles was 160-220 (Z-average, Malvern Zetasizer).

The dispersion was further lyophilized for 48 hrs without adding any cryoprotectant. The resulting cake could be easily reconstituted to the original dispersion by addition of sterile water or saline. The particle size after reconstitution was the same as before lyophilization.

EXAMPLE 2

Use of Conventional Surfactants and Proteins Results in Formation of Larae Crystals The following example demonstrates the effect of adding surfactants which are used in the conventional solvent evaporation method. A series of experiments was conducted employing a similar procedure to that described in Example 1, but a surfactant such as Tween 80 (1% to 10%) is added to the organic solvent. It was found that after removal of the methylene chloride, a large number of paclitaxel crystals is obtained having an average size of 1-2 micron, as viewed by light microscopy and under polarized light. The crystals grow within a few hours to form very large needle-like crystals, with a size in the range of about 5-15 micron. A similar phenomenon is observed with other commonly used surfactants, such as Pluronic F-68, Pluronic F-127, Cremophor EL and Brij 58.

From these results it can be concluded that the conventional solvent evaporation method utilizing conventional surfactants in combination with a protein such as albumin is not suitable for the formation of submicron drug particles (e.g. Paclitaxel) without a polymeric core, while using a polar solvent (e.g., methylene chloride).

EXAMPLE 3

Use of Conventional Surfactants Alone Results in Formation of Large Crystals

This example demonstrates that it is not possible to form nanoparticles while using conventional surfactants, without a polymeric core material, with pharmacologically active agents which are soluble in polar, water immiscible solvents (e.g. chloroform).

30 mg Taxol is dissolved in 0.55 ml chloroform and 0.05 ml ethanol. The solution is added to 29.4 ml of Tween 80 solution (1% w/v), which is presaturated with 1% chloroform. The mixture is homogenized for 5 minutes at low RPM (Vitris homogenizer, model: Tempest I.Q.) in order to form a crude emulsion, and then transferred into a high pressure homogenizer (Avestin). The emulsification is performed at 9000-40,000 psi while recycling the emulsion for at least 6 cycles. The resulting system was transferred into a Rotary evaporator, and the chloroform was rapidly removed at 40° C., at reduced pressure (30 mm Hg), for 15-30 minutes. The resulting dispersion was opaque, and contained large needle-like crystals of the drug. The initial size of the crystals (observed also by polarized light), was 0.7-5 micron. Storage of the dispersion for several hours at room temperature led to further increase in crystal size, and ultimately to precipitation.

EXAMPLE 4

Preparation of Less than 200 nm Sterile-Filterable Nanoparticles

This example describes a process by which sterile-filterable drug particles can be obtained. Thus, 30 mg Taxol is dissolved in 0.55 ml chloroform and 0.05 ml ethanol. The solution is added to 29.4 ml of human serum abumin solution (1% w/v), which is presaturated with 1% chloroform. The mixture is homogenized for 5 minutes at low RPM (Vitris homogenizer, model: Tempest I.Q.) in order to form a crude emulsion, and then transferred into a high pressure homogenizer (Avestin) The emulsification is performed at 9000-40,000 psi while recycling the emulsion for at least 6 cycles. The resulting system is transferred into a Rotary evaporator, and the chloroform is rapidly removed at 40° C., at reduced pressure (30 mm Hg), for 15-30 minutes. The resulting dispersion is translucent, and the typical diameter of the resulting Taxol particles is 140-160 nm (Z-average, Malvern Zeta Sizer). The dispersion is filtered through a 0.22 micron filter (Millipore), without any significant change in turbidity, or particle size. HPLC analysis of the Taxol content revealed that more than 97% of the Taxol was recovered after filtration, thus providing a sterile Taxol dispersion.

The sterile dispersion was further lyophilized for 48 hrs without adding any cryoprotectant. The resulting cake could be easily reconstituted to the original dispersion by addition of sterile water or saline. The particle size after reconstitution was the same as before lyophilization.

EXAMPLE 5

Preparation of Less than 200 nm Sterile-Filterable Nanoparticles

This example describes a process by which sterile-filterable drug particles can be obtained. Thus, 225 mg Taxol is dissolved in 2.7 ml chloroform and 0.3 ml ethanol. The solution is added to 97 ml of human serum abumin solution (3% w/v). The mixture is homogenized for 5 minutes at low RPM (Vitris homogenizer, model: Tempest I.Q.) in order to form a crude emulsion, and then transferred into a high pressure homogenizer (Avestin). The emulsification is performed at 9000-40,000 psi while recycling the emulsion for at least 6 cycles. The resulting system is transferred into a Rotary evaporator, and the chloroform is rapidly removed at 40° C., at reduced pressure (30 mm Hg), for 15-30 minutes. The resulting dispersion is translucent, and the typical diameter of the resulting Taxol particles is 140-160 nm (Z-average, Malvern Zeta Sizer). The dispersion is filtered through a 0.22 micron filter (Sartorius, sartobran 300), without any significant change in turbidity, or particle size. HPLC analysis of the Taxol content typically revealed that 70-100% of the Taxol could be recovered after filtration, depending on the conditions employed. Thus, a sterile Taxol dispersion was obtained.

The sterile dispersion was aseptically filled into sterile glass vials and lyophilized without adding any cryoprotectant. The resulting cake could be easily reconstituted to the original dispersion by addition of sterile water or saline. The particle size after reconstitution was the same as before lyophilization.

EXAMPLE 8

Nanoparticle Formation of a Model Drug 30 mg Isoreserpine (a model drug) is dissolved in 3.0 ml methylene chloride. The solution is added to 27.0 ml of human serum abumin solution (1% w/v). The mixture is homogenized for 5 minutes at low RPM (Vitris homogenizer, model: Tempest I.Q.) in order to form a crude emulsion, and then transferred into a high pressure homogenizer (Avestin). The emulsification is performed at 9000-18,000 psi while recycling the emulsion for at least 5 cycles. The resulting system is transferred into a Rotary evaporator, and methylene chloride is rapidly removed at 40° C., at reduced pressure (30 mm Hg), for 20-30 minutes. The resulting dispersion is translucent, and the typical diameter of the resulting paclitaxel particles was 120-140 nm (Z-average, Malvern Zetasizer). The dispersion was filtered through a 0.22 micron filter (Millipore).

The sterile dispersion was further lyophilized for 48 hrs without adding any cryoprotectant. The resulting cake could be easily reconstituted to the original dispersion by addition of sterile water or saline. The particle size after reconstitution was the same as before lyophilization.

EXAMPLE 9

Extremely Small Particle Formation with a Model Drug

The effect of ethanol addition on reducing particle size is demonstrated for Isoreserpine. Thus, 30 mg Isoreserpine is dissolved in 2.7 ml methylene chloride and 0.3 ml ethanol. The solution is added to 27.0 ml of human serum abumin solution (1% w/v). The mixture is homogenized for 5 minutes at low RPM (Vitris homogenizer, model: Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotary evaporator, and methylene chloride was rapidly removed at 40° C., at reduced pressure (30 mm Hg), for 20-30 minutes. The resulting dispersion was translucent, and the typical diameter of the resulting paclitaxel particles was 90-110 nm (Z-average, Malvern Zetasizer). The dispersion was filtered through a 0.22 micron filter (Millipore).

The sterile dispersion was further lyophilized for 48 hrs without adding any cryoprotectant. The resulting cake could be easily reconstituted to the original dispersion by addition of sterile water or saline. The particle size after reconstitution was the same as before lyophilization.

EXAMPLE 10

Use of a Water Miscible Solvent Alone, Supersaturated with Drug—Not Suitable for Invention Process 30 mg Taxol is dispersed in 0.6 ml ethanol. At this concentration (50 mg/ml), the Taxol is not completely soluble and forms a supersaturated dispersion. The dispersion is added to 29.4 ml of human serum abumin solution (1% w/v). The mixture is homogenized for 5 minutes at low RPM (Vitris homogenizer, model: Tempest I.Q.) in order to form a crude dispersion, and then transferred into a high pressure homogenizer (Avestin). The emulsification is performed at 9000-40,000 psi while recycling the emulsion for at least 6 cycles. The resulting system is transferred into a Rotary evaporator, and the ethanol is rapidly removed at 40° C., at reduced pressure (30 mm Hg), for 15-30 minutes. The resulting dispersion particle size is extremely broad, ranging from about 250 nm to several microns.

Observation under the microscope revealed the presence of large particles and typical needle shaped crystals of Taxol. These particles were too large for intravenous injection. This experiment demonstrates that the use of solvents such as ethanol that are freely miscible in water in the invention process results in the formation of large particles with very broad particle size distribution and as such cannot be used alone for the invention process. Thus the invention process specifically excludes the use of water miscible solvents when used alone for the dissolution or dispersion of the drug component. The invention process requires that such solvents, when used, must be mixed with essentially water immiscible solvents to allow production of the invention nanoparticles.

EXAMPLE 12

Determination of Physical State of Paclitaxel in Nanoparticle Form by X-Ray Powder Diffraction Paclitaxel raw material is usually present as needle shaped crystals of varying sizes typically between 5-500 microns. The presence of crystals in a drug formulation for intravenous injection is obviously detrimental if crystals are present in size above a few microns due to potential blockage of capillaries. In addition, the solubility of drug crystals in general would be lower than for amorphous drug, thereby lowering the bioavailability of the drug following intravenous administration. It is also known that as the loading of the drug in a formulation is increased, the tendency for crystallization also increases. Thus it is advantageous that the formulation contain the drug in essentially amorphous form.

X-Ray powder diffraction was used to determine the crystalline or non-crystalline nature of paclitaxel in the lyophilized powder formulation. The following samples were analyzed: Sample 1—Paclitaxel powder; Sample 2—Lyophilized serum albumin; Sample 3—a physical mixture of paclitaxel and albumin; and Sample 4—formulated paclitaxel. Each sample was x-rayed from 2° to 70° 2-theta angles using CuKa radiation, an accelerating voltage of 40 KeV/30 mA, a step size of 0.05° 2-theta and a data acquisition time of 2.0 seconds per step. Sample 1 showed strong peaks typical of a crystalline sample. The most intense paclitaxel peak was located at 5.1° 2-theta. Sample 2 showed broad humps typical of amorphous material. Sample 3 showed largely the broad humps of Sample 2, but in addition, the peak at 5.1° 2-theta of paclitaxel was visible. Sample 4, the formulated paclitaxel showed no evidence of crystallinity characteristic of paclitaxel and appeared identical to Sample 2, indicating the presence of substantially amorphous pharmacologically active agent in the formulated sample.

The amorphous nature of the nanoparticles produced according to the invention stands in direct contrast to the products produced by other methods described in the art for producing nanoparticles. For example, the use of grinding techniques, as described in U.S. Pat. No. 5,145,684 (Liversidge et al.), and as described by Liversidge-Merisko et al., *Pharmaceutical Research* 13 (2):272-278 (1996), produces a substantially crystalline product.

EXAMPLE 13

Preparation of Nanoparticles of Cyclosporine (Capsorine I.V.) by High Pressure Homogenization 30 mg cyclosporine is dissolved in 3.0 ml methylene chloride. The solution is then added into 27.0 ml of human serum albumin solution (1% w/v). The mixture is homogenized for 5 minutes at low RPM (Vitris homogenizer model: Tempest I.Q.) in order to form a crude emulsion, and then transferred into a high pressure homogenizer (Avestin). The emulsification was performed at 9000-40,000 psi while recycling the emulsion for at least 5 cycles. The resulting system was transferred into a Rotavap and methylene chloride was rapidly removed at 40° C., at reduced pressure (30 mm Hg), for 20-30 minutes. The resulting dispersion was translucent and the typical diameter of the resulting cyclosporine particles was 160-220 (Z-average, Malvern Zetasizer).

The dispersion was further lyophilized for 48 hours, without adding any cryoprotectant. The resulting cake could be easily reconstituted to the original dispersion by addition of sterile water or saline. The particle size after reconstitution was the same as before lyophilization.

EXAMPLE 14

Preparation of Nanodroplets of Cyclosporine (Capsorine Oral) by High Pressure Homogenization 30 mg cyclosporine is dissolved in 3.0 ml of a suitable oil (sesame oil containing 10 orange oil). The solution is then added into 27.0 ml of human serum albumin solution (1% v/w). The mixture is homogenized for 5 minutes at low RPM (Vitris homogenizer, model: Tempest I.Q.) in order to form a crude emulsion, and then transferred into a high pressure homogenizer (Avestin). The emulsification is performed at 9000-40,000 psi while recycling the emulsion for at least 5 cycles. The resulting dispersion had a typical diameter of 160-220 (Z-average, Malvern Zetasizer).

The dispersion could be used directly or lyophilized for 48 hours by optionally adding a suitable cryoprotectant. The resulting cake could be easily reconstituted to the original dispersion by addition of sterile water or saline.

B. Formation of Nanoparticles Using Sonication

Similar to the use of high shear homogenization, the use of sonication to form protein-coated nanoparticles of water insoluble pharmacologically active agents is believed to operate by crosslinking proteins through the formation of intermolecular disulfide bonds. Many of the advantages over the prior art enjoyed by the high shear homogenization techniques described above apply equally to the sonication methods described below.

With respect to the organic solvents, proteins, and non-proteinaceous polymers that may be used in the sonication method, reference is made to those components described above with respect to the high shear homogenization method. All of the same components are expected to work equally well in both methods.

This aspect of the invention will now be described in greater detail by reference to the following non-limiting examples.

EXAMPLE 15

Formulation for Inhalation of Anti-Asthmatic Drug

Anti-asthmatic pharmaceuticals have been prepared using microparticle techniques to yield effective formulations for dry powder inhalers (DPI). Starting with a steroidal drug (e.g., beclomethasone, beclomethasone dipropionate, budesonide, dexamethasone, flunisolide, triamcinolone acetonide, and the like), a dry formulation is prepared of appropriate particle size and release characteristics to ensure efficacious delivery in the respiratory system.

The formulation is prepared using sonication techniques, or homogenization in which the active drug, dissolved in solvent, is dispersed into an aqueous protein solution to form an emulsion of nanoparticles. This emulsion is then evaporated to remove solvents, leaving the active drug coated with protein in solution. This liquid sample containing the colloidal drug particles is measured by Malvern Zetasizer and gives a Z-average size of 260 nm. In a preferred embodiment, the range of sizes of these colloidal particles is about 50-1,000 nm, and more preferably about 70-400 nm.

In this liquid form, other excipients may be dissolved. Such excipients include (but are not limited to) mannitol 0.5-15% lactose 0.1-5%, and maltodextrin. At this stage, the resulting solution of active drug, protein, and excipient can be either spray-dried or lyophilized and milled to yield a dry powder. After spray-drying, the dry particle size is determined by Malvern Mastersizer as D(v.0.5) of about 1-10 μm. The preferred size range for these particles is 0.5-15 μm, with a more preferred range of 0.7-8 μm.

This spray dried powder is then mixed with an excipient carrier powder. Again, several carriers are available, including lactose, trehalose, Pharmatose 325 M, sucrose, mannitol, and the like. The size of the carrier powder is significantly larger than that of the formulated drug particles (~63-90 μm for lactose, 40-100 μm for Pharmatose).

The efficacy of the dry powder formulation is demonstrated by testing with an Andersen eight-stage cascade impactor. Results of impactor trials show a fine particle fraction (FPF) of ~60%. This indicates a highly effective release of particles, appropriately sized for respiratory deposition. This FPF is surprisingly high and is a result of the formulation composition that contains colloidal nanoparticles of the drug within larger formulation particles.

This formulation shows the applicability of microparticle and spray-dry techniques in the processing and composing of dry powder formulations for aerosol delivery via DPI. The high FPF results shown indicate an efficacious and promising approach to DPI formulations.

EXAMPLE 16

Summary of the Presently Preferred Manufacturing Process: Starting with 1 Gram Paclitaxel as the BDS Prepare a 3% HSA solution. To 51.7 ml of 25% Albutein add 379.3 ml water for injection. Mix thoroughly and filter the solution through a sterile 0.22 μm Nalgene disposable filterware. Keep at 4° C. until used.

Weigh out 1.0 g of paclitaxel in a glass bottle. Combine $CHCl_3$ and ethyl alcohol in appropriate proportions in a vial. Mix well. To the paclitaxel, add 13.33 ml of the chloroform/ethyl alcohol mixture. Agitate to ensure all paclitaxel dissolves into solution. Filter the solution through a 0.22 micron sterile Teflon filter and collect in a sterile glass bottle.

To the dissolved paclitaxel solution in the glass bottle, add the HSA solution. Use the Sentry Microprocessor mixer to mix the paclitaxel/HSA solution. When the solution is mixed, pour the contents into the chamber of the Homogenizer. Cycle the mixture through the homogenizer at a pressure until the desired particle size is obtained. Collect the homogenized sample in a sterile Kontes round bottom flask.

Attach the flask with the final sample to the Rotary evaporator. Turn on the vacuum and the rotation to maximum in the rotavapor and evaporate the organic solvent. This results in the colloidal solution of paclitaxel in human albumin. Save ~3 ml of this rotavaped sample for analysis of particle size.

Under a sterile hood, filter the colloidal solution using sterile 0.45/0.2 μm filter and collect in a sterile receiving vessel. Save ~3 ml of filtered sample for analysis by HPLC for paclitaxel concentration.

Determine the fill volume to obtain 30 mg (or other derived amount) of paclitaxel per vial. Fill the sterile filtered sample into autoclaved Wheaton 30 ml vials at approximately 17 ml each (based on assay). Close the vials with autoclaved Wheaton serum vial stoppers. Each vial should contain approximately 30 mg of paclitaxel.

Lyophilize the samples in the FTS System Stoppering tray lyophilizer using a predetermined lyophilization cycle. After the samples have been lyophilized, stopper the vials and seal the vials by crimping them with the 20 mm Wheaton aluminum tear-off caps. Label the samples appropriately. The entire process is carried out in a clean room environment under aseptic conditions.

The lyophilized samples contain residual solvent at levels <1000 ppm, and more preferably <500 ppm, or even <100 ppm.

Final Product Sterile filtration: Following removal of solvent by evaporation, the colloidal solution of paclitaxel in the flask is sterile filtered through a combination 0.45/0.2 micron sterilizing filter. The filtered solution is collected in a sterile beaker and sterile filled into 30 ml vials. Vials are then placed in the lyophilizer. Following completion of the lyophilization cycle the vials are blanketed with dry sterile nitrogen gas and stoppered under the nitrogen blanket.

It is of note that high pressure homogenization processes are utilized to rupture and kill bacterial and other cells to extract their contents.

EXAMPLE 17

Preparation of Protein Shell Containing Oil

Three ml of a USP (United States Pharmacopia) 5% human serum albumin solution (Alpha Therapeutic Corporation) were taken in a cylindrical vessel that could be attached to a sonicating probe (Heat Systems, Model XL2020). The albumin solution was overlayered with 6.5 ml of USP grade soybean oil (soya oil). The tip of the sonicator probe was brought to the interface between the two solutions and the assembly was maintained in a cooling bath at 20° C. The system was allowed to equilibriate and the sonicator turned on for 30 seconds. Vigorous mixing occurred and a white milky suspension was obtained. The suspension was diluted 1:5 with normal saline. A particle counter (Particle Data Systems, Elzone, Model 280 PC) was utilized to determine size distribution and concentration of oil-containing protein shells. The resulting protein shells were determined to have a maximum cross-sectional dimension of about 1.35±0.73 microns, and the total concentration determined to be ~$10^9$ shells/ml in the original suspension.

As a control, the above components, absent the protein, did not form a stable miocroemulsion when subjected to ultrasonic irradiation. This result suggests that the protein is essential for formation of microspheres. This is confirmed by scanning electron micrograph and transmission electron micrograph studies as described below.

EXAMPLE 18

Preparation of Polymeric Shells Containing Dissolved Paclitaxel

Taxol was dissolved in USP grade soybean oil at a concentration of 2 mg/ml. 3 ml of a USP 5% human serum albumin solution was taken in a cylindrical vessel that could be attached to a sonicating probe. The albumin solution was overlayered with 6.5 ml of soybean oil/Taxol solution. The tip of the sonicator probe was brought to the interface between the two solutions and the assembly was maintained in equilibrium and the sonicator turned on for 30 seconds. Vigorous mixing occurred and a stable white milky suspension was obtained that contained protein-walled polymeric shells enclosing the oil/Taxol solution.

In order to obtain a higher loading of drug into the crosslinked protein shell, a mutual solvent for the oil and the drug (in which the drug has a considerably higher solubility) can be mixed with the oil. Provided this solvent is relatively non-toxic (e.g., ethyl acetate), it may be injected along with the original carrier. In other cases, it may be removed by evaporation of the liquid under vacuum following preparation of the polymeric shells.

It is recognized that several different methods may be employed to achieve the physical characteristics of the invention formulation. The biological properties associated with this formulation of higher local concentrations at specific organ sites (prostate, lung, pancreas, bone, kidney, heart) as well as lower toxicities (increased LD50, decreased myelosuppression, decreased cerebral toxicity) associated with higher efficacies is independent of the method of manufacture.

EXAMPLE 19

Preparation of Nanoparticles by Sonication 20 mg paclitaxel is dissolved in 1.0 ml methylene chloride. The solution is added to 4.0 ml of human serum abumin solution (5% w/v). The mixture is homogenized for 5 minutes at low RPM (Vitris homogenizer, model: Tempest I.Q.) in order to form a crude emulsion, and then transferred into a 40 kHz sonicator cell. The sonicator is performed at 60-90% power at 0 degree for 1 min (550 Sonic Dismembrator). The mixture is transferred into a Rotary evaporator, and methylene chloride is rapidly removed at 40° C., at reduced pressure (30 mm Hg), for 20-30 minutes. The typical diameter of the resulting paclitaxel particles was 350-420 nm (Z-average, Malvern Zetasizer).

The dispersion was further lyophilized for 48 hrs without adding any cryoprotectant. The resulting cake could be easily reconstituted to the original dispersion by addition of sterile water or saline. The particle size after reconstitution was the same as before lyophilization.

EXAMPLE 20

In Vivo Biodistribution of Crosslinked Protein Shells Containing a Fluorophore

To determine the uptake and biodistribution of liquid entrapped within protein polymeric shells after intravenous injection, a fluorescent dye (rubrene, available from Aldrich) was entrapped within a human serum albumin (HSA) protein polymeric shell and used as a marker. Thus, rubrene was dissolved in toluene, and albumin shells containing toluene/rubrene were prepared as described above by ultrasonic irradiation. The resulting milky suspension was diluted five times in normal saline. Two ml of the diluted suspension was then injected into the tail vein of a rat over 10 minutes. One animal was sacrificed an hour after injection and another 24 hours after injection.

100 micron frozen sections of lung, liver, kidney, spleen, and bone marrow were examined under a fluorescent microscope for the presence of polymeric shell-entrapped fluorescent dye or released dye. At one hour, the majority of the polymeric shells appeared to be intact (i.e., appearing as brightly fluorescing particles of about 1 micron diameter), and located in the lungs and liver. At 24 hours, the dye was observed in the liver, lungs, spleen, and bone marrow. A general staining of the tissue was also observed, indicating that the shell wall of the polymeric shells had been digested, and the dye liberated from within. This result was consistent with expectations and demonstrates the potential use of invention compositions for delayed or controlled release of an entrapped pharmaceutical agent such as Taxol.

EXAMPLE 21

Toxicity of Polymeric Shells Containing Soybean Oil (SBO)

Polymeric shells containing soybean oil were prepared as described in Example 15. The resulting suspension was diluted in normal saline to produce two different solutions, one containing 20% SBO and the other containing 30% SBO.

Intralipid, a commercially available TPN agent, contains 20% SBO. The $LD_{50}$ for Intralipid in mice is 120 ml/kg, or about 4 ml for a 30 g mouse, when injected at 1 cc/min.

Two groups of mice (three mice in each group; each mouse weighing about 30 g) were treated with invention composition containing SBO as follows. Each mouse was injected with 4 ml of the prepared suspension of SBO-containing polymeric shells. Each member of one group received the suspension containing 20% SBO, while each member of the other group received the suspension containing 30% SBO.

All three mice in the group receiving the suspension containing 20% SBO survived such treatment, and showed no gross toxicity in any tissues or organs when observed one week after SBO treatment. Only one of the three mice in the group receiving suspension containing 30% SBO died after injection. These results clearly demonstrate that oil contained within polymeric shells according to the present invention is not toxic at its $LD_{50}$ dose, as compared to a commercially available SBO formulation (Intralipid). This effect can be attributed to the slow release (i.e., controlled rate of becoming bioavailable) of the oil from within the polymeric shell. Such slow release prevents the attainment of a lethal dose of oil, in contrast to the high oil dosages attained with commercially available emulsions.

EXAMPLE 22

In Vivo Bioavailability of Soybean Oil Released from Polymeric Shells

A test was performed to determine the slow or sustained release of polymeric shell-enclosed material following the injection of a suspension of polymeric shells into the blood stream of rats. Crosslinked protein (albumin) walled polymeric shells containing soybean oil (SBO) were prepared by sonication as described above. The resulting suspension of oil-containing polymeric shells was diluted in saline to a final suspension containing 20% oil. Five ml of this suspension was injected into the cannulated external jugular vein of rats over a 10 minute period. Blood was collected from these rats at several time points following the injection and the level of triglycerides (soybean oil is predominantly triglyceride) in the blood determined by routine analysis.

Five ml of a commercially available fat emulsion (Intralipid, an aqueous parenteral nutrition agent containing 20% soybean oil, 1.2% egg yolk phospholipids, and 2.25% glycerin) was used as a control. The control utilizes egg phosphatide as an emulsifier to stabilize the emulsion. A comparison of serum levels of the triglycerides in the two cases would give a direct comparison of the bioavailability of the oil as a function of time. In addition to the suspension of polymeric shells containing 20% oil, 5 ml of a sample of oil-containing polymeric shells in saline at a final concentration of 30% oil was also injected. Two rats were used in each of the three groups. The blood levels of triglycerides in each case are tabulated in Table 1, given in units of mg/dl.

TABLE 1

| GROUP | SERUM TRIGLYCERIDES (mg/dl) | | | | | |
|---|---|---|---|---|---|---|
| | Pre | 1 hr | 4 hr | 24 hr | 48 hr | 72 hr |
| Intralipid Control (20% SBO) | 11.4 | 941.9 | 382.9 | 15.0 | 8.8 | 23.8 |
| Polymeric Shells (20% SBO) | 24.8 | 46.7 | 43.8 | 29.3 | 24.2 | 43.4 |
| Polymeric Shells (30% SBO) | 33.4 | 56.1 | 134.5 | 83.2 | 34.3 | 33.9 |

Blood levels before injection are shown in the column marked 'Pre'. Clearly, for the Intralipid control, very high triglyceride levels are seen following injection. Triglyceride levels are then seen to take about 24 hours to come down to preinjection levels. Thus the oil is seen to be immediately available for metabolism following injection.

The suspension of oil-containing polymeric shells containing the same amount of total oil as Intralipid (20%) show a dramatically different availability of detectible triglyceride in the serum. The level rises to about twice its normal value and is maintained at this level for many hours, indicating a slow or sustained release of triglyceride into the blood at levels fairly close to normal. The group receiving oil-containing polymeric shells having 30% oil shows a higher level of triglycerides (concomitant with the higher administered dose) that falls to normal within 48 hours. Once again, the blood levels of triglyceride do not rise astronomically in this group, compared to the control group receiving Intralipid. This again, indicates the slow and sustained availability of the oil from invention composition, which has the advantages of avoiding dangerously high blood levels of material contained within the polymeric shells and availability over an extended period at acceptable levels. Clearly, drugs delivered within polymeric shells of the present invention would achieve these same advantages.

Such a system of soybean oil-containing polymeric shells could be suspended in an aqueous solution of amino acids, essential electrolytes, vitamins, and sugars to form a total parenteral nutrition (TPN) agent. Such a TPN cannot be formulated from currently available fat emulsions (e.g., Intralipid) due to the instability of the emulsion in the presence of electrolytes.

EXAMPLE 23

Preparation of Protein-Walled Polymeric Shells Containing a Solid Core of Pharmaceutically Active Agent Another method of delivering a poorly water-soluble drug such as Taxol within a polymeric shell is to prepare a shell of polymeric material around a solid drug core. Such a 'protein coated' drug particle may be obtained as follows. The procedure described in Example 16 is repeated using an organic solvent to dissolve Taxol at a relatively high concentration. Solvents generally used are organics such as benzene, toluene, hexane, ethyl ether, chloroform, alcohol and the like. Polymeric shells are produced as described in Example 15. Five ml of the milky suspension of polymeric shells containing dissolved Taxol are diluted to 10 ml in normal saline. This suspension is placed in a rotary evaporator and the volatile organic removed by vacuum. The resultant suspension is examined under a microscope to reveal opaque cores, indicating removal of substantially all organic solvent, and the presence of solid Taxol. The suspension can be frozen and stored indefinitely and used directly or lyophilized at a later time.

Alternatively, the polymeric shells with cores of organic solvent-containing dissolved drug are freeze-dried to obtain a dry crumbly powder that can be resuspended in saline (or other suitable liquid) at the time of use. Although the presently preferred protein for use in the formation of the polymeric shell is albumin, other proteins such as α-2-macroglobulin, a known opsonin, could be used to enhance uptake of the polymeric shells by macrophage-like cells. Alternatively, molecules like PEG could be incorporated into the particles to produce a polymeric shell with increased circulation time in vivo.

C. Formation of Nanoparticles by Spontaneous Microemulsion

It is also possible to form nanoparticles without the use of sonication, high shear homegenization, or any other high-energy technique. Thus, it is possible to form a suspension (or dry powder) of essentially pure drug, if desired.

A microemulsion is a thermodynamically stable emulsion system that is formed spontaneously when all it's components are brought into contact, in the absence of the use of high shear equipment or other substantial agitation. Microemulsions are substantially non-opaque, i.e., they are transparent or translucent. Microemulsions comprise a dispersed phase, in which the typical droplet size is below 1000 Angstrom (Å), hence their optical transparency. The droplets in the microemulsion are typically spherical, though other structures such as elongated cylinders are feasible. (For further discussion see, e.g., Rosof, *Progress in Surface and Membrane Science,* 12,405, Academic Press (1975), Friberg S., *Dispersion Science and Technology,* 6, 317 (1985).)

As will be shown below, the present invention utilizes the unique characteristics of the microemulsion as a first step towards obtaining extremely small nanoparticles, after removal of the oil phase.

As described earlier, microparticles and nanoparticles can be formed by various processes, among them, the solvent evaporation method. This method is based, in principle, on formation of a simple oil in water emulsion, in the presence of surface active agent, while applying high shear forces by means of various equipment such as rotor-stator mixers, sonicators, high pressure homogenizers, colloid mills, etc. After forming such an emulsion, which contains a polymer and a drug dissolved in the dispersed oil droplets, the oil phase is removed by evaporation, typically at reduced pressure and elevated temperature, and micoparticles or nanoparticles of the dissolved drug and polymer are formed. Obviously, the size of the particles is dependent on emulsion droplet's size; the smaller the droplets, the smaller the resulting particles. Small emulsion droplets can be achieved only by applying very high energy, and even then, by using the most advanced high pressure homogenizers such as the Microfluidizer, it is not practical to achieve emulsion droplets below 75 nm. Since emulsions are inherently unstable systems, and undergo processes such as aggregation and droplets coalescence, the solvent evaporation processes for such emulsions may result in larger particles.

The new method, which overcomes the problems associated with application of the solvent evaporation method in conventional emulsions, consists of the following steps:

a. Dissolving the water insoluble drug in a solvent which has low solubility in water, and has higher vapor pressure than water. The drug is dissolved without any additional polymeric binder, although such binder can be present, in principle.

b. Mixing the solvent with a proper surfactant(s) and a water soluble cosurfactant(s).

c. Adding a suitable amount of water or aqueous solution to this mixture, thus spontaneously forming an oil-in-water microemulsion, without the use of any high shear equipment. The aqueous solution may contain electrolytes, amino acids, or any other additive which may affect the formation of the microemulsion during the first preparation stage.

d. Optionally adding a protein solution to the microemulsion.

e. Removing the solvent by evaporation at reduced pressure, thus causing precipitation of the drug in the form of extremely small amorphous nanoparticles, having a typical size below 1000 Angstroms. The particles at this stage are dispersed and stabilized in an aqueous medium which contains surfactant, cosurfactant, and optionally protective agents such as proteins, sugars, etc. Acceptable methods of evaporation include the use of rotary evaporators, falling film evaporators, spray dryers, freeze dryers, and other standard evaporation equipment typically used in industry.

f. Optionally one may remove the surfactant and cosurfactant by dialysis, ultrafiltration, adsorption, etc., thus obtaining nanoparticles which are stabilized by the protein.

g. Following evaporation of solvent, the liquid dispersion of nanoparticles may be dried to obtain a powder containing the pharmacological agent and optionally the protein, which can be redispersed into a suitable aqueous medium such as saline, buffer, water, and the like, to obtain a suspension that can be administered to a life-form, having a particle size below 1000 Angstroms. Acceptable methods of obtaining this powder are by freeze-drying, spray drying, and the like. If the conversion into a solid form is performed by lyophilization, various cryoprotectants may be added, such as manitol, lactose, albumin, carboxymethyl cellulose, polyvinylpyrolidone, maltodextrins, and/or polyethylene glycol.

These nanoparticles can be further mixed with additional excipients or matrix-forming materials, in order to obtain a drug delivery system, with high bioavailabilty, controlled release characteristics, and protection in gastric juice. The final product may be introduced to the mammals as a tablet, capsule, reconstituted liquid, or the like.

The present invention formulation has significant advantages over the previously used methods for preparation of nanoparticles and microparticles, and the use of microemulsions or "pre-microemulsion concentrate."

There are many advantages realized by using the invention process. The microemulsion is formed spontaneously, if the proper components are selected, and there is no need for high cost equipment and energy input. The droplet size is smaller about an order of magnitude than the smallest emulsion droplets obtained by high shear equipment, and therefore extremely small nanoparticles can be obtained. The microemulsion is thermodynamically stable, and therefore the usual problems which are associated with emulsion instability (and thus a time dependence of the size of the resulting particles) will be prevented. The whole process is much more simple than the conventional emulsion-solvent evaporation method, and less sensitive to various parameters. Since only simple mixing is involved in the process, the upscaling to large production volumes is very simple, compared to emulsification with equipment such as high shear homogenizer. Since the particle size obtained by the new process is so small, an order of magnitude less than the pore size of membranes used for sterile filtration, the sterilization process is very effective, without problems associated with membrane blockage, such as increased filtration pressure, and high drug loss during the filtration process. Since there are no high shear forces in the emulsification process, there is no increase in temperature during emulsification, and therefore even temperature-sensitive drugs can be processed by the new invention method. The drug in the liquid formulation of the present invention has increased chemical stability because it contains dispersed nanoparticles compared to conventional microemulsions that contain dispersed nanodroplets, i.e., more chemical reactions take place in liquid state (microdroplet) versus solid state (nanoparticle). The present invention has increased chemical stability as a dry formulation compared to conventional microemulsions that are liquids as the continuous microemulsion phase. The solid formulation enables inclusion of the drug in various solid dosage forms, such as tablets, granules and capsules, compared to conventional microemulsions or "pre-microemulsion concentrates," which are present in a liquid form. The very narrow size distribution, combined with very low average particle size, ensures increased adsorption of the drug, in a manner more uniform than microparticles and nanoparticles prepared by conventional methods, thus, increased bioavailability is expected.

Although the examples presented in the following section refer to two water insoluble molecules, the pharmacological agents contemplated to be useful in the preparation of nanoparticles include but are not limited to drugs, diagnostic agents, agents of therapeutic value, nutritional agents, and the like. A non-limiting list of drug categories and compounds include but are not limited to all of the compounds listed above for use in the high shear homogenization aspect of the invention.

The solvents described in the following examples are toluene and butyl acetate, however, any solvent or solvent mixture which is capable of dissolving the required drug will be suitable for use in the invention process, provided that a proper microemulsion can be formed prior to removal of the solvent. Such solvents can be chloroform, methylene chloride, ethyl acetate, butyl acetate, isobutylacetate, propyl acetate, tert-butylmethyl ether, butanol, propylen glycol, heptane, anisol, cumene, ethyl formate ethanol, propanol, tetrahydrofuran, dioxane, acetonitrile, acetone, dimethyl sulfoxide, dimethyl formamide, methyl pyrrolidinone, soybean oil, coconut oil, castor oil, olive oil, safflower oil, cottonseed oil, alcohols C1-C20, esters C2-C20, ketones C3-C20, polyethylene glycols, aliphatic hydrocarbons, aromatic hydrocarbons, halogenated hydrocarbons, d-limonene, combinations thereof, and the like.

The protein (or a mixture of several proteins) used in this process should be such that does not precipitate during the initial mixing or during the evaporation stage. There are many such proteins, including albumins (e.g., BSA HSA, egg), gelatin, collagen, IgG, various enzymes, lactoglobulin, casein, soy proteins, and the like.

The surfactants utilized in this invention should be capable of spontaneously forming oil-in-water microemulsions, in the presence of a suitable cosurfactant and solvent, without causing precipitation of the drug or the protein (if present). The surfactants can be nonionic (Tween, Span, Triton, Pluronic, polyglycerol esters, and the like), anionic (SDS, cholates and deoxycholates, fatty acid soaps, and the like), cationic (cetyltrimethyl ammonium chloride, and the like) or zwitterionic (lecithin, amino acids, and the like)

The cosurfactant should have the ability to spontaneously form microemulsions with the selected surfactants, without causing precipitation of the dissolved drug molecules (or protein, if present), and without inducing formation of large crystalline material. The cosurfactants can be either water soluble or oil soluble, such as butanol, propylene glycol, benzyl alcohol, propanol, and the like.

The conversion of the liquid dispersion of the nanoparticles via lyophilization may require the addition of cryoprotecting agents, such as mannitol, lactose, amino acids, proteins, polysaccharides, and the like.

It is clear that the principles described in this invention can be applied in several variations of the process, for example:

1. The formation of the drug particles may be induced by dilution of the microemulsion in a proper solvent, in which the solvent is miscible. For example, if the solvent has a low solubility in water, it would be possible to dilute the microemulsion to such an extent that the solvent will be below it's solubility limit in water.

2. The solvent and optionally the surfactant and cosurfactant can be removed by using a selective extractant which does not dissolve the drug.

3. The surfactant and cosurfactant may be removed by ultrafiltration, while using filters having a cut-off below that of the MW of the protein. Simple dialysis is also an option.

4. The formulation may contain only components which are acceptable for the intended use of the final formulation (whether oral, IV, topical, etc.), thus there is no need for their removal.

5. Similarly, cosurfactants that can remain in the final product, such as glycerol, benzyl alcohol, etc, may be used.

6. The addition of various water soluble molecules which may affect the phase diagram of the microemulsion (electrolytes, ethanol etc.) is possible, thus controlling the ratio between the various components to give the optimal drug load.

7. The spontaneous emulsification step may be performed at a temperature other than room temperature, in order to affect the phase diagram (and the component proportions that leads to formation of a microemulsion). In particular, it could be possible to use the temperature effect (in ethoxylated surfactants) to change the system from an oil-in-water to a water-in-oil microemulsion.

8. It is possible to add other components to the solvent phase, in order to affect the bioavailability of the drug. In particular, addition of an oil such as Soybean oil, to enhance oral absorption, and to protect the drug from chemical and enzymatic degradation is preferred.

9. Similarly, the addition of a matrix-forming polymer (such as PVP) to the solvent, together with the drug may be done.

10. The stabilization and solid-form properties may be altered by the addition of a water soluble polymer other than the protein (CMC, gums, and the like) to the external aqueous phase of the microemulsion.

11. The flow properties of the resulting solid form powder may be altered by addition of colloidal particles (e.g. silica) as a filler, or addition of reconstitution/anti-agglomeration aids.

12. The same principles described in this invention may be applied to form water soluble particles, while performing the emulsification stage in the composition range in which a water-in-oil microemulsion is formed. The process can be used, for example to form extremely small protein nanoparticles.

EXAMPLE 22

Preparation of Nanoparticles of Cyclosporin A 115 mg Cyclosporin A are dissolved in 1 mL butyl acetate, and mixed with 2 grams of a 4:1 solution of Triton X-100:n-Butanol. A clear system is obtained. 10 g water is added dropwise, while slightly shaking. A clear oil-in-water microemulsion is obtained. 10 g of 1% casein solution is added, while slightly shaking. The system becomes slightly turbid. The butyl acetate is removed in a rotovap, at 40° C., 80 mm Hg. The system becomes completely clear.

The particle size was measured by photon correlation spectroscopy. It was found that the Z-average size is 25-33 nm, while the size by number or volume distribution is only 9 nm. No particles were observed under optical microscope, nor under polarized light. This result indicates the absence of crystalline particles.

The liquid dispersion of these nanoparticles was lyophilized, after adding lactose (2% w/w).

A white, solid material was obtained, which, upon reconstitution in water, yielded a clear system, similar to that prior to lyophilization. The particle size in this reconstituted sample was very similar to that of the original formulation, Z-average about 40 nm, and diameter by volume and number distribution between 10-12 nm.

EXAMPLE 25

Preparation of Nanoparticles of Cyclosporin A 119 mg of Cyclosporin A are dissolved in butyl acetate, and mixed with 2 grams of a 4:1 solution of Triton X-100:propylene glycol. A clear system is obtained. 7 g water is added dropwise, while slightly shaking. A clear oil-in-water microemulsion is obtained. 7 g of 1% casein solution is added, while slightly shaking. The system becomes slightly turbid. The sample is diluted 1:1 with water, prior to solvent evaporation. The butyl acetate is removed in a rotovap, at 40° C., 80 mm Hg. The system becomes completely clear. This process also yielded extremely small nanoparticles: Z-average 45 nm, and diameter by volume and number distribution is 11 nm.

The liquid dispersion of these nanoparticles was lyophilized, after adding lactose (2% w/w).

A white, solid material was obtained, which, upon reconstitution in water, yielded a clear system, similar to that prior to lyophilization. The particle size in this reconstituted sample was close to that of the original formulation, Z-average about 25 nm, and diameter by volume and number distributions between 9-11 nm.

EXAMPLE 26

Cyclosporine Nanoparticles

Microemulsions were made with the following compositions: 50 mg Cyclosporine, 0.5 g butylacetate, 3.04 g Tween 80:propyleneglycol (1:1), and 6.8 g water. The microemulsion was evaporated to give a clear liquid containing mg/ml of cyclosporine. In a control experiment, performed with the above components by simple mixing, but without butylacetate, even after 17 hours, cyclosporin was not dissolved.

There are several possibilities for surfactants, including polysorbates (Tween), sorbitan esters (span), sucrose esters, lecithin, monodiglycerides, polyethylene-polypropylene block copolymers (pluromics), soaps (sodium stearate, etc.), sodium glycolate bile salts, ethoxylated castor oil, sodium stearoyl-lactylate, ethoxylated fatty acids (myrj), ethoxylated fatty alcohols (Brij), sodium dodecyl sulphate (SDS), and the like. Also, in general, biopolymers such as starch, gelatin, cellulose derivatives etc. may be used. Also for oral applications, all acceptable food grade surfactants may be used as well as surfactants presented in McCutcheon Handbook of Surfactants or CTFA Index. Possible cosolvents or cosurfactants for the microemulsion include propylene glycol, ethanol, glycerol, butanol, oleic acid, and the like.

EXAMPLE 27

Preparation of Nanoparticles of BHT 110 mg butylated hydroxy toluene (BHT) is dissolved in 1 ml toluene, and mixed with 2 ml 4:1 solution of Triton X-100: n-Butanol. 32 g of 1% casein solution was added, and a microemulsion was spontaneously formed. The microemulsion was evaporated under reduced pressure, 80 mm Hg, at 40° C., until it became clear. The size of the resulting particles is: Z-average 30 nm, diameter by volume and number distribution is 16 and 15 nm, respectively.

EXAMPLE 28

Preparation of Nanoparticles of BHT

A process similar to that described in example 24 was performed, while using water instead of casein solution. After evaporation at 40° C., 80 mm Hg, the system became clear, having a Z-average size of ~10 nm.

EXAMPLE 29

Preparation of Nanoparticles of Paclitaxel 30 mg of paclitaxel were dissolved in 2 ml butyl acetate, and added to 4 grams of 4:1 Triton x-100:propylene glycol. 40 ml water were added, and the system was slightly turbid. After evaporation, the system became completely clear. Z-average size was 6 nm, size by volume and numbered distribution was 7-9 nm. The same size was measured after one day at 4° C.

D. Miscellaneous Examples Relevant to All Methods of Nanoparticle Formation

EXAMPLE 30

Identification of Microemulsion Phase Diagrams

Compositions were identified which yield microemulsions, and that may be utilized to obtain nanoparticles by the solvent evaporation method. These compositions should contain a water miscible solvent capable of dissolving hydrophobic molecules, an aqueous solution as the continuous medium, surfactants, and possibly cosurfactants.

Microemulsions of butyl acetate in water can be formed at various compositions which are described by phase diagrams (butyl acetate is classified as solvent with high acceptable residual concentration in the final product). Furthermore, both surfactant and cosurfactant are used in food and pharmaceutical applications: Tween 80 (ethoxylated sorbitan monooleate) and propylene glycol. Preliminary experiments were conducted by using BHT as a model hydrophobic molecule, yielding dispersions of particles in the size range of 20-50 nm. After filtration by 0.2 μm filters, about 100% of the BHT passed the membrane.

Phase diagrams of various combinations of surfactant/cosurfactant were obtained by vortexing the solvent with a mixture of surfactant/cosurfactant (prepared prior to the mixing with the solvent, at various ratios), followed by dropwise addition of water. The turbidity of the various compositions along the "water line" was observed and the compositions which yielded translucent systems were further analyzed by light scattering. By using various ratios of solvent-surfactant/cosurfactant, the areas in the phase diagrams which yielded microemulsions were identified (only a small number of the selected components yielded microemulsions). The same procedure was used for systems in which BHT was dissolved in butyl acetate prior to conducting the phase diagram experiments.

The "filterability" of the microemulsion and nanoparticles which contain the BHT, was evaluated by comparing the UV absorption spectra before and after 0.2 μm filtration. The nanoparticles were obtained by vacuum evaporation of butyl acetate (60 mm Hg, 40 C). It should be emphasized that throughout the whole process no high shear equipment was used.

The microemulsion systems were identified which could be useful for oral delivery. n-Butyl acetate was chosen as a solvent. The following surfactants and cosurfactants were evaluated at various ratios:

| | |
|---|---|
| Tween 80:Glycerol | 5:1 |
| Tween 80:Glycerol | 4:1 |
| Tween 80:Glycerol | 3:1 |
| Tween 80:Glycerol | 2:1 |
| Tween 80:Glycerol | 1:1 |
| Span 80:Glycerol | 4:1 |
| Span 80:Glycerol | 3:1 |
| Tween 80:Propylene glycol | 4:1 |
| Tween 80:Propylene glycol | 3:1 |
| Tween 80:Propylene glycol | 2.5:1 |
| Tween 80:Propylene glycol | 1.5:1 |
| Tween 80:Propylene glycol | 1:1 |
| Tween 80:Propylene glycol | 1:2 |
| ((Tween 80 + Span 80) 7:1):Propylene glycol | 3.5:1 |
| ((Tween 80 + Span 80) 7:1):Propylene glycol | 1:1 |
| ((Tween 80 + Span 80) 8:1):Propylene glycol | 4:1 |
| ((Tween 80 + Span 80) 5:1):Propylene glycol | 1:1 |
| Tween 80:((Propylene glycol + Glycerol) 1:1.2) | 2:1 |

A suitable composition was found to be as follows: Tween 80 as a surfactant and propylene glycol as a cosurfacant at ratio 1:1. The full phase diagram was evaluated for the system n-butyl acetate, Tween 80:propylene glycol 1:1, water. Two additional solvents were tested: sec-butyl acetate and tert-butyl acetate. The phase diagrams for these systems were the same as for that with n-butyl acetate. The system n-butyl acetate, Tween 80:propylene glycol 1:1, water was evaluated further.

The measurement of particle size for the sample 7% butyl acetate, 30% surfactant/PG, 63% water was performed. Z average of about 20 nm was found. The nanoparticles formation process was conducted for a water insoluble dye, Sudan III, at concentration of about 10 mg in 1 g butyl acetate (5% butyl acetate, 23% surfactant/PG, 72% water). Particle size of about 17 nm was found. The nanoparticles formation process was also conducted for BHT at concentration 100 mg in 1 g butyl acetate. The phase diagram for this system was determined. Particle size of about 20-50 nm was found depending on the composition.

Control experiments with Sudan III and BHT were conducted. 14.4 g of water was added to 10 mg Sudan III and 4.6 g of surfactant/PG was added to the mixture. The sample was stirred for 24 hr with magnetic stirrer. Dissolution of Sudan III was observed. However, when the same experiment was performed with BHT (100 mg BHT in 9 g water and 4.3 g of surfactant/PG) no dissolution of BHT was observed. At this stage evaporation was performed (temperature 40° C., pressure about 60 mm Hg). The measurement of particle size for the samples was performed before and after evaporation. Z average of about 20-50 nm, and 30 nm was found for the samples before evaporation and after evaporation, respectively.

The samples after evaporation were filtered through 0.2 µm filters, and the concentration of the BHT before and after filtration was measured by UV absorption. It was found that there is no difference between the two samples. This result is obviously an indication of the very small size of the BHT nanoparticles.

Two samples were prepared (the composition of these samples: sample no. 1: 4% butyl acetate; 14% surfactant/PG; 80% water; sample no 2: BHT 123 mg/g butyl acetate; 5% butyl cetate; 18% surfactant/PG; 77% water).

EXAMPLE 31

Alternatives in Choice of Process Equipment

Process equipment used to produce the current batches will be scaled-up for clinical manufacture. There are several alternatives available in the choice of larger scale equipment for Capxol™ production. Some of these alternatives are listed below:

| Equipment Category | Equipment Options |
|---|---|
| Premixer | Blade Mixer, Rotostator Mixer |
| High Pressure Equipment | High Pressure Homogenizers (Avestin, Microfluidics, Stansted), Sonicators (Heat Systems) |
| Solvent Removal Equipment | Rotary Evaporators, Continuous Flow Evaporators, Wiped Film Evaporators, Flash Evaporators, Recirculting Concentrators, Ultra filtration |
| Dehydration Equipment | Lyophilizers, Spray Dryers |

EXAMPLE 32

Intravenous Delivery Systems Formulated from a Variety of Materials

The materials used for the preparation of intravenous delivery systems may be polymeric (e.g., polyethylene, polyvinyl, polypropylene tubing, and the like), or glass. Standard medical grade tubing is known to contain hydrophobic moieties on the inner surfaces thereof. These moieties are thus available to come in contact with the injection solution. Indeed, such tubing is specifically tailored, as are the catheters, to present hydrophobic moieties in contact with the treatment solution so as to reduce the absorption of aqueous material to the tubing. However, any hydrophobic moieties in the treatment solution will likely bind to both the catheter tubing and other components of the delivery system. As a result, a substantial portion of a hydrophobic pharmacologically active agent can become sequestered in the inner walls of the tubing catheter and delivery vessel. Consequently, the dosing of hydrophobic pharmacologically active agents can be erratic, since a substantial portion of the active agent can become absorbed to the walls of the tubing. In critical therapeutic treatments, where the hydrophobic pharmacologically active agent is used to treat a disease, a significant reduction in the effective dose of active agent can lead to a therapeutic failure. The failure is particularly striking when employing therapeutic moieties which require that the active agent be present above a certain level, yet the therapeutic window is narrow.

A novel method for the intravenous introduction of a hydrophobic pharmacologically active agent has now been developed. By protecting the hydrophobic moieties of the active agent, through association with the hydrophobic moieties of a biocompatible coating (e.g., albumin), the propensity of the active agent to become attached to the tubing is dramatically reduced. Thus, the present invention enables the use of highly hydrophobic drugs, in combination with standard medical grade polymers and hydrophobic glasses, in which the drug is protected and therefore not absorbed onto the surface. The invention method comprises placing a protective coating of a biocompatible polymer (e.g., albumin) around the hydrophobic drug and placing the resulting composition in a hydrophobic polymeric delivery system. The invention methods are therefore capable of improving the delivery of a variety of hydrophobic therapeutics.

EXAMPLE 3

HPLC Analysis of Paclitaxel

Chromatographic System:
HPLC: Shimadzu LC-10AS Solvent Delivery System
  Shimadzu SIL-10A Auto Injector
  Shimadzu SCL-10A System Controler
  Shimadzu SPD-M10V Diodearray Detector
  Shimadzu CTO-10A Column Oven
Column: Curosil-PFP, 5 μm, 4.6 mm×25 cm, Phenomenex; or C-18
Mobile Phase: water/acetonitrile 65:45
Flow Rate: isocratic, 1.0 ml/min
Detection: 228 nm
Identity of Paclitaxel Bulk Drug Substance (BDS)

The paclitaxel BDS and the paclitaxel standard (99.9%, Hauser Chemical Research, INC., Lot 1782-105-5) were quantitatively dissolved in acetonitrile and injected into the HPLC separately. 10 μl of 1.00 mg/ml paclitaxel BDS and 10 μl of 2.07 mg/ml standard paclitaxel were injected. The retention time of the dominant peak of paclitaxel BDS matches the retention time of the paclitaxel standard from Hauser.
Potency of Paclitaxel BDS The paclitaxel BDS and standard paclitaxel were injected into the HPLC as described above. The potency of paclitaxel was derived based on the peak area ratio of the paclitaxel BDS over the standard paclitaxel and the known potency of the standard paclitaxel.
Impurity Profile of Paclitaxel BDS The chromatographic system described above is capable of providing a high resolution of taxanes. 10-20 μl of 1.0 mg/ml paclitaxel BDS in acetonitrile which falls within the linear response range of our HPLC system was injected into the HPLC. The impurity profile was determined by the relative peak area.
Assay of Potency of Paclitaxel in Capxol™

The standard solutions (60, 100, 120, 140 and 160 ug/mL) were prepared by quantitatively dissolving paclitaxel BDS in 3% HSA. The Capxol™ samples were diluted in saline to ~100 μg/ml in paclitaxel concentration. The standard solutions and Capxol™ samples were spiked with cephalomannine as an internal standard followed by Solid Phase Extraction or Liquid Phase Extraction (see below). Separately inject equal volumes (20-30 μl) of the standard preparations and Capxol™ sample preparations into the HPLC to measure the peak response ratio between paclitaxel and the internal standard cephalomannine. A calibration curve was generated by the ordinary least square regression on the results from the standard injections. The potency of paclitaxel in Capxol™ is determined by comparing the peak response ratio of the sample injections with the standard injections.
Impurity Profile of Paclitaxel in Capxol™

Capxol™ was subjected to the Solid Phase Extraction or Liquid Phase Extraction (see below) before injection into the HPLC. 30 μl of ~1 mg/ml paclitaxel extracted from Capxol™ was injected to investigate the impurity profile as above.

Solid Phase Extraction

A Capxol™ sample is reconstituted to approximately 100 μg/ml in saline. A solid phase extraction column, Bond-Elut (C-18) is conditioned with water. The column is loaded with the sample which is pulled through the column using a vacuum. The column is then washed with water followed by elution of paclitaxel with acetonitrile. The eluate containing extracted paclitaxel in acetonotrile is injected on the HPLC.
Liquid Phase Extraction A Capxol™ sample is reconstituted to approximately 100 μg/ml in saline. To approximately 200 μl of this sample is added 800 μl of acetonitrile. The mixture is vortexed for seconds and then centrifuged at 3,000 g for 5 minutes. The supernatant is removed and collected. The pellet is resuspended in 200 μl of saline and the extraction step repeated. The second supernatant is pooled with the first. The pooled extract is concentrated by evaporation followed by injection on the HPLC.

EXAMPLE 34

Particle Size Distribution by Photon Correlation Spectroscopy (PCS)

The particle size distribution of reconstituted Capxol™ was analyzed by photon correlation spectroscopy (PCS) on the Malvern Zetasizer, Malvern Instruments Ltd. The Zetasizer was calibrated by NIST traceable Nanosphere™ Size Standards, Duke Scientific Corporation. The procedure for measuring Capxol™ particle size on the Malvern Zetasizer included setting the following parameters:
Temperature.: 20.70° C.,
Scattering angle: 90°
Refractive Index dispersant: 1.33
Wavelength: 633 nm
Visc. (Auto): 0.99
Real refractive index: 1.59
Imaginary refractive index: 0

After preparing the Zetasizer, next determine the dilution of the sample needed for a good size measurement from the kcts/sec readings (to start, aliquot 200 μl of sample into a cuvette then dilute with approximately 2 ml of 0.22 μm filter filtered distilled water). Place the cuvette into the cuvette holder inside the Zetasizer and start measurement. Once the measurement starts, the Correlator Control display will appear. From the menu, choose display rate meter. The rate should be in the medium range 100-250 kcts/sec. If the rate is either too high or too low, prepare another sample at higher or lower dilution respectively. The size of reconstituted Capxol™ was analyzed, averaged and recorded by multimodal analysis after three Auto runs. The mean particle size was 155 nm±23 nm for 25 batches of Capxol™.

EXAMPLE 35

Polymeric Shells as Carriers for Polynucleotide Constructs, Enzymes and Vaccines As gene therapy becomes more widely accepted as a viable therapeutic option (at the present time, over 40 human gene transfer proposals have been approved by NIH and/or FDA review boards), one of the barriers to overcome in implementing this therapeutic approach is the reluctance to use viral vectors for the incorporation of genetic material into the genome of a human cell. Viruses are inherently toxic. Thus, the risks entailed in the use of viral vectors in gene therapy, especially for the treatment of non-lethal, non-genetic diseases, are unacceptable. Unfortunately, plasmids transferred without the use of a viral vector are usually not incorporated into the genome of the target cell. In addition, as with conventional drugs, such plasmids have a finite half life in the body. Thus, a general limitation to the implementation of gene therapy (as well as antisense therapy, which is a reverse form of gene therapy, where a nucleic acid or oligonucleotide is introduced to inhibit gene expression) has been the inability to effectively deliver nucleic acids or oligonucleotides which are too large to permeate the cell membrane.

The encapsulation of DNA, RNA, plasmids, oligonucleotides, enzymes, and the like, into protein microcapsule shells as described herein can facilitate their targeted delivery to the liver, lung, spleen, lymph and bone marrow. Thus, in accordance with the present invention, such biologics can be delivered to intracellular locations without the attendant risk associated with the use of viral vectors. This type of formulation facilitates the non-specific uptake or endocytosis of the polymeric shells directly from the blood stream to the cells of the RES, into muscle cells by intramuscular injection, or by direct injection into tumors. In addition, monoclonal antibodies against nuclear receptors can be used to target the encapsulated product to the nucleus of certain cell types.

Diseases that can be targeted by such constructs include diabetes, hepatitis, hemophilia, cystic fibrosis, multiple sclerosis, cancers in general, flu, AIDS, and the like. For example, the gene for insulin-like growth factor (IGF-1) can be encapsulated into protein shells for delivery for the treatment of diabetic peripheral neuropathy and cachexia. Genes encoding Factor IX and Factor VIII (useful for the treatment of hemophilia) can be targeted to the liver by encapsulation into protein microcapsule shells of the present invention. Similarly, the gene for the low density lipoprotein (LDL) receptor can be targeted to the liver for treatment of atherosclerosis by encapsulation into protein microcapsule shells of the present invention.

Other genes useful in the practice of the present invention are genes which re-stimulate the body's immune response against cancer cells. For example, antigens such as HLA-B7, encoded by DNA contained in a plasmid, can be incorporated into a protein shell of the present invention for injection directly into a tumor (such as a skin cancer). Once in the tumor, the antigen will recruit to the tumor specific cells which elevate the level of cytokines (e.g., IL-2) that render the tumor a target for immune system attack.

As another example, plasmids containing portions of the adeno-associated virus genome are contemplated for encapsulation into protein microcapsule shells of the present invention. In addition, protein microcapsule shells of the present invention can be used to deliver therapeutic genes to CD8+ T cells, for adoptive immunotherapy against a variety of tumors and infectious diseases.

Protein shells of the present invention can also be used as a delivery system to fight infectious diseases via the targeted delivery of an antisense nucleotide, for example, against the hepatitis B virus. An example of such an antisense oligonucleotide is a 21-mer phosphorothioate against the polyadenylation signal of the hepatitis B virus.

Protein shells of the present invention can also be used for the delivery of the cystic fibrosis transmembrane regulator (CFTR) gene. Humans lacking this gene develop cystic fibrosis, which can be treated by nebulizing protein microcapsule shells of the present invention containing the CFTR gene, and inhaling directly into the lungs.

Enzymes can also be delivered using the protein shells of the present invention. For example, the enzyme, DNAse, can be encapsulated and delivered to the lung. Similarly, ribozymes can be encapsulated and targeted to virus envelop proteins or virus infected cells by attaching suitable antibodies to the exterior of the polymeric shell. Vaccines can also be encapsulated into polymeric microcapsules of the present invention and used for subcutaneous, intramuscular or intravenous delivery.

EXAMPLE 36

Localized Treatment Of Brain Tumors And Tumors Within the Peritoneum

Delivering chemotherapeutic agents locally to a tumor is an effective method for long term exposure to the drug while minimizing dose limiting side effects. The biocompatible materials discussed above may also be employed in several physical forms such as gels, crosslinked or uncrosslinked to provide matrices from which the pharmacologically active ingredient, for example paclitaxel, may be released by diffusion and/or degradation of the matrix. Capxol may be dispersed within a matrix of the biocompatible material to provide a sustained release formulation of paclitaxel for the treatment of brain tumors and tumors within the peritoneal cavity (ovarian cancer and metastatic diseases). Temperature sensitive materials may also be utilized as the dispersing matrix for the invention formulation. Thus for example, the Capxol may be injected in a liquid formulation of the temperature sensitive materials (e.g., copolymers of polyacrylamides or copolymers of polyalkylene glycols and polylactide/glycolides and the like) which gel at the tumor site and provide slow release of Capxol. The Capxol formulation may be dispersed into a matrix of the above mentioned biocompatible polymers to provide a controlled release formulation of paclitaxel, which through the properties of the Capxol formulation (albumin associated with paclitaxel) results in lower toxicity to brain tissue as well as lower systemic toxicity as discussed below. This combination of Capxol, or other chemotherapeutic agents formulated similar to Capxol, together with a biocompatible polymer matrix, may be useful for the controlled local delivery of chemotherapeutic agents for treating solid tumors in the brain and peritoneum (ovarian cancer) and in local applications to other solid tumors. These combination formulations are not limited to the use of paclitaxel and may be utilized with a wide variety of harmacologically active ingredients including antiinfectives, immunosuppressives and other chemotherapeutics and the like.

EXAMPLE 37

Stability of Capxol™ Following Reconstitution

Lyophilized Capxol in glass vials was reconstituted with sterile normal saline to concentrations of 1, 5, 10, and 15 mg/ml and stored at room temperature and under refrigerated conditions. The suspensions was found to be homogeneous for at least three days under these conditions. Particle size measurements performed at several time points indicated no change in size distribution. No precipitation was seen under these conditions. This stability is unexpected and overcomes problems associated with Taxol, which precipitates in within about 24 hours after reconstitution at the recommended concentrations of 0.6-1.2 mg/ml.

In addition, reconstituted Capxol was stable in presence of different polymeric tubing materials such as teflon, silastic, polyethylene, tygon, and other standard infusion tubing materials. This is a major advantage over Taxol which is limited to polyethylene infusion sets and glass infusion bottles.

EXAMPLE 38

Unit Dosage Forms for Capxol™

Capxol is prepared as a lyophilized powder in vials of suitable-size. Thus a desired dosage can be filled in a suitable container and lyophilized to obtain a powder containing essentially albumin and paclitaxel in the desired quantity. Such containers are then reconstituted with sterile normal saline or other aqueous diluent to the appropriate volume at the point of use to obtain a homogeneous suspension of paclitaxel in the diluent. This reconstituted solution can be directly administered to a patient either by injection or infusion with standard i.v. infusion sets.

In addition, Capxol™ may be prepared as a frozen, ready to use solution in bottles or bags that would be thawed at the time of use and simply administered to the patient. This avoids the lyophilization step in the manufacturing process.

It is very surprising that when the invention formulation and Taxol are administered to rats at equivalent doses of paclitaxel, a much higher degree of myelosuppression results for the Taxol group compared to the invention Formulation group. This can result in lower incidences of infections and fever episodes (e.g., febrile neutropenia). It can also reduce the cycle time in between treatments which is currently 21 days. With the use of pharmaceutical compositions prepared according to the present invention, this cycle time may be reduced to 2 weeks or less allowing for more effective treatment for cancers. Thus, the use of pharmaceutical compositions prepared according to the present invention may provide substantial advantage over Taxol.

EXAMPLE 39

Oral Delivery of Drugs

Taxol is very poorly absorbed by the oral route. Particulate formulations such as Capxol may greatly enhance the uptake of drugs such as paclitaxel. In addition the invention formulations of paclitaxel prepared through the microemulsion/evaporation process are useful for oral uptake of drugs. The use of surfactants in combination with these formulations surprisingly enhance the oral bioavalability of these drugs. The use of lipids, surfactants, enzyme inhibitors, permeation enhancers, ion pairing agents, metabolism inhibitors were surprisingly found to increase the oral absorption of the invention paclitaxel formulations. Examples of ion pairing agents include but are not limited to trichloroacetate, trichloroacetate salicylate, naphthalene sulphonic acid, glycine, bis-N,N-dibutylaminoethylene carbonate, n-alkyl sulfonates, and n-alkyl sulfates. Examples of membrane permeation enhancers include but are not limited to Sodium Caprate, acyl glycerides, poloxyethylene alkyl ethers acyl carnitines, sodium cholate, sodium taurocholate, sodium taurodihydrofusidate, EDTA, sodium salicylate, sodium methoxysalicylate. A non-limiting list of surfactants and lipids that can be used for the invention formulations have been described herein.

EXAMPLE 40

Mode of Administration of Capxol and Invention Formulation of Other Drugs

The invention formulations may be administered by intravenous infusion, intravenous bolus, intraperitoneal injection, intraarterial injection, intraportal injection, hepatic embolization, intratumoral injection or implantation, intraurethral injection or iontophoresis, intramuscular injection, subcutaneous injection, intrathecal injection, inhalation of dry powder or nebulized liquid and the like.

EXAMPLE 41

Use of Capxol to Target Angiogenic Vasculature

Angiogenesis has been implicated as a causative and/or exacerbating factor in the progression of diseases such as cancer, rheumatoid arthritis, and retinopathy. We have surprisingly found that Capxol can reverse or reduce the severity of rheumatoid arthritis as well as cure tumors in animal models. It is therefore possible that Capxol has antiangiogenic activity. To make Capxol even more effective than, it is possible to target angiogenic vasculature by attaching suitable peptides to Capxol. Examples of such a peptide is RGD (arginine-glycine-aspartic acid). Many other peptides with similar activity may be attached to Capxol or other drugs prepared by the invention process for targeted therapy. The peptide/Capxol may be administered by conventional means to patients in need thereof.

EXAMPLE 42

Use of Capxol™ for Treatment of Liver Disease

End stage hepatocellular carcinoma and other cancers of the liver may be treated by administering Capxol intraportally. Embolization directly into the liver greatly enhances the dose reaching the liver. In addition much higher doses than conventional Taxol may be utilized to treat the disease mote efficiently. Also, suitable targeting agents such as proteins or peptides that localize in liver tissue may be combined with Capxol for greater therapeutic efficiency.

E. Examples Involving or Directly Pertaining to Preclinical Studies

EXAMPLE 43

Toxicity/Myelosuppression Study of Paclitaxel—Comparison of BMS Formulation and Capxol™ for Single Dose Administration Study in Rats A summary of the study is presented below.
Schedule: 1×, Single dose intravenous infusion (Day 1)
Animals: Sprague Dawley rats, 40 males, 40 females 5 rats/sex per group
Weight: 300±50 g
Study duration: 15 days
Treatment Groups: BMS (1 vehicle+3 treated groups) Capxol™ (1 vehicle*+3 treated groups)
Doses: BMS (0, 3, 6, and 9 mg/kg) Capxol™ (0, 6, 9, and 12 mg/kg)
Dose Concentration: 0.6 mg/ml (all rats)
Dose volume: BMS (15, 5, 10, 15 ml/kg) Capxol™ (20, 10, 15, and 20 ml/kg)
Infusion rate: Approximately 0.75 ml/hr (all rats)
Dose Route: I.V. infusion, tail vein
Clin obs: 1×/day
Clin Path: Days 0 (before treatment), 1, 3, 7, 11, 15. Do std. List for NCI Tox Branch
Body weights: Days −1, 1, 3, 8, and 15
(* vehicle is prepared by identical process described in manufacturing section, with the exception that the addition of paclitaxel is omitted.)

EXAMPLE 44

Pilot Myelosuppression Hematologic Toxicity Study

Figure 3:
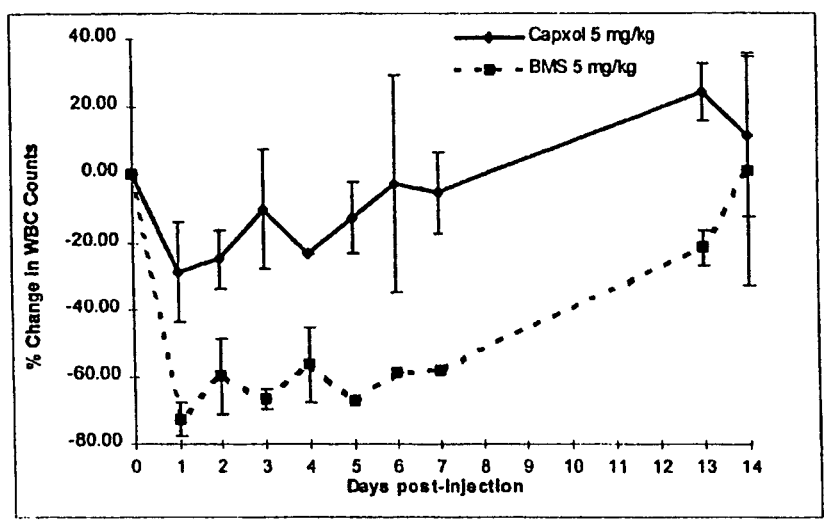
FIG. 3 provides results for a pilot myelosuppression hematologic toxicity study.

Prior to the initiation of the formal study, a pilot study with 3 rats in the Capxol™ group and 3 rats in the BMS group was performed to determine outcomes. The dose used was mg/kg with a dosing volume of 7 ml/kg. The dose was given as an intravenous bolus through the tail vein. The results of this study are summarized in the graph (see FIG. 3) which shows the percent change in WBC counts (an indicator of myelosuppression) for each formulation as a function of time.
Conclusions of Pilot Myelosuppression Study:

The data shows significantly lower WBC counts (mean+SD) in the BMS group compared to the Capxol™ group indicating a greater degree of myelosuppression for the BMS formulation (maximum WBC suppression of >70% for BMS; maximum WBC suppression of <30% for Capxol™). Analysis of the data shows a statistically significant difference ($p<0.05$) between the two groups for all data points except for day 0, 13 and 14. In addition, normal levels of WBC are recovered within 6 days in the group receiving Capxol™, while 14 days are required for recovery of normal WBC levels in the BMS group. This indicates a significantly reduced hematological toxicity for Capxol™ If similar results are seen in human clinical trials, this data may suggest that the cycle time (currently 3 weeks for Taxol®) between subsequent cycles of treatment could be significantly reduced (possibly to 2 weeks, or even 1 week or less when using Capxol™.

EXAMPLE 45

Pilot Study of Antitumor Efficacy

Figure 4:
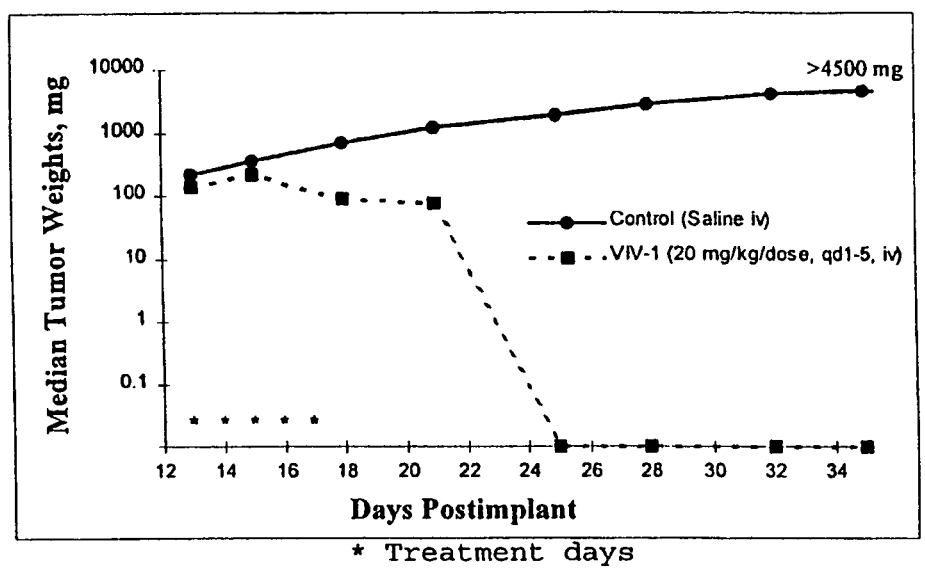
FIG. 4 provides results for a pilot study of antitumor efficacy.

Prior to the initiation of the above study, a pilot study with Capxol™ was performed to determine the target dose ranges and efficacy. The mice (n=10) were implanted subcutaneously with the MX-1 mammary tumor and the treatment was initiated when the tumor reached approximately 150-300 mg in size. This occurred by day 12 and the treatment was initiated on day 13 after initial seeding. Capxol™ was reconstituted in saline to obtain a colloidal solution of nanoparticles of paclitaxel. The tumor bearing mice (n=5) were treated with reconstituted Capxol™ at a dose of 20 mg/kg (denoted by VIV-1), given by bolus tail vein injection every day for five consecutive days. The control tumor bearing group (n=5) received only saline on the same schedule. The size of the tumors was monitored as a function of time. The control group showed a tremendous increase in tumor weight to a median of more 4500 mg and all the animals in this group were sacrificed between day 28 and day 39. The treatment group on the other hand showed remarkable efficacy and all animals had no measurable tumors by day 25. The animals in this group were all sacrificed on day 39 at which time they showed no evidence of recurrence and no evidence of tumor. The results are shown in FIG. 4.
Conclusion:

This study showed remarkable antitumor activity for Capxol™. Thus, the antitumor activity of paclitaxel is preserved the Capxol™ formulation. This study indicates that the intravenous administration of nanoparticles of paclitaxel can be as efficacious as administering the drug in the soluble form. Thus, Capxol™ shows efficacy and potent anti-tumor activity without the toxic effects seen in the approved and marketed cremaphor-containing BMS formulation.
Note: Based on literature data, and on experience of SRI (Southern Research Institute) scientists, it has been established that the maximum tolerated dose (MTD) of paclitaxel dissolved in diluent 12 (cremaphor/ethanol, which is the same diluent used in the BMS formulation) is 22.5 mg/kg for this particular strain of athymic mice. This result is obtained by dissolving paclitaxel at a much higher concentration in diluent 12 compared to the marketed BMS formulation (BMS paclitaxel, 6 mg/ml in cremaphor/ethanol). This is done to minimize the amount of cremaphor/ethanol administered to the mice to avoid vehicular toxicity. At a dose of 22.5 mg/kg, paclitaxel in diluent 12 has similar efficacy to that of Capxol™ above.

EXAMPLE 46

Treatment of Rheumatoid Arthritis in an Animal Model with Paclitaxel Nanoparticles The collagen induced arthritis model in the Louvain rat was used to test the therapeutic effect of Paclitaxel nanoparticles on arthritis. The paw sizes of the experimental animals were monitored to evaluate the seriousness of arthritis.

Figure 2:
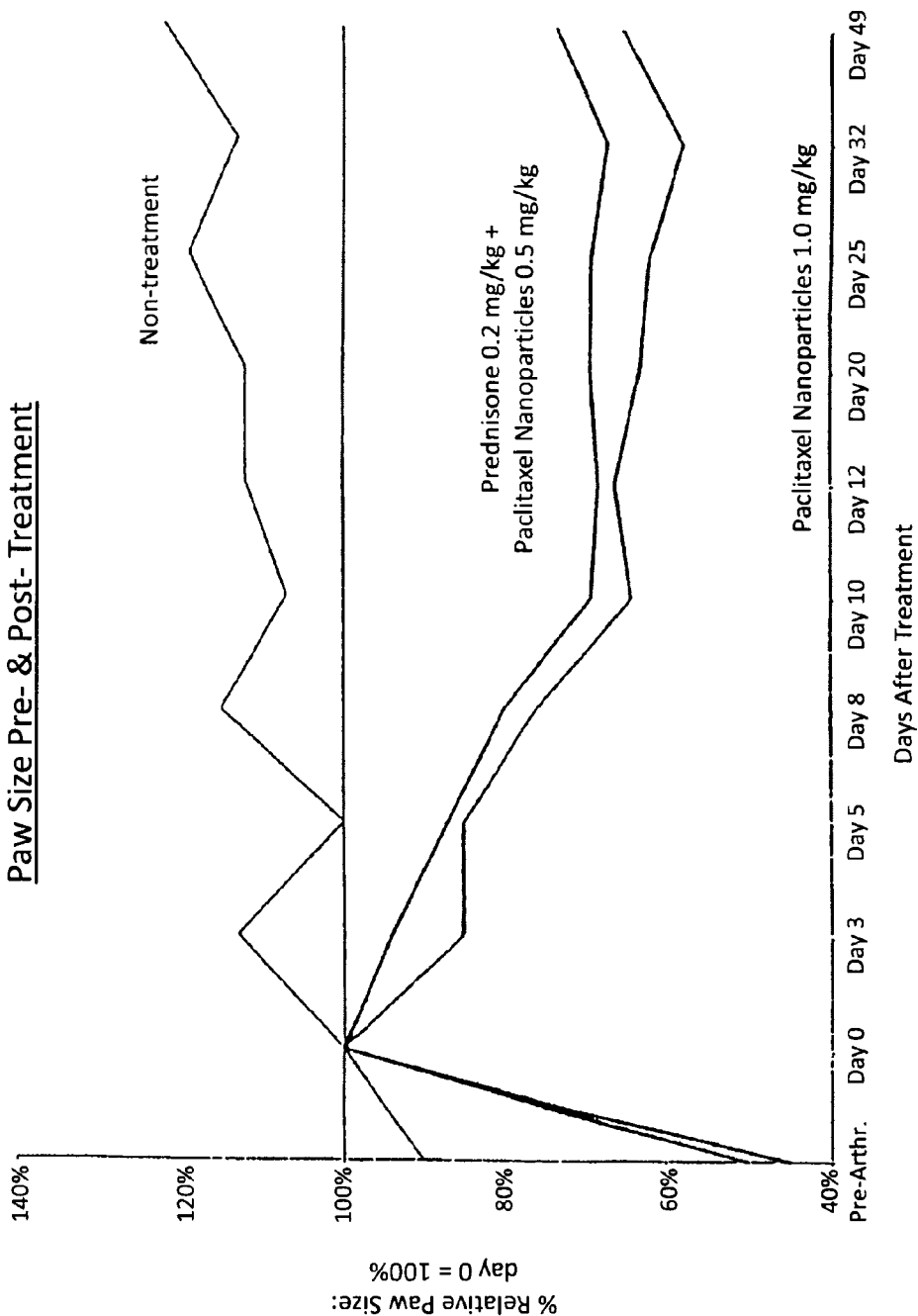
FIG. 2 presents the results of intraperitoneal administration of paclitaxel nanoparticles in rats that have developed arthritis in their paws following intradermal injection of collagen. Paw volumes are measured and indicate the severity of the disease. The paw volumes are normalized to 100% at the beginning of treatment. Day 0 represents the initiation of treatment. There are 3 groups—control group receiving saline (n=2, shown as a thin line and labelled in the figure a "non-treatment"); a first treatment group receiving paclitaxel nanoparticles at a dose of 1 mg/kg (n=4, shown as a heavy line and labelled in the figure as "paclitaxel nanoparticles 1.0 mg/kg"), and a second treatment group receiving combination therapy of paclitaxel nanoparticles at a dose of 0.5 mg/kg and prednisone at a dose of 0.2 mg/kg (n=4, shown as a heavy line and labelled in the figure as "prednisone 0.2 mg/kg+paclitaxel nanoparticles 0.5 mg/kg"). The two treatment groups show a dramatic reduction in paw volume with time, indicating a regression of arthritis, while the control group showed an increase in paw volume over the same period.

After the arthritis was fully developed (usually ~9-10 days after collagen injection), the experimental animals were divided into different groups to receive either paclitaxel nanoparticles 1 mg/kg q.o.d, or paclitaxel nanoparticles 0.5 mg/kg+prednisone 0.2 mg/kg q.o.d. (combination treatment) intraperitoneally for 6 doses, then one dose per week for three weeks. The paw sizes were measured at the beginning of treatment (day 0) and every time the drug was injected. One group received only normal saline as control. By the end of the experiment, the group receiving paclitaxel nanoparticles achieved a 42% reduction of paw size, the combination treatment group showed a 33% reduction of the paw size, while the control group had about 20% increase of the paw size. Original paw size before arthritis was induced was 50%. The results are shown in FIG. 2.

In conclusion, the paclitaxel-containing nanoparticles demonstrated therapeutic effect on arthritis. To avoid side effects of long term use of both paclitaxel and the steroid, it is probably better to choose a combination treatment to get similar effect but only half the dosage of each drug.

EXAMPLE 47

The Effect of Capxol on Artery Restenosis

Abnormal vascular smooth muscle proliferation (VSMP) is associated with cardiovascular disorders such as atherosclerosis, hypertension, and most endovascular procedures. Abnormal VSMP is a common complication of percutaneous transluminal coronary angioplasty (PTCA). The incidence of chronic restenosis resulting from VSMP following PTCA has been reported to be as high as 40-50% within 3-6 months.

The high incidence of vascular reocclusion associated with PTCA has led to development of in vivo animal model of restenosis and the search for agents to prevent it. The following study describes the use of Capxol in inhibiting restenosis following intimal trauma of the artery.

Male Sprague-Dawley Rats (Charles River) weighing 350-400 gm are anesthetized with Ketamin and Rompun and the right common carotid artery is exposed for a distance of 3.0 cm. The adherent tissue is cleared to allow two DIETRICH micro bulldog clamps to be placed about 2 cm apart around the carotid without causing crush injury to the vagus or associated superior cervical ganglion and sympathetic cord. No branches are present along this segment of the vessel. A 30-gauge needle attached to a 3 way stopcock is first inserted and then pulled out of the lower end of the isolated segment to make a hole on the wall of the vessel, and then inserted to the upper end for injection. 2-3 ml of phosphate-buffered saline is injected to rinse out all the blood inside the isolated segment then the 3-way stopcock is turned to another connection to a regulated source of compressed air. A gentle stream of air (25 ml. Per minute) is passed along the lumen of the vessel for 3 minutes to produce drying injury of the endothelium. The segment is then refilled with saline prior to removal of the needle from the vessel. Before the clamps are removed the needle holes on the vessel wall are carefully cauterized to prevent bleeding. A swab dampened with saline can be used to press on the needle holes to stop bleeding also. The skin is closed with 7.5-mm metal clips and washed with Betadine.

All the animals received the surgery described above and be sacrificed at the fourteenth day after surgery. The carotid artery on each side were retrieved for pathologic examination. The non-operated side will serve as self control. The experimental groups received different treatment as follows:
Group 1: High dose Capxol treatment:
 Paclitaxel 5 mg (w/100 mg Human Albumin)/kg/week, IV.
Group 2: Low dose Capxol treatment:
 Paclitaxel 1 mg (w/20 mg Human Albumin)/kg/week, IV.
Group 3: Drug vehicle control.
 Human Albumin 100 mg/kg/week. IV.

The carotid artery biopsy samples are preserved in Formalin and then cross sections (8 um) are cut from paraffin blocks and stained with hematoxylin and eosin. The cross-sectional areas of the blood vessel layers (intima, media, and adventitia) are quantified.

The injured Carotid Arteries in the control group showed remarkable accumulation of intimal smooth muscle cells and VSMC invasion of basement membrane. The overall thickness of the wall of carotid artery are doubled. The treatment groups showed a statistically significant decrease in the intimal wall thickening compared to the control.

EXAMPLE 48

In Vivo Targetina of Nanoparticles

By incorporation of certain targeting moieties such as proteins, antibodies, enzymes, peptides, oligonucleotides, sugars, polysaccharides, and the like, into the protein coating of the nanoparticles, it is possible to target specific sites in the body. This targeting ability can be utilized for therapeutic or diagnostic purposes.

EXAMPLE 49

Antibody Targeting of Polymeric Shells

The nature of the polymeric shells of certain aspects of the invention allows for the attachment of monoclonal or polyclonal antibodies to the polymeric shell, or the incorporation of antibodies into the polymeric shell. Antibodies can be incorporated into the polymeric shell as the polymeric microcapsule shell is being formed, or antibodies can be attached to the polymeric shell after preparation thereof. Standard protein immobilization techniques can be used for this purpose. For example, with protein microcapsules prepared from a protein such as albumin, a large number of amino groups on the albumin lysine residues are available for attachment of suitably modified antibodies. As an example, antitumor agents can be delivered to a tumor by incorporating antibodies against the tumor into the polymeric shell as it is being formed, or antibodies against the tumor can be attached to the polymeric shell after preparation thereof. As another example, gene products can be delivered to specific cells (e.g., hepatocytes or certain stem cells in the bone marrow) by incorporating antibodies against receptors on the target cells into the polymeric shell as it is being formed, or antibodies against receptors on the target cells can be attached to the polymeric shell after preparation thereof. In addition, monoclonal antibodies against nuclear receptors can be used to target the encapsulated product to the nucleus of certain cell types.

EXAMPLE 50

Targeting of Immunosuppressive Agent to Transplanted Organs Using Intravenous Delivery of Polymeric Shells Containing Such Agents Immunosuppressive agents are extensively used following organ transplantation for the prevention of rejection episodes. In particular, cyclosporine, a potent immunosuppressive agent, prolongs the survival of allogeneic transplants involving skin, heart, kidney, pancreas, bone marrow, small intestine, and lung in animals. Cyclosporine has been demonstrated to suppress some humoral immunity and to a greater extent, cell mediated reactions such as allograft rejection, delayed hypersensitivity, experimental allergic encephalomyelitis, Freund's adjuvant arthritis, and graft versus host disease in many animal species for a variety of organs. Successful kidney, liver and heart allogeneic transplants have been performed in humans using cyclosporine.

Cyclosporine is currently delivered in oral form either as capsules containing a solution of cyclosporine in alcohol, and oils such as corn oil, polyoxyethylated glycerides and the like, or as a solution in olive oil, polyoxyethylated glycerides, and the like. It is also administered by intravenous injection, in which case it is dissolved in a solution of ethanol (approximately 30%) and cremaphor (polyoxyethylated castor oil) which must be diluted 1:20 to 1:100 in normal saline or 5% dextrose prior to injection. Compared to an intravenous (i.v.) infusion, the absolute bioavailibility of the oral solution is approximately 30% (Sandoz Pharmaceutical Corporation, Publication SDI-Z10 (A4), 1990). In general, the i.v. delivery of cyclosporine suffers from similar problems as the currently practiced i.v. delivery of Taxol, i.e., anaphylactic and allergic reactions believed to be due to the Cremaphor, the delivery vehicle employed for the i.v. formulation. In addition, the intravenous delivery of drug (e.g., cyclosporine) encapsulated as described here avoids dangerous peak blood levels immediately following administration of drug. For example, a comparison of currently available formulations for cyclosporine with the above-described encapsulated form of cyclosporine showed a five-fold decrease in peak blood levels of cyclosporine immediately following injection.

In order to avoid problems associated with the cremaphor, cyclosporine contained within polymeric shells as described above may be delivered by i.v. injection. It may be dissolved in a biocompatible oil or a number of other solvents following which it may be dispersed into polymeric shells by sonication as described above. In addition, an important advantage to delivering cyclosporine (or other immunosuppressive agent) in polymeric shells has the advantage of local targeting due to uptake of the injected material by the RES system in the liver. This may, to some extent, avoid systemic toxicity and reduce effective dosages due to local targeting.

EXAMPLE 51

Use of Capxol for Antibody Targeting

Monoclonal antibodies against various tumors or tissues may be attached to Capxol to enable targeting of Capxol or other drugs prepared by the invention process to the sites of disease. For example, antibodies against ovarian cancer attached to Capxol and administered intraperitoneally would have great benefit to ovarian cancer patients.

EXAMPLE 52

Intravenous Administration of Therapeutics

Intravenous administration of therapeutics, for example, drugs, imaging agents, and the like, predisposes the therapeutic to at least one pass through the liver. As that therapeutic is filtered through the liver, a significant portion of that therapeutic is taken up and sequestered by the liver, and therefore, not available for systemic distribution. Moreover, once taken up by the liver, it is likely to be metabolized, and the resulting metabolic byproducts often have general systemic toxicities. By encapsulating the drug or other therapeutic agent in a coating according to the invention (e.g., using a protein such as albumin), liver sequestration upon intravenous administration is alleviated. Albumin, for example, is known to pass through the liver and become generally distributed throughout the patient. Thus, the sequestration of albumin by the liver does not occur to the same degree as toxic compounds or drugs which have hepatic receptors (or other mechanisms) which initiate processes which result in their removal from the blood stream. By protecting the therapeutic with a coating of a biocompatible polymer (e.g., a human albumin coating), the drug then bypasses the liver and is generally distributed through all organ systems. In accordance with one aspect of the present invention, there is provided a novel method for bypassing the liver, which comprises encapsulating a drug in a human liver albumin (essentially a physiological component). In this way, more of the drug becomes available for systemic therapy. In addition to the increased availability of the drug, there is a decrease in the production of metabolic byproducts of hepatocellular drug degradation. Both the increase in liver bypass and decrease in byproducts of drug metabolism provide a synergistic improvement in the overall drug efficacy. This improved efficacy extends to all drugs and materials that are encapsulated in human albumin.

EXAMPLE 53

Reducina Myelosuppressive (Hematologic Toxicity) Effects and General Toxicity of Drugs Several chemotherapeutic drugs have dose limiting toxicity due to their myelosuppressive effects. Taxol (paclitaxel) is a classic example of such a drug. When administered in its currently approved formulation of cremaphor/ethanol, Taxol produces myelosuppressive effects that limit the repeat administration of the drug and preclude retreatment of a patient for at least 3 weeks in order to allow blood counts of the patient to return to normal. It was postulated that due to the non-toxic biocompatible nature of the drug carrier of certain aspects of the present invention, viz. human albumin, the toxic side effect of myelosuppression may be greatly reduced.

Sprague dawley rats were given paciitaxel in commercial formulation (available from Bristol Myers Squibb (BMS) in cremaphor/ethanol, hereinafter referred to as Taxol) or prepared by an invention method as nanoparticles with albumin. Both formulations were administered by tail vein injection. A single dose level of 5 mg/kg was administered for the Taxol formulation, whereas two dose levels of 5 mg/kg and mg/kg were administered for the invention formulation. The white blood cell counts of the rats were monitored daily after administration as an index of myelosuppression.

For the Taxol formulation (5 mg/kg) it was found that the WBC counts dropped by 47.6% and 63.5% on day 1 and day 2 after administration, respectively, whereas for the invention formulation at 5 mg/kg, the WBC counts increased by 14.7% and 2.4% on day 1 and day 2, respectively. For the higher dose invention formulation at 12 mg/kg, the WBC counts increased by 6.5% and 3.6% on day 1 and day 2, respectively.

These results indicate that short term myelosuppression is greatly reduced by administering the drug in the present invention formulation.

Another indicator of general toxicity is the body eight of the animal. Body weights of the rats were also onitored following administration of paclitaxel. At a dose of 5 mg/kg, the Taxol formulation resulted in a reduction of body eight by 10.4% in 3 days following administration, whereas the same dose of paclitaxel administered in the invention formulation resulted in only a 3.9% drop in body weight, indicating the greatly reduced toxicity of the invention formulation.

It is very surprising that when the invention formulation and Taxol are administered to rats at equivalent doses of paclitaxel, a much higher degree of myelosuppression results for the Taxol group compared to the invention formulation group. This can result in lower incidences of infections and fever episodes (e.g., febrile neutropenia). It can also reduce the cycle time in between treatments which is currently 21 days for Taxol®. With the use of pharmaceutical compositions prepared according to the present invention, this cycle time may be reduced to 2 weeks, 1 week, or less allowing for more effective treatment for cancers. Thus the use of pharmaceutical compositions prepared according to the present invention may provide substantial advantage over Taxol.

EXAMPLE 54

Administration of Bolus Dose of Nanoparticle Formulation

The anticancer drug, paclitaxel, in its commercial BMS formulation with cremaphor/ethanol, cannot be administered as an intravenous bolus. This is due to the extensive toxicity of the vehicle which results in severe anaphylactic reactions and requires patients receiving the drug to be pre-medicated with steroids, antihistamines, and the like. The Taxol® formulation is administered as an intravenous infusion lasting anywhere from 1 hour to 24 hours. In contrast, formulations according to the present invention, due to the use of a non-toxic carrier, can be administered to a patient readily as an intravenous bolus (i.e., in a period less than 1 hour) without the toxicity problems seen in Taxol® formulation that is used clinically today.

The effective dose of paclitaxel for a patient typically lies between 200-500 mg, depending on the patient body weight or body surface. Taxol® has to be administered at a final dosing concentration of 0.6 mg/ml, requiring large infusion volumes (typically in the range of about 300-1000 ml.

In contrast, invention formulations do not have these limitations and can be administered at a desired concentration.

This enables clinicians to treat patients by a rapid intravenous bolus that can be administered in as little as a few minutes. For example, if the invention formulation is reconstituted to a dosing concentration of 20 mg/ml, the infusion volume for a total dose of 200-500 mg is only 10-25 ml, respectively. This is a great advantage in clinical practice.

EXAMPLE 55

Reduction in Toxicity of Paclitaxel in the Nanoparticle Formulation Compared to Taxol It is well known that the anticancer drug, paclitaxel, in its commercial formulation with cremaphor/ethanol (i.e., Taxol), has extensive toxicity which results in severe anaphylactic reactions and requires patients receiving the drug to be pre-medicated with steroids, antihistamines, and the like. The toxicity of the BMS formulation was compared to the nanoparticle formulation of the present invention.

Thus, the formulations were injected intravenously through the tail vein of C57BL mice at different dose levels and toxic effects were monitored by general observation of mice after the injection.

For Taxol, a dose of 30 mg/kg was uniformly lethal within 5 minutes of intravenous administration. For the same dose, the nanoparticle formulation according to the invention showed no apparent toxic effects. The nanoparticle formulation at a dose of 103 mg/kg showed some reduction in body weight of the mice, but even this high dose was not lethal. Doses of approximately 1000 mg/kg, 800 mg/kg and 550 mg/kg were all lethal but differing in time to lethality, which ranged between a few hours to 24 hours. Thus, the lethal dose of the invention formulation is greater than 103 mg/kg but less than 550 mg/kg.

It is therefore clear that the lethal dose of the invention formulation of paclitaxel is substantially higher than that of Taxol formulation. This has great significance in clinical practice where higher doses of chemotherapeutic drugs may be administered for more effective oncolytic activity with greatly reduced toxicity.

EXAMPLE 56

Determination of the $LD_{50}$ in Mice for Taxol Produced by Invention Methods and Taxol Following a Single Intravenous Administration The $LD_{50}$ of Capxol™, Taxol and their carrier vehicles was compared following a single intravenous administration. A total of 48 CD1 mice were used. Paclitaxel doses of 30, 103, 367, 548, and 822 mg/kg were tested for Capxol™ and doses of 4, 6, 9, 13.4, and 20.1 mg/kg paclitaxel for Taxol. The dose for human albumin, the vehicle for Capxol™, was only tested at 4.94 g/kg (corresponds to a dose of 548 mg/mL Capxol™) because human albumin is not considered toxic to humans. The doses tested for the Taxol vehicle (Cremophor EL®) were 1.5, 1.9, 2.8, and 3.4 mL/kg which correspond to doses of 9, 11.3, 16.6, and 20.1 mg/kg of paclitaxel, respectively. Three to four mice were dosed with each concentration.

The results indicated that paclitaxel administered in Capxol™ is less toxic than Taxol or the Taxol vehicle thereof administered alone. The $LD_{50}$ and $LD_{10}$ for Capxol™ were 447.4 and 371.5 mg/kg of paclitaxel, 7.53 and 5.13 mg/kg of paclitaxel in Taxol, and 1325 and 794 mg/kg of the Taxol vehicle, (corresponds to a dose of 15.06 and 9.06 mg/kg Taxol). In this study, the $LD_{50}$ for Capxol™ was 59 times greater than Taxol and 29 times greater than the Taxol vehicle alone. The $LD_{10}$ for paclitaxel in Capxol™ was 72 times greater than paclitaxel in Taxol. Review of all the data in this study suggests that the Taxol vehicle is responsible for much of the toxicity of Taxol. It was seen that the mice receiving Taxol and Taxol vehicle showed classic signs of severe hypersensitivity indicated by bright pink skin coloration shortlt after administration. No such reaction was seen for the Capxol™ and Capxol™ vehicle groups. Results are presented in Table 2.

TABLE 2

| | Single Intravenous Administration | | | | | |
|---|---|---|---|---|---|---|
| Group | Dose (mg/kg) | # of Animals sssss (n) | # of Deaths | % Survival | $LD_{50}$ (mg/kg) | MTD or $LD_{10}$ (mg/kg) |
| Invention | 822 | 3 | 3 | 0 | 447.4 | 371.5 |
| | 548 | 4 | 4 | 0 | | |
| | 367 | 3 | 0 | 100 | | |
| | 103 | 3 | 0 | 100 | | |
| | 30 | 3 | 0 | 100 | | |
| Taxol | 20.1 | 4 | 4 | 0 | 7.53 | 5.13 |
| | 13.4 | 4 | 4 | 0 | | |
| | 9 | 3 | 2 | 33 | | |
| | 6 | 4 | 1 | 75 | | |
| | 4 | 3 | 0 | 100 | | |

These high doses of Capxol™ were administered as bolus injections and represent the equivalent of approximately 80-2000 mg/m² dose in humans. The $LD_{10}$ or maximum tolerated dose of Capxol™ in this study is equivalent to approximately 1000 mg/m² in humans. This is significantly higher than the approved human dose of 175 mg/m² for Taxol.

To our surprise, it was found that the vehicle, Cremophor/Ethanol, alone caused severe hypersensitivity reactions and death in several dose groups of mice. The LD50 data for the Taxol vehicle alone shows that it is considerably more toxic than Capxol™ and significantly contributes to the toxicity of Taxol. It has been unclear in the literature, the cause of hypersensitivity, however, based on these data, we believe that HSR's can be attributed to the Taxol vehicle.

EXAMPLE 57

Determination of the $LD_{50}$ in Mice of Taxol® and Taxol Following Multiple Intravenous Administration The $LD_{50}$ of Capxol™ and BMS-Taxol and their carrier were compared following single intravenous administrations. A total of 32 CD1 mice were used. Capxol™ with paclitaxel doses of 30, 69, and 103 mg/kg were administered daily for five consecutive days. Taxol with paclitaxel doses of 4, 6, 9, 13.4, and 20.1 mg/kg was administered daily for 5 consecutive days. Four mice were dosed with each concentration. Results are presented in Table 3.

TABLE 3

| | Multiple Intravenous Administrations | | | | | |
|---|---|---|---|---|---|---|
| Group | Dose (mg/kg) | # of Animals | # of Deaths | # of Survival | $LD_{50}$ (mg/kg) | MTD or $LD_{10}$ |
| Capxol ™ | 103 | 4 | 4 | 0 | 76 | 64 |
| | 69 | 4 | 1 | 75 | | |
| | 30 | 4 | 0 | 100 | | |
| Taxol | 20.1 | 4 | 4 | 0 | 8.0 | 4.3 |
| | 13.4 | 4 | 4 | 0 | | |
| | 9 | 4 | 2 | 50 | | |
| | 6 | 4 | 1 | 75 | | |
| | 4 | 4 | 0 | 100 | | |

The results indicated that Capxol™ is less toxic than Taxol. The $LD_{50}$ and $LD_{10}$ of Capxol™ were 76.2 and 64.5 mg/kg of paclitaxel, respectively, compared to 8.07 and 4.3 mg/kg of paclitaxel in Taxol, respectively. In this study, the $LD_{50}$ for Capxol™ was 9.4 times higher than for Taxol. The $LD_{10}$ for Capxol™ was 15 times higher for Capxol™ than for Taxol. The results of this study suggests that the Capxol™ is less toxic than Taxol® when administered in multiple doses at daily intervals.

EXAMPLE 58

Toxicity and Efficacy of Two Formulations of Capxol™ and Taxol®

A study was performed to determine the efficacy of Capxol™, Taxol, and the Capxol™ vehicle in female athymic NCr-nu mice implanted with MX-1 human mammary tumor fragments.

Groups of 5 mice each were given intravenous injections of Capxol™ formulations VR-3 or VR-4 at doses of 13.4, 20, 30, 45 mg/kg/day for 5 days. Groups of 5 mice were also each given intravenous injections of Taxol at doses of 13.4, 20 and 30 mg/kg/day for five days. A control group of ten mice was treated with an intravenous injection of Capxol™ vehicle control (Human Albumin, 600 mg/kg/day) for 5 days. Evaluation parameters were the number of complete tumor regressions, the mean duration of complete regression, tumor-free survivors, and tumor recurrences.

Treatment with Capxol™ formulation VR-3 resulted in complete tumor regressions at all dose levels. The two highest doses resulted in 100% survival after 103 days. Capxol™ formulation VR-4 resulted in complete tumor regression in the three highest dose groups, and 60% regressions at 13.4 mg/kg/day. Survival rates after 103 days were somewhat less than with formulation VR-4. Treatment with Taxol at 30, 20, and 13.4 mg/kg/day resulted in 103 day survival rates of 40%, 20%, and 20% respectively. Treatment with the control vehicle had no effect on tumor growth and the animals were sacrificed after 33 to 47 days. Results are presented in Table 4.

TABLE 4

| Dosage (mg/kg/day) | CR/Total VR- | CR/Total VR- | CR/Total TAX | TSF/TR VR- | TSF/TR VR- | TSF/TR TAX | DCR (days) VR- | DCR (days) VR- | DCR (days) TAX | NonSpecific Deaths/Total VR- | NonSpecific Deaths/Total VR- | NonSpecific Deaths/Total TAX |
|---|---|---|---|---|---|---|---|---|---|---|---|---|
| 45 | 5/5 | 5/5 | NA | 5/0 | 3/2 | NA | >88 | >73 | NA | 0/5 | 0/5 | NA |
| 30 | 5/5 | 5/5 | 4/4 | 5/0 | 5/0 | 2/2 | >88 | >88 | >56 | 0/5 | 0/5 | 1/5 |
| 20 | 5/5 | 5/5 | 4/4 | 1/4 | 2/3 | 1/3 | >51 | >47 | >57 | 0/5 | 0/5 | 1/5 |
| 13 | 4/5 | 3/5 | 4/5 | 0/5 | 0/5 | 1/4 | 10 | 8 | >29 | 0/5 | 0/5 | 0/5 |

CR = Complete tumor regression;
TFS = Tumor free survivor;
TR = Tumor recurrence;
DCR = days of complete regression These unexpected and surprising results show an increased efficacy for the two Capxol™ formulations compared to Taxol. In addition, higher doses of paclitaxel are achieved in the Capxol™ groups due to lower toxicity of the formulation. These high doses were administered as bolus injections.

EXAMPLE 40

Blood Kinetics and Tissue Distribution on ³H-Taxol® and Capxol™ Following a Single Intravenous Dose in the Rat Two studies were performed to compare the pharmacokinetics and tissue distribution of ³H-paclitaxel formulated in Capxol™ and Taxol Injection Concentrate. Fourteen male rats were intravenously injected with 10 mg/kg of ³H-Taxol and 10 rats with 4.9 mg/kg. Ten male rats were intravenously injected with 5.1 mg/kg ³H-Capxol in the above study.

Levels of both total radioactivity and paclitaxel decline bi-phasically in blood of rats following 5 mg/kg IV bolus doses of either ³H-Taxol or ³H-Capxol™. However, the levels of both total radioactivity and paclitaxel are significantly lower following administration of ³H-Capxol™ following a similar ³H-Taxol dose. This lower level is more rapidly distributed out of the blood.

The blood HPLC profile shows a similar pattern of metabolism to highly polar metabolite(s) for both ³H-Capxol™ and ³H-Taxol. However, the rate of metabolism appears significantly slower for 3H-Capxol as 44.2% of blood radioactivity remains as paclitaxel 24 hours post-dose versus 27.7% for ³H-Taxol. The excretion of radioactivity occurs only minimally in the urine and predominantly in the feces for ³H-Capxol™ which is similar to reported excretion patterns for H-Taxol. The blood kinetics for total radioactivity and paclitaxel following IV administration of ³H-Capxol™ or ³H-Taxol at 5 mg/kg are presented in Table 5.

TABLE 5

| Treatment | $AUC_{0-24}$ (mg eq. hr/mL) | Extrapolated $C_0$ (mg eq/mL) | Observed $C_{max}$ (mg eq/(mL) | Observed $T_{max}$ (hr) | $t_{1/2}\beta$ (hr) |
|---|---|---|---|---|---|
| Total Radioactivity | | | | | |
| ³H-Capxol ™ | 6.1 | 7.6 | 4.2 | 0.03 | 19.0 |
| ³H-Taxol | 10.2 | 19.7 | 13.5 | 0.03 | 19.7 |
| Paclitaxel | | | | | |
| 3H-Capxol ™ | 3.7 | 7.0 | 4.0 | 0.03 | 11.4 |
| 3H-Taxol | 5.4 | 17.1 | 11.8 | 0.03 | 7.2 |

The tissue radioactivity levels are higher following ³H-Capxol™ administration than ³H-Taxol administration for 12 of 14 tissues. The tissue/blood ppm. ratios are higher in all tissues for $^3$H-Capxol™ dosed animals as the blood levels are lower. This supports the rapid distribution of $^3$H-Capxol™ from the blood to the tissues suggested by the blood kinetic data.

$^3$H-Paclitaxel formulated in Capxol™ shows a similar pharmacokinetic profile to $^3$H-paclitaxel formulated in Taxol® for Injection concentrate, but tissue/blood ppm ratios and metabolism rates differ significantly. A significantly lower level of total radioactivity for Capxol™ treated animals than for Taxol™ treated animals in the 2 minute post administration blood sample indicates that the $^3$H-Capxol is more rapidly distributed out of the blood. However, the rate of metabolism appears significantly slower for $^3$H-Capxol™ as 44% of blood reactivity remains as paclitaxel at 24 hours post-administration versus 28% for $^3$H-Taxol®.

This finding for Capxol™ is surprising and provides a novel formulation to achieve sustained activity of paclitaxel compared to Taxol. Taken together with local high concentrations, this enhanced activity should result in increased efficacy for the treatment of primary tumors or metastases in organs with high local concentrations.

Tissue distributions are presented in Table 6 below. The data represent the mean and standard deviations of 10 rats in each group (Capxol™ and Taxol).

TABLE 6

Radioactive Residues in Tissues of Male Rats. Expressed as ppm following a single intravenous dose of $^3$H-Capxol ™ and $^3$H-Taxol ® at 5 mg/kg

| Sample | Capxol ™ Mean Values | ± SD | Taxol Mean Values | ± SD |
|---|---|---|---|---|
| Brain | 0.106 | 0.008 | 0.145 | 0.020 |
| Heart | 0.368 | 0.063 | 0.262 | 0.037 |
| Lung | 1.006 | 0.140 | 0.694 | 0.057 |
| Liver | 1.192 | 0.128 | 1.37 | 0.204 |
| Kidney | 0.670 | 0.110 | 0.473 | 0.068 |
| Muscle | 0.422 | 0.120 | 0.386 | 0.035 |
| GI Tract | 0.802 | 0.274 | 0.898 | 0.243 |
| Testes | 0.265 | 0.023 | 0.326 | 0.047 |
| Pancreas | 0.963 | 0.357 | 0.468 | 0.070 |
| Carcass | 0.596 | 0.070 | 0.441 | 0.065 |
| Bone | 0.531 | 0.108 | 0.297 | 0.051 |
| Spleen | 0.912 | 0.131 | 0.493 | 0.070 |
| Prostate | 1.728 | 0.356 | 1.10 | 0.161 |
| Seminal Vesicles | 1.142 | 0.253 | 1.20 | 0.237 |
| Blood | 0.131 | 0.010 | 0.181 | 0.020 |
| Plasma | 0.131 | 0.012 | 0.196 | 0.026 |

The data show significantly higher levels of accumulation of Capxol™ in the several organs when compared to Taxol®. These organs include prostate, pancreas, kidney, lung, heart, bone, and spleen. Thus Capxol™ may be more effective than Taxol® in the treatment of cancers of these organs at equivalent levels of paclitaxel.

Levels in the prostate tissue are of particular interest in the treatment of prostatic cancer. This surprising and unexpected result has implications for the treatment of prostate cancer. Table 7 below shows the data for individual rats (10 in each group) showing increased accumulation of paclitaxel in the prostate for Capxol™ as compared to Taxol®. The basis for the localization within the prostate could be a result of the particle size of the formulation (20-400 nm), or the presence the protein albumin in the formulation which may cause localization into the prostatic tissue through specific membrane receptors (gp 60, gp 18, gp 13 and the like). It is also likely that other biocompatible, biodegradable polymers other than albumin may show specificity to certain tissues such as the prostate resulting in high local concentration of paclitaxel in these tissues as a result of the properties described above. Such biocompatible materials are contemplated to be within the scope of this invention. A preferred embodiment of a composition to achieve high local concentrations of paclitaxel in the prostate is a formulation containing paclitaxel and albumin with a particle size in the range of 20-400 nm, and free of cremophor. This embodiment has also been demonstrated to result in higher level concentrations of paclitaxel in the pancreas, kidney, lung, heart, bone, and spleen when compared to Taxol at equivalent doses.

TABLE 7

Data for 10 rats in each group
Dose 5 mg/kg paclitaxel

| INVENTION-Taxol | Taxol ® |
|---|---|
| 1.228 | 1.13 |
| 2.463 | 1.04 |
| 1.904 | 0.952 |
| 1.850 | 1.42 |
| 1.660 | 1.31 |
| 1.246 | 1.08 |
| 1.895 | 1.03 |
| 1.563 | 0.95 |
| 1.798 | 0.94 |
| 1.676 | 1.18 |
| Mean 1.728 | Mean 1.103 |
| SD 0.36 | SD 0.16 |

This data shows that the localication of Capxol™ to the prostate is about 150% comparied to Taxol®.

This unexpected localization of paclitaxel to the prostate in the Capxol™ formulation may be exploited for the delivery of other pharmacologically active agents to the prostate for the treatment of other disease states affecting that organ, e.g., antibiotics in a similar formulation for the treatment of prostatitis (inflammation and infection of the prostate), therapeutic agents effective for the treatment of benign prostatic hypertrophy maybe formulated in a similar fashion to achieve high local delivery. Similarly, the surprising finding that Capxol™ provides high local concentrations to the heart can be exploited for the treatment of restenosis as well as atherosclerotic disease in coronary vessels. Paclitaxel has been demonstrated to have a therapeutic effect in the prevention of restenosis and atherosclerosis and Capxol™ thus is an ideal vehicle. Furthermore it has been demonstrated that polymerized albumin preferentially binds to inflamed endothelial vessels possibly through gp60, gp18 and gp13 receptors.

EXAMPLE 60

Blood Kinetics and Tissue Distribution of Paclitaxel Following Multiple Intravenous Dose Levels of Capxol™ in the Rat The study using $^3$H-Capxol™ was supplemented by treating four additional groups of rats with a single bolus dose of 9.1 mg/kg, 26.4 mg/kg, 116.7 mg/kg, and 148.1 mg/kg of paclitaxel in Capxol™. Blood was collected from the tail vein and the AUC$_{0-24}$ was calculated. At 24 hours, blood samples were collected; extracted, and the extract injected on HPLC to determine the level of parent compound in the blood.

The blood kinetics for total radioactivity and paclitaxel following IV administration of $^3$H-Capxol™ are presented in Table 8.

TABLE 8

| Group/Dose (mg/kg) | $AUC_{0-24}$ (μg eq. hr/ml) | Extrapolated $C_0$ (μg eq/ml) | Observed $C_{max}$ (μg eq/(ml) | Observed $T_{max}$ (hr) | $t_{1/2}\beta$ (hr) |
|---|---|---|---|---|---|
| A/9.1 | 11.5 | 10.2 | 7.19 | 0.03 | 22.3 |
| B/26.4 | 43.5 | 44.8 | 29.5 | 0.03 | 16.0 |
| C/116.7 | 248.9 | 644.6 | 283.3 | 0.03 | 8.48 |
| D/148.1 | 355.3 | 1009.8 | 414.2 | 0.03 | 9.34 |

As the dose of paclitaxel was increased, the area under the curve was proportionally increased. The level of parent compound after 24 hours was increased by a factor of 8.5 (0.04 ppm-0.34 ppm), going from the 9 mg/kg dose to the 148 mg/kg dose.

EXAMPLE 61

Determination of the Toxicity in Rats of Capxol™ and Taxol Following a Single Intravenous Administration The objective of the study was to determine the toxicity of Capxol™ following a single IV administration in male and female rats. Capxol™ was administered to 6 male and 6 female rats at doses of 5, 9, 30, 90 and 120 mg/kg. One half of the animals from each dose group were euthanized and necropsied on Day 8. The remaining animals were necropsied on Day 31. The results of Capxol™-treated animals were compared to the results of normal saline and vehicle control groups as well as to the results of animals treated with 5, 9 and 30 mg/kg Taxol.

Animals were examined immediately after dosing, 1 hour and 4 hours past administration, and once daily thereafter. Blood was collected from each animal for hematological and serum determination prior to euthanasia.

Thirteen deaths occurred during the 30 day observation period. All 12 animals treated with Taxol at a dose of 30 mg/kg paclitaxel died by day 4. Only one animal treated with Capxol™ died. The Capxol™ treated animal received 90 mg/kg paclitaxel and was found dead on day 15. No other animals treated with Capxol™ died at the 90 kg or 120 mg/kg dose, therefore the death is not thought to be treatment related.

During the first four hour observation period, piloerection and staggering gait were observed in the majority of animals treated with Taxol, possibly due to the alcohol content of the drug. Piloerection was noted in a few animals treated with Capxol™. Animals treated with Taxol at a dose of 30 mg/kg paclitaxel were observed with piloerection and lethargy and were found dead by day 4. No overt signs of toxicity were observed in Capxol™ treated animals, except for a few incidences of piloerection at the 90 mg/ml and 120 mg/ml dose levels.

No abnormalities were reported in Capxol™ treated animals. Gross necropsy results for day 8 and day 31 were normal. Significant dose related changes were seen in the male reproductive organs in animals treated with Capxol™. A degeneration and vacuolation of epididymal ductal epithelial cells, often accompanied by multifocal interstitial lymphocytic infiltrate, was observed. There was increasing severe atrophy of seminiferous tubules seen in the testes as he dose of Capxol™ increased. In the pathologist's opinion, there were significant lesions observed in the male reproductive organs of the animals treated with 9, 30, 90, and 120 mg/kg Capxol™. These changes involved diffuse degeneration and necrosis of the testes. These changes were the most prevalent in animals that received higher doses of Capxol™. No changes were seen in the testes from untreated control animals, vehicle control animals, or those treated with Taxol.

This finding is unexpected and has significant therapeutic implications for the treatment of hormone dependent cancers such as prostate cancer. Removal of the testes (orchiectomy) is a therapeutic approach to the treatment of rostate cancer. Capxol™ represents a novel formulation for the treatment of this disease by achieving high local concentration of paclitaxel at that site, by sustained activity of the active ingredient, by reduction of testicular function and without the toxic cremophor vehicle. Treatment with Capxol™ thus allows for reduction in levels of testosterone and other androgen hormones.

Cerebral cortical necrosis was seen at the mid dose level of the Taxol treated animals. This may explain the deaths of the animals treated with even higher doses of Taxol. No cerebral lesions were seen in animals treated with Capxol™.

This lack of cerebral or neurologic toxicity is surprising and has significant implications in both the treatment of brain tumors and the ability to achieve high systemic doses ranging from 5-120 mg/kg in rats (equivalent to 30-700 mg/m² dose in humans)

To summarize, Capxol™ was considerably less toxic than Taxol. No Taxol animals survived at the doses higher than 9 mg/kg. With the exception of an incidental death at 90 mg/kg Capxol™, all animals which received Capxol™ survived at doses up to and including 120 mg/kg. There was a high dose-related effect of Capxol™ on the male reproductive organs and a suppression in male body weight. Female rats did not demonstrate any toxic effects from the administration of Capxol™ at doses up to and including 120 mg/kg. These high doses were administered as bolus injections and represent the equivalent of 30-700 mg/m² dose in humans.

EXAMPLE 62

Pharmacokinetic (PK) Data for Cyclosporine Nanoparticles (Capsorine I.V.) Following Intravenous Administration Comparison with Sandimmune I.V. (Formulation Currently Marketed by Sandoz)

Nanoparticles of cyclosporine (Capsorine I.V.) prepared as described above (Examples 13 and 14) were reconstituted in saline and administered to a first group of 3 Sprague Dawley rats by intravenous bolus. A second group of 3 rats were given Sandimmune I.V., which contains cremaphor/ethanol, after dilution in saline. Each group received the same dose of 2.5 mg/kg cyclosporine. Blood samples were taken at times 0, 5, 15, 30 (minutes), and 1, 2, 4, 8, 24, 36 and 48 (hours). Levels of cyclosporine in the blood were assayed by HPLC and typical PK parameters were determined. The PK curves showed typical decay over time as follows:

| | Decay Over Time | |
|---|---|---|
| | AUC, mg-hr/ml | Cmax, ng/ml |
| Capsorine I.V. | 12,228 | 2,853 |
| Sandimmune I.V. | 7,791 | 2,606 |

In addition, due to toxicity of the Sandimmune I.V. formulation, 2 of 3 rats in that group died within 4 hours after dosing. Thus the nanoparticle formulation (Capsorine I.V.) according to the present invention shows a greater AUC and no toxicity compared to the commercially available formulation (Sandimmune I.V.).

EXAMPLE 63

Pharmacokinetic (PK) Data for Cyclosporine Nanodroplets (Capsorine Oral) Following Oral Administration Comparison with Neoral (Formulation Currently Marketed by Sandoz)

Nanodroplets of cyclosporine prepared above were administered in orange juice, to a first group of 3 Sprague awley rats by oral gavage. A second group of 3 rats were given Neoral, a commercially available microemulsion formulation containing emulsifiers, after dilution in orange juice, also by oral gavage. Each group received the same dose of 12 mg/kg cyclosporine in an identical volume of orange juice. Blood samples were taken at times 0, 5, 15, 30 (minutes), and 1, 2, 4, 8, 24, 36 and 48 (hours). Levels of cyclosporine in the blood were assayed by HPLC and typical PK arameters were determined. The PK curves showed typical decay over time as follows:

|  | Decay Over Time | |
|---|---|---|
|  | AUC, mg-hr/ml | Cmax, ng/ml |
| Capsorine Oral | 3,195 | 887 |
| Neoral | 3,213 | 690 |

Thus, the nanodroplet formulation (Capsorine Oral) of the present invention shows a similar PK behavior to the commercially available formulation (Neoral).

EXAMPLE 64

Clinical Investigation with Capxol™: Objectives and Advantages

The rationale for selecting the initial dose for Phase I/II trials will be based on the dramatically lower preclinical toxicity data for the Capxol™ formulation compared to Taxol formulation. The preclinical data above indicates that initial dosing levels of Capxol™ for Phase I/II studies will use the established MTD (maximum tolerated dose) for paclitaxel in the Taxol formulation. Based on the current preclinical data, it is anticipated at this time that the clinical objectives for market approval will be to eliminate the need for premedication prior to administration of paclitaxel; determine equivalent dose of Capxol™ to Taxol—i.e., to determine the dose at which equivalent antitumor response is obtained; and eliminate the need for continuous i.v. infusion (3 to 24 hours) for paclitaxel administration and replace by administration over much shorter periods (<1 hour or bolus).

There are many potential advantages of the Capxol™ formulation for paclitaxel. Capxol™ is a lyophilized powder containing only paclitaxel and human serum albumin. Due to the nature of the colloidal solution formed upon reconstitution of the lyophilized powder toxic emulsifiers, such as cremaphor (in the BMS formulation of paclitaxel) or polysorbate 80 (as in the Rhone Poulenc formulation of docetaxel), and solvents such as ethanol to solubilize the drug, are not required. Removing toxic emulsifers will reduce the incidences of severe hypersensitivity and anaphylactic reactions that are known to occur from products like Taxol.

In addition, no premedication with steroids and antihistamines are anticipated prior to administration of the drug.

Due to reduced toxicities, as evidenced by the $LD_{10}/LD_{50}$ studies, higher doses may be employed which will result in greater efficacy.

The reduction in myelosuppression (as compared with Taxol) is expected to reduce the period of the treatment cycle (currently 3 weeks) and improve therapeutic outcomes.

Capxol™ can be administered at much higher concentrations (up to 20 mg/ml) compared with Taxol (0.6 mg/ml), allowing much lower volume infusions, and possibly administration as an intravenous bolus.

A recognized problem with Taxol is the precipitation of paclitaxel in indwelling catheters. This results in erratic and poorly controlled dosing. Due to the inherent stability of the colloidal solution of the new formulation, Capxol™, the problem of precipitation is alleviated.

The literature suggests that particles in the low hundred nanometer size range preferentially partition into tumors through leaky blood vessels at the tumor site. The colloidal particles of paclitaxel in the Capxol™ formulation are therefore expected to show a preferential targeting effect, greatly reducing the side effects of paclitaxel administered in the BMS formulation.

EXAMPLE 65

Outline of Capxol™ Clinical Trial Design

Indication:
Metastatic Breast cancer
Dosing plan:
The rationale for selecting the initial dose for Phase I/II trials will be based on the significantly lower preclinical toxicity data (Single dose $LD_{10}$ data in mice) for the Capxol™ formulation compared to the BMS formulation. The single dose $LD_{10}$ in mice is determined to be 398.1 mg/kg. Conversion of this dose to a surface area basis (3 times the mg/kg value) gives an estimate of 1194.3 or about 1200 mg/m². A conservative starting dose 1/10th of this value for humans results in a dose of 120 mg/m². However, it is already well established that paclitaxel is safe at a dose of 175 mg/m² and based on a pilot study with Capxol™ showing lower myelosuppression in rats, a dose of 175 mg/m² should be safe for the Capxol™ formulation. The Capxol™ solution will be delivered in approximately 15-30 minutes or less, if possible.

EXAMPLE 66

Outline of Capxol™ Clinical Development Program: Combination Phase I/II Dose Finding Study/Limited Efficacy Trial Patients/Purpose: Patients having advanced breast metastatic disease refractory to standard therapies. The goal of this trial will be to establish the response rate to Capxol™ as a single agent in patients with metastatic breast cancer.

Dosing—Phase I Component: The initial dose to be used in the Phase I component of the trial will be the known maximum tolerated dose (MTD) for Paclitaxel (175 mg/m²). Subsequent doses will be escalated in 25% steps until the MTD is reached. There will be 3 patients at each of the initial Capxol™ dose levels, expanding to 6 patients at the MTD. The ability to move to the next dose level will be based on the adverse event pattern. That is, the study will be discontinued whenever 2 or more patients out of 6 at a particular dose level exhibit Grade 3 non-myelosuppressive toxicity or Grade 4 myelosuppressive toxicity (on the WHO Toxicity scale). The dose for Capxol™ will be designated as the dose immediately preceding the dose at which the trial was discontinued. Alternative schedules of drug administration, such as daily x 5 or 24 hour infusion may also be explored if necessary, based on the results of the initial, single dose bolus schedule.

Pharmacokinetics: For selected patients, a full pharmacokinetic study will be performed using serum drawn at appropriately designated time points. Parameters such as $t^{1/2}$ ($\alpha$ and $\beta$ phase), AUC, $C_{max}$, Clearance and volume of distribution will be determined.

Patients—Phase II Component: Having established the MTD, breast cancer patients similar to those used in the original Paclitaxel trials will be selected for the Phase II component. The number will be based on the desire to establish tumor response rate with acceptable precision at the 95% confidence level. As such, the study will be single armed with the goal of establishing equivalence with standard Paclitaxel by showing that the confidence interval contains the expected response rates for Capxol™. The patient sample size used will be 30 patients, which is common for the Phase II component of a Phase I/II study.

Measurement: The primary outcome will be the tumor response rate (CR/PR) for the enrolled patients. In addition, the time to response, duration of response, and survival time will be monitored. Safety of the treatment will also be evaluated from adverse event rates and changes in standard laboratory parameters.

That which is claimed is:

1. A pharmaceutical formulation comprising:
paclitaxel at a concentration between 5 mg/ml and 15 mg/ml,
wherein the pharmaceutical formulation is an aqueous suspension that is stable for at least 3 days under at least one of room temperature or refrigerated conditions, wherein the pharmaceutical formulation comprises nanoparticles comprising a solid core of paclitaxel and an albumin coating,
and wherein the size of the nanoparticles in the formulation is less than 400 nm.

2. The pharmaceutical formulation of claim 1, wherein the pharmaceutical formulation is a stable aqueous suspension reconstituted from a sterile lyophilized powder.

3. The pharmaceutical formulation of claim 2, wherein the pharmaceutical formulation comprises paclitaxel at a concentration of 5 mg/ml.

4. The pharmaceutical formulation of claim 2, wherein the average diameter of the nanoparticles is no greater than 220 nm.

5. The pharmaceutical formulation of claim 2, wherein there is substantially no precipitation of paclitaxel for at least 3 days under at least one of room temperature or refrigerated conditions.

6. The pharmaceutical formulation of claim 1, wherein the average nanoparticle size does not substantially change for at least 3 days under at least one of room temperature or refrigerated conditions.

7. The pharmaceutical formulation of claim 1, wherein the solid core is substantially free of polymeric material.

8. The pharmaceutical formulation of claim 1, wherein the albumin coating has free albumin associated therewith, and wherein a portion of the paclitaxel is contained within the albumin coating and a portion of the paclitaxel is associated with the free albumin.

9. The pharmaceutical formulation of claim 1, wherein at least a portion of the albumin is crosslinked by disulfide bonds.

10. The pharmaceutical formulation of claim 1, wherein the paclitaxel is substantially amorphous.

11. The pharmaceutical formulation of claim 1, wherein the paclitaxel is substantially crystalline.

12. A method of treatment, comprising administering an effective amount of the composition of claim 1 to a patient to treat a tumor.

13. The method of claim 12, wherein the composition is administered parenterally, orally, intravenously, subcutaneously, intraperitoneally, intrathecally, intramuscularly, by inhalation, topically, transdermally, rectally, or vaginally.

14. The method of claim 13, wherein the composition is administered intravenously.

15. The method of claim 14, wherein the pharmaceutical formulation is infused, and the infusion volume is no greater than 200 ml.

16. A method of treatment, comprising administering an effective amount of the composition of claim 1 to a patient to treat breast cancer.

17. The method of claim 16, wherein the composition is administered parenterally, orally, intravenously, subcutaneously, intraperitoneally, intrathecally, intramuscularly, by inhalation, topically, transdermally, rectally, or vaginally.

18. The pharmaceutical formulation of claim 1, wherein the average diameter of the nanoparticles is no greater than about 200 nm.

19. The pharmaceutical formulation of claim 2, wherein the average diameter of the nanoparticles is no greater than about 200 nm.

20. The pharmaceutical formulation of claim 3, wherein the average diameter of the nanoparticles is no greater than about 200 nm.

21. The pharmaceutical formulation of claim 7, wherein the average diameter of the nanoparticles is no greater than about 200 nm.

22. The pharmaceutical formulation of claim 8, wherein the average diameter of the nanoparticles is no greater than about 200 nm.

23. The pharmaceutical formulation of claim 1, wherein the albumin is human albumin.

24. The pharmaceutical formulation of claim 2, wherein the albumin is human albumin.

25. The pharmaceutical formulation of claim 3, wherein the albumin is human albumin.

26. The pharmaceutical formulation of claim 7, wherein the albumin is human albumin.

27. The pharmaceutical formulation of claim 10, wherein the albumin is human albumin.

* * * * *

UNITED STATES PATENT AND TRADEMARK OFFICE
CERTIFICATE OF CORRECTION

| | | Page 1 of 1 |
|---|---|---|
| PATENT NO. | : 8,853,260 B2 | |
| APPLICATION NO. | : 11/520479 | |
| DATED | : October 7, 2014 | |
| INVENTOR(S) | : Desaid et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1127 days.

Signed and Sealed this
Thirteenth Day of October, 2015

Michelle K. Lee
*Director of the United States Patent and Trademark Office*